(12) United States Patent
Cerny et al.

(10) Patent No.: US 8,921,647 B2
(45) Date of Patent: Dec. 30, 2014

(54) MOLECULAR MARKERS ASSOCIATED WITH YELLOW FLASH IN GLYPHOSATE TOLERANT SOYBEANS

(75) Inventors: Liesa Cerny, Chesterfield, MO (US); Kunsheng Wu, Ballwin, MO (US); Tom Floyd, Bloomington, IL (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/224,036

(22) Filed: Sep. 1, 2011

(65) Prior Publication Data

US 2012/0084879 A1 Apr. 5, 2012

Related U.S. Application Data

(60) Provisional application No. 61/380,024, filed on Sep. 3, 2010.

(51) Int. Cl.
*C12N 15/82* (2006.01)
*C12Q 1/68* (2006.01)
*A01H 5/00* (2006.01)
*A01H 1/04* (2006.01)

(52) U.S. Cl.
CPC .......... *C12Q 1/6895* (2013.01); *C12Q 2600/13* (2013.01); *A01H 1/04* (2013.01)
USPC ............................ 800/267; 800/300; 800/312

(58) Field of Classification Search
None
See application file for complete search history.

(56) References Cited

U.S. PATENT DOCUMENTS

| | | | |
|---|---|---|---|
| 5,659,116 A | 8/1997 | Rhodes | |
| 5,750,857 A | 5/1998 | Rhodes | |
| 5,973,235 A | 10/1999 | Holmes | |
| 6,005,170 A * | 12/1999 | Lussenden | 800/312 |
| 6,080,917 A | 6/2000 | Lussenden | |
| 6,143,953 A | 11/2000 | Buettner | |
| 6,184,442 B1 | 2/2001 | Nickell | |
| 6,346,658 B1 | 2/2002 | Moots | |
| 6,348,644 B1 | 2/2002 | Rhodes | |
| 6,632,982 B1 | 10/2003 | Floyd | |
| 6,660,912 B1 | 12/2003 | Owen | |
| 6,683,233 B1 | 1/2004 | Owen | |
| 6,858,783 B2 | 2/2005 | Eby et al. | |
| 6,881,879 B2 | 4/2005 | Floyd | |
| 6,884,927 B1 | 4/2005 | Eby | |
| 6,900,372 B2 * | 5/2005 | Hicks | 800/312 |
| 6,933,423 B2 | 8/2005 | Narvel | |
| 7,067,723 B2 | 6/2006 | Narvel | |
| 7,071,388 B2 | 7/2006 | Narvel | |
| 7,294,764 B2 | 11/2007 | Leitz | |
| 7,378,578 B2 | 5/2008 | Narvel | |
| 7,388,131 B1 | 6/2008 | Hicks | |
| 7,479,582 B2 | 1/2009 | Moots et al. | |
| 7,482,516 B2 | 1/2009 | Hicks | |
| 7,498,489 B2 | 3/2009 | Jenkinson et al. | |
| 7,504,565 B2 | 3/2009 | Jenkinson et al. | |
| 7,554,014 B2 | 6/2009 | Moots et al. | |
| 7,569,750 B2 | 8/2009 | Behm | |
| 7,728,197 B1 | 6/2010 | Bowers et al. | |
| 2006/0288444 A1 * | 12/2006 | McCarroll et al. | 800/279 |
| 2009/0036308 A1 | 2/2009 | Guida, Jr. et al. | |
| 2009/0105077 A1 | 4/2009 | Bhatti et al. | |
| 2009/0165166 A1 | 6/2009 | Feng et al. | |
| 2009/0208964 A1 | 8/2009 | McCarroll et al. | |
| 2010/0099859 A1 | 4/2010 | Malven et al. | |
| 2010/0122372 A1 | 5/2010 | Sebastian et al. | |
| 2012/0084879 A1 | 4/2012 | Cerny et al. | |

OTHER PUBLICATIONS

Padgette et al., "Development, Identification, and Characterization of a Glyphosate-Tolerant Soybean Line", Crop Science, 1995, pp. 1451-1461, vol. 35.
Delannay et al., "Yield Evaluation of a Glyphosate-Tolerant Soybean Line after Treatment with Glyphosate", Crop Science, 1995, 1461-1467, vol. 35.
GenBank BG406195.1, "sac38g03.y1 Gm-c1051 Glycine Max cDNA CloneGenome Systems Clone ID: Gm-c1051-4518 5-, mRNA Sequence", Jul. 22, 2004 (online), retrieved Dec. 27, 2011, Available on the Internet: <URL: http://www.ncbi.nlm.nih.gov/nucest/BG406195>.
Song et al., "A New Integrated Genetic Linkage Map of the Soybean", Theoretical and Applied Genetics, Jun. 2004, pp. 122-128, vol. 109, No. 1.
Wang et al., "Association Mapping of Iron Deficiency Chlorosis Loci in Soybean (Glycine max L. Merr.) Advance E3reeding Lines", Theoretical and Applied Genetics, Apr. 2008, pp. 777-787, vol. 116, No. 6.
GenBank BU082700.1, "saq36h09.y.1 Gm-c1045 Glycine Max cDNA Clone Soybean Clone ID: Gm-c1045-6906 5- Similar to TR:Q9SSA4 Hypothetical 46.0 KD Protein, mRNA Sequence", Jul. 2, 2004 (online), retrieved Dec. 27, 2011, Available on the Internet: <URL: http://www.ncbi.nlm.nih.gov/nucest/BUO82700>.
Shoemaker et al., "Public Soybean EST Project", Genbank [database online], 1999 [retrieved on Dec. 6, 2013], retrieved from the internet: <URL: http://www.ncbi.nlm.nih.gov/nucest/23735360?report=genbank> Acession: BU765955.
Que et al., "Trait Stacking in Transgenic Crops: Challenges and Opportunities", GM Crops, Jul.-Aug. 2010, pp. 220-229, vol. 1 No. 4.
Meyer et al., "Genetic Factors Influencing Adverse Effects of Mesotrione and Nicosulfuron on Sweet Corn Yield", Agronomy Journal, 2010, pp. 1138-1144, vol. 102, Issue 4.

(Continued)

*Primary Examiner* — David T Fox
(74) *Attorney, Agent, or Firm* — Thompson Coburn LLP; Charles P. Romano

(57) ABSTRACT

The present invention provides methods and compositions for the identification and selection of loci modulating phenotypic expression of a herbicide tolerance trait in plant breeding. In addition, methods are provided for screening germplasm entries for the performance and expression of this trait.

31 Claims, No Drawings

(56) References Cited

OTHER PUBLICATIONS

Choi et al., "A Soybean Transcript Map: Gene Distribution, Haplotype and Single-Nucleotide Polymorphism Analysis", Genetics, May 2007, pp. 685-696, vol. 176.

Grant et al., "SoyBase, the USDA-ARS soybean genetics and genomics database", Nucleic Acids Research, 2010, pp. D843-D846, vol. 38.

Hyten et al, "A High Density Integrated Genetic Linkage Map of Soybean and the Development of a 1536 Universal Soy Linkage Panel for Quantitative Trait Locus Mapping", Crop Science, May-Jun. 2010, 960-968, vol. 50.

Hyten et al., "High-throughput SNP discovery through deep resequencing of a reduced representation library to anchor and orient scaffolds in the soybean whole genome sequence", BMC Genomics, 2010, pp. 1-8, vol. 11 No. 38.

Yoon et al., "BARCSoySNP23: a panel of 23 selected SNPs for soybean cultivar identification", Theoretical and Applied Genetics, 2007, pp. 885-899, vol. 114.

* cited by examiner

SEQUENCE LISTING

```
<160> NUMBER OF SEQ ID NOS: 32

<210> SEQ ID NO 1
<211> LENGTH: 321
<212> TYPE: DNA
<213> ORGANISM: Glycine max

<400> SEQUENCE: 1
gggcttctcc gctcgaactt atgcaagggc tatgtgatgg tgatgatgat tgaatttgaa      60
gctgctactg cattactctc tttggtaatg aatttgaaga agcagaaaga aaggaaatga     120
tggtctttac accgtcaatt ttaatatwtg taagtgtaaa ctctgtagta gcacagtgat     180
gtagtgtaga ttaggcattt ggcagcgtgg taaatattct tagattgaat tgtgttatca     240
acagtattaa acgttttagg ctgaatgaat gatattgatg aatttataag gtggggaggc     300
taagatggaa tcatgtagtt a                                               321

<210> SEQ ID NO 2
<211> LENGTH: 823
<212> TYPE: DNA
<213> ORGANISM: Glycine max

<400> SEQUENCE: 2
aattacacac atcatgatct tgtaatcatc atctcccaaa tcagggatag ccttggcctt      60 cttacccccag ggattccata ccactgcact ctcattatca ccaaaccaat aagtgacatc    120
aattgtagat taaattaaca aacttatgta aatctgaatg ctggatctgg cccttataaa     180
gtgaaaaaca cgttgtagag actaaagtaa gtaatcccct tgttttttgat gaggaaatga    240 acagttgata ttatgtgcac ttgtataaca aaacatggat attttaaaat atcagtcgtt     300
gattttctca tcaataaatt aggattgttt tactctctaa agtgacttgt tcagattaga     360
agagccaaat agatacaatg ccatgcaaaa tttttattct ctgactaata actaataaca     420
acctgcatct ggcattcctt tcttctggag tacaaaagtt ctttttttct catggtctat     480
gatggcaatt ttagttgggc trtgcaagta cactctgtcc atctacaagg taaccacaaa    540
```

```
tgtccttaga gaacacttga aaaaaagtt gatttggtat ctattatata tattcataca      600
ctcgaaaatc aatcagaata tataggtt atgtgcactt atgtgcttat gatgtcaatt       660
ttcttagcct gtgagacacc tccaaccaat tgaatgaaag gaccagaaaa tcaaattata    720
cctctccatc aaaagtgagt gcatctgcct gctctgtgaa ccttgatctg ttcaacagat    780
tgtcaaagta atccagtgtc tccaatccct caatacgcac ttc                      823

<210> SEQ ID NO 3
<211> LENGTH: 385
<212> TYPE: DNA
<213> ORGANISM: Glycine max

<400> SEQUENCE: 3 attcctatt tcctacacaac actacactgt ctggtggaag aatctcttca ctctccatgc    60
aacaacgttg gctatgtctc cttattctct ctctttgtta gcctctgtct ccccaaaat    120 gcacacctt cttctttct cctcatcaca ctctccacat cttccaaacc acaacataac     180
caaatccaat aataaactct ctcattccat caatggactt tcatcmtgcc cttcttctcc   240
tttgctcccc agtgccacaa aatcttctcc cttttctcatt ccacttcaa aaattgcatc   300 tttcagggtc cttgctgctt cctctatacc tgatgctaga agtgatgaac cagccaaaac   360
tagtgatttc ttaaaaactc ttcag                                          385

<210> SEQ ID NO 4
<211> LENGTH: 1057
<212> TYPE: DNA
<213> ORGANISM: Glycine max

<400> SEQUENCE: 4
cgccagcttg catgcctgca gttccaagaa ttatttcaaa ccgctgcttc cattttagaa    60
tccttgttat gtcctttct gcacagtaga ttagtatgtc acaagttgca tgttgggccg    120
gttgatttta tgaaattaat aagagttaaa tatgtttttta gtccttgcaa ataggaaaaa   180
gttctccttt tggtcctcaa ttatgaaaat gtgtcctrta tgatcttatt tacataaatg   240
aggaaatgaa agcagatgat acttttatga aggacaaaga ttacatttga cacattttca    300
taaatgagtg actaaaaaga agcattttat ttttttagtga ttaaattaat tggaaacatt   360
acaagattac ttttggtcat gggttcaaga atccggaaac agtttctttg catatgcaag   420
ggtaatgctg cttacaatat ccctccccca taccttggca tagtgaggag cctccgggca    480
atggaataca ctagtttta tagtacaata ttttcatt agagttactg tgggacaaaa       540
ggaacttacc aaaaatgaat tgatctaagc tcttgttagg taggtactca tacacaatga    600
ggctctcagg gccttcaatg ctgcaaccca atagtttgac aaggttcttg tgttgcattc    660
cactaatcaa attcacttca ttgaagaaat catcccaccca ttgcctatta ttgaagacca   720
atctcttaac agcaacatca ttcccatttg gcagagtccc tttgtataca gaaccagatc   780
ctccttgacc tatctttctt gaagagctga aataatccgt cgccttctct agagtttcat   840
atttgtaatt caagctagaa ttcttcaagg aaggaggaac ctcaataaaa ttgttttctg    900
agtgattcag gagaaaatga aatacagcat cagcaaaatt aacaaacaat cattccaaat   960 atatatatt ggtatgaaca agagtgttct ccagaacatt acttcttctc tttttggtga   1020
aggccacata agagactgca agagtgagaa ctacaac                           1057

<210> SEQ ID NO 5
<211> LENGTH: 1304
```

```
<212> TYPE: DNA
<213> ORGANISM: Glycine max

<400> SEQUENCE: 5
acacagaaat cacaaacaag tggtgactac ttacccatat tcaccaaaga aatggaaaaa      60
cttctagaac ttgtgacaaa acaaaactgg gggactcact ctgagggcat gtcatcaaca     120
acaaccactc ctatctatgg cttggcacaa tgcttccaag acctttccag cattgattgc     180
cttcaatgct ttgcagccag ccgcaccaag ctccctcgct gcctcccttc ggtttcggct     240
cgaatttacc ttgatggctg cttccttcgc tatgacaatt acagtttcta cactgaaaac     300
tatgacccct tgagggacac agtgaattgc acctcagagt atggtctgt ggttggtgat      360 ggtgagaagt tggtgtttgc tgagagtgtt ggcaaagtgg ttgagagtgt ggtgagggtg     420
gctgtgaata taatgagggg aagaggcttt tttgcagttg agaaggtgg gggagtttat      480 gcattggcac agtgctggaa aactgttggg gtaaaagggt gtagtgattg cttgaggaaa     540
gctgaaaatg aggtcaaagg atgtttgcct aagagggaag ggagggcctt gaatactggg     600
tgctatttga gatactcaac tgttaagttc tacaatcaag gaggtcaaga tggtcaagga     660
gatggtaaga gctgttgctc tagttttgaag tttttatatt cttcattagt ttcttggttc     720
cttttggata aacttctcaa ccactagtta taggagaaaa aaatgaatta aacatctctt     780
gtaagttaaa atcaatttgt gcacttcgat aagttttata aaaactctct cgtttaactt     840
ttccaaaagc tgagatgtat aagttaattt taacttacag aagaagtttg attcattttt     900
gctttttatg ttcttctcct ttaagtattt attgagaagc ttatcggttg gaatttggaa     960
actgaagctc aactgggaat ttcaattgca tattgttacc atgcagtttc aaattccttg    1020
tgttgcttat aggttaaatg acaaatggag aaggaaagaa gtaaagatga atgttactgt    1080
atcattgtga atgaaatgct gcttttcaac tttaactttg ctataactct taggttagtt    1140
ttggtgtcta aagtttgtcc tgaatagaat cctaggtttc agttcataga tggcatagat    1200
acatgytagt catttatttt gtatacatgt tgatgcaatt gtccatgttt taattttttca   1260 gattcttcca gaaaacgagt cattatagca gcagggtcag tctt                     1304

<210> SEQ ID NO 6
<211> LENGTH: 416
<212> TYPE: DNA
<213> ORGANISM: Glycine max

<400> SEQUENCE: 6
attatatgag ggctcttggg tttttcaagg acactgatgc acccttacct gtaagaatat      60
gattttgtta ttattattat tatatttatt gtgagtctat atatataaga agaattttcc     120
attttgtttc atctaattaa tatagttta ataatttta aatttgctt tgtttaatgc        180 ttwgtttggt gttggaaatt aagattgttc cagggtttga tgctgctggt gtggtggtga     240
gagtgggaag taaagtgagc aaattcaagg ttggagatga agtttatggt gatatcattg     300
agtatgcttg gaataatcca aagaccattg ggactttggc agaatatact gctactgagg     360
agaaagtgtt ggctcacaaa ccctccaatt taagctttat tgaagcagct agcctt         416

<210> SEQ ID NO 7
<211> LENGTH: 1160
<212> TYPE: DNA
<213> ORGANISM: Glycine max

<400> SEQUENCE: 7
```

```
aggcaccaaa ccaagggatt taaaatttat taaattataa acatgaaatg attaaataaa      60
gagttgaatt cccataattt tatacgtttt attaaatttc actcagcaaa aaatgtatta     120
aaaaatatat tattcccatt tgtctgtctt tatttatgtc atctatttta attttctga     180 tgtatttaac tggggccaaa ctgaaacatg ttgatcatgc aaaggcctac tcaccatttc     240
acatgtacgt gtcatcaccc agcaacccca tttttctaca taacacacac tccctctcta     300
acactcacac tccaataaca aatatttsac tagctactac tcttcttagt ttctctgttg     360 tatcatttt  attgctatat cctaatcaaa cttcactctc aaaatgagtg atcccacact     420
agcacaacag catctagtca aagtccacac aacaacacac gaaacagttg ttaccacaca     480
caatcataac caaacaccct caataaatgt gtgttactga attatttaat tatttgtaca     540
cctaactatg attaatattt aattcttcaa actttgtttt atgcatgata accgtgatta     600 attttattt  ttttccccta tgattgagaa caggcctcag gtgaaaagaa gaagattgtg     660 gggggtgttct acaaagggaa tgaatatgct aaattgaatc caaattttgt tggatgtgtt     720
gaaggtgcat tgggaatacg tgagtggctg gaatcacagg gtcatcagta cattgtcact     780
gatgacaaag aaggacctga ttctggttag tacttagtat cttgccaact taattcaagt     840
ttgagtaaac tattatttg atgatttgat ctataaaagt gtacaacatt gtgaaattag     900
tctctaacat tgtcacatta gtctctgaaa ttaagataat ttcatatgac aaatgacatg     960
ttattaactc ttttcgtac tgtaaattga aaaatgtggc tacgtgttat atgaaaattg    1020 gttgggaccct ggtctcggat catgtaataa tttctatcaa acaaggtatc agagtaatca    1080
acactataat atcatggaat gcaaatgtgt tgtcccttc aagattttaa ttgcttgaac    1140
tcaatggaat ttgatgttct                                               1160

<210> SEQ ID NO 8
<211> LENGTH: 406
<212> TYPE: DNA
<213> ORGANISM: Glycine max

<400> SEQUENCE: 8
aggaaatact agattttgat atactattat ttaataattt tcctactcga ctaaaatgaa      60
aaaaaaaaca ctaaaataat gatatcacta atattattag ctgaattttt tttgtttgtt     120
gaatctttag ttgactgaat ttagtatttg actaaaamaa gaatcatatc acaaactaat     180
ttgcctgtaa ctcattgctt taatttgctt ttaataattg tcagcaagtc tagatttta     240 atgattagat agatagctaa caaaaatacc acactggata catatgaaat caatattaag    300
tttaaagaga tgcaatacgc aatcgatttg attaatgaat ttcaaatgtt ctgcgttaat     360
ttattcaatt accttttaaa ttgaatgttt tcattcctgg gctctg                   406

<210> SEQ ID NO 9
<211> LENGTH: 398
<212> TYPE: DNA
<213> ORGANISM: Glycine max

<400> SEQUENCE: 9
atgatgggat cttgcatatg cccgttggag actccggcga ggttgctttg gaccacaagc      60
ttcttccgtc ataagcttat gatcttctaa taattaataa ttcacgcaca caaacaaaca     120
aacaaacaaa caaaaaacac ttcataacaa caacaacaac ccttctgaaa ttctcaacac     180
aagtttcaaa aaacagagta aaagaaacag agcaaaaaca cacacacaaa aacacaaaca     240 cagacaccttt ttaagtatta aggtgtctct ttctctcscc ggaaagtttc tccgtcggcg     300
```

```
gtggtgattg accggagtgc catggagtct ggacggattt tctttggtgc ctctgcttca    360
agcggcaaca acatgctctt tctcggcaca actgaact                            398

<210> SEQ ID NO 10
<211> LENGTH: 831
<212> TYPE: DNA
<213> ORGANISM: Glycine max
<220> FEATURE:
<221> NAME/KEY: unsure
<222> LOCATION: (1)..(831)
<223> OTHER INFORMATION: unsure at all n locations

<400> SEQUENCE: 10
tagtaaagcc accaactcca acaccaactt ccccagtggt gtaccctcct cctnnntttc     60
catctccacc agctcctgta gtgaaatcaa acaagggtaa gtgtgtacca catctatstc    120
tttagtaact cctttccgat ctctaatgta attaaatgaa atgattctgt cacattttc    180 tgctaattta acttttacgt tatttagaaa aaaaatataa aagaaatttg tatcactttt    240
tctttaaaaa taggaaaaat atgtgtgata aaatagataa tgttttacaa tttcattaca    300
gaaatacttt atattttata atgttaatat ttttattt tcacaatttt tttcttcttt      360
cttattagtt tttggactta aattaaataa tatttttaat cctgtcatgt gggttttagt    420
attcttaata ttatttttctt gatttgatta ctgtaaaatg ttttagtaag cttaactaa    480 aacagacaaa gaaaatatt tcaagaagat taaaatggaa aaaagaatc ttataataca     540 tggattaaaa aattagtgaa gccttacttt tgttttctt ttctctttgt tacacgtctt    600
caccttgttg tctttgttat ccttttcac atctaatgat ggatgtgaga gaagaaccat    660
gcatggtctt aattgtttat gtgattaatg gctttaaagt atagaacttt taagtaagat    720
cagttgagtt aattaatgaa acatggtctt ttgttttcca aatttttttg tgggcagatt    780
gcattccact aagggattat aggtgctcat tacactcaag gaagaaattg t             831

<210> SEQ ID NO 11
<211> LENGTH: 520
<212> TYPE: DNA
<213> ORGANISM: Glycine max

<400> SEQUENCE: 11
atcttggttt tccaatcgcg cagcccgagc ggccatcwga acaacagtat ctacgtcaac     60
tcctttagca aaatctaca gaaaacattg aaaacacttg tgtgagcata cgacaaggca    120
aataagaaaa caacacagta caaaactgac tacttctaac ctcaataaga ttcttgtcaa    180
ctgtcagttt attcaaagtc aaagttccag ttttgtcgct acataataca tccattcctg    240
ccatctcttc tattgctgtc attcttttag taatagcacc ctgcaatgat tatataaagc    300
ataaactata aagactaaca tctaattgat taaaacttga dacaactgct tttcaagaag    360
cactaatgtc tacctgctga gctaagcgat gggatccaat tgccattgtc actgacaaaa    420
cagtaggcat ggcaatagga attcctccga taagaagcac gagcagattg tcaatcccag    480
gacgatattc ccggtgttga attgggtaca tgacaatgat                          520

<210> SEQ ID NO 12
<211> LENGTH: 337
<212> TYPE: DNA
<213> ORGANISM: Glycine max

<400> SEQUENCE: 12
```

```
ctttgattct tgccagtctt tttcattctt tttcattctt aaatccatca aatgaaccta    60
ttgatatgac tgaaaccttt ggattagcca agactaaagc tactccactt gagattttaa   120
ttaagccacg attatcttct agttgttaty tataaaagca tgtgaatctt gtcttagcgg   180
tttgtggaaa gtctgttgtt aaactatgtg atcttctttt agataaatca ggtttgcctg   240
ataaattata ttttcgtcaa aagggcattt ttggaattca caaaattgtc atcatgtggt   300
gttgaaataa ggtgtgttgt aataaggttt aaggctt                            337
```

<210> SEQ ID NO 13
<211> LENGTH: 337
<212> TYPE: DNA
<213> ORGANISM: Glycine Max

<400> SEQUENCE: 13

```
tattgtcttt tgtgaatgat caataacttc ctaatggtaa ttcctttcat tagagagccc    60
atggatttat attcccatgg tttggaaaaa agttcttcaa gcagtgtaag taacaccaat   120
ggttttactg aaaatctggt attcggtgac gcttattaac atcaatttga ccaatggttt   180
tactatggac gcttattaac atcagttaac ggtatgaagc ttgggaaagc tgttggaaaa   240
tggggtcttt gagatgcttg atgcaagttt gccatcatga cttccatttc acacttagac   300
attgagtggt gaacgtccat agtatttgat ataaatg                            337
```

<210> SEQ ID NO 14
<211> LENGTH: 616
<212> TYPE: DNA
<213> ORGANISM: Glycine Max

<400> SEQUENCE: 14

```
gcaccagtcc acacaaagaa gattgtccac agagatgtta aaacagaaaa tatgcttctg    60
gacaagacac gaaccttgaa aatagctgat tttggagtag ctcgtattga ggcctccaat   120
cctcatgaca tgcaggtgaa actggaaccc ttggttaca tggctcctga ggtacatgct   180
tcaattcctt tgaaaatttc tctctcctgt gcattgttct ttgggttt gtttcaaaca   240 cccttaatgt ctagtcctta cctcagaaaa ttttgaaaat gctggcttag gacttgttac   300
ttgcgaccgg ctctgttgtc taactaattg tgaaagaact gggttgaata ttttggact   360 taaaatataa ggaaaaatta ctaaacagga attcttgatt aaaatattaa ccatgttgga   420
aagataagga cattgaattg ttccatcact gtccttactt tcatcaggaa ttccttttgt   480
tttatagttc acccaacaat tatgtatata tccatgttgg ttttggtaca taattacagg   540
aagaaatctt tacctcagtc ccatttacaa ttactgagat ctagaactgc agcatgtcac   600
tactcactaa tcttga                                                    616
```

<210> SEQ ID NO 15
<211> LENGTH: 2174
<212> TYPE: DNA
<213> ORGANISM: Glycine Max

<400> SEQUENCE: 15

```
atggcaagca tttctagcat tccatcacac ataaaaactt gggtttattc tgaatatggg    60
aacacagaag agattctaaa atttgatccc aacgtaccta taccagacat caaggaagac   120
caggtgctca tcaaggttgt ggctacagct cttaatcctg tggattataa gagggctctt   180
ggctatttca gaacactga ctctcccctta cctgtaagat catgattta aatttatatt   240 tgcgtggatt attaattagt atagtttcca ttttgtatac caccttatat aattcttttt   300
```

```
tgtttaaata tattttagt ttttataatt tatattttt tgttttttgt tattgtaaaa      360 ttatttttt gttttgttt ttataaatta tgtttgtttt attttctttt cctaaattat      420
tttagataat gttttgaata gtaaaaaaat attataacaa taaaaaataa aataaacata      480
atttgtaaga atcaaaaata aaaataattt tgtaagtaaa aaaataaaaa ataaataaat      540
tataaggatt aaaattgtat ttaagccatt ttttttatc attgcattgt ttaatttgtg      600
tttggttttt gaaattaaga gtgttccggg gtacgatgtt gctggtgtgg tggtaagagt      660
gggaagtaaa gtgaggaaat tcaaggttgg ggatgaggtt tatggtgata tcaatgagta      720
tgctgtgaat aatccaaaga ccattgggac tttggcagag tacactgcta ctgaagagaa      780
attgttggct cacaaaccct ccaatttgag ctttattgaa gctgctagcc ttcctttagc      840
tatcatcact gcttatcaag gacttgaaag agttgatttt tctgctggaa aatctatact      900
tgttctagga ggtgctggtg gagttggatc ccttgttatt caggtttgat atcttccatc      960
tccattggtt aatttgacaa taagtttcaa ttaaacagtg tcttactgaa atattgagcc     1020
attaatttca cttttcagt attttagtta tttattttat tcttcttctc taatcatatg     1080
atttaggagc aatgatattt agatatctct ctaaatttca gacacctcat atcatatcat     1140
ttatcattta tttatatttt ctctttcctc tctatctctc ttagcataat tatataatta     1200
ataatgaatt gttgggtatt tgattgatat gatgtagctc gccaagcacg tttttggcgc     1260
atccaaggtt gcagctactg ctagttccgc aaaactggat ttattaagga acttgggagc     1320
agactttcct attgattaca caaaggagaa ttttgaagag cttgcagaga gtttgatgt      1380 agtgtacgat acaataggtc agatgttgaa attgaactta aattatttgt ttcacatgaa     1440
gtcagtttgg tcatgactaa tacaatatta acatatgaga tgtggtatga gtacaacaat     1500
tggtacagaa ctattagttt ttataccat cttacttatt tatgacatgt aataaataat      1560
gtacaccaga gatattaaca caaagaatg ttgttataca attaatttaa agtgcattaa       1620
catgtaacat acaacttatt actttgtta tcttattatt gattaccatg tgtaataaga      1680
ttgttgataa taataaatta ctttaagaat tgttatctat ttttttatt agtggatagt      1740 ataaaagtat tttcatgtgt atcaatatta ttattgaaaa tgaagacatg gttgattcca     1800
aaaacagggc agagtgacaa ggcattgaag gctatcaaag aaggggggaa agttgtgaca     1860
atagcaccac cagcaactcc acctgctatc ccattctttc tcacttcaga tggtgctgtg     1920
ttggagaagt tacaacctca cttagaaagt gggaaggtga agccagtatt ggatcctaag     1980 agtcccttc cattttctca gattgtgaa gcatattcat acttgaagac aaatagagcc       2040
attgggaaag tagtcataca tcccatccct tgaacatata taactatgca aatatactat     2100
caagtcctgc tgtgcattct gaccttaatt tgtgttaata aggttaatat ttatatgatt     2160
gataaggaga gagc                                                      2174
```

<210> SEQ ID NO 16
<211> LENGTH: 384
<212> TYPE: DNA
<213> ORGANISM: Glycine Max
<220> FEATURE:
<221> NAME/KEY: unsure
<222> LOCATION: (1)..(384)
<223> OTHER INFORMATION: unsure at all n locations

<400> SEQUENCE: 16

```
tttagtcatt agaatttac ttgtttactc ggttcgaaag ttccatctcg ctggtctcaa       60
```

```
ttactattaa aaaatctcat attgcttacc tcaattagtg ggatgaggtt taagtacgtg    120
atgaacaact tcacttnntg ctaattagtt tgaagttata atgtaacatg ctctatcctt    180 cttttggtt  ggttgcttgg ggggagctcc cnnnnacatg gaattattgg gaatcaagct    240
tccataattg tttcttcact tcttgatggc ctaattaagc tgcatgtgct agagaactca    300
gaggggctgt aggacacacc aatcttctta aatgtgtttg atgaggagct gtctatgcta    360
aaacctaatg gagatgtttg atct                                          384
```

```
<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
ttctcctttt ggtcctcaat tatga                                          25
```

```
<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
catctgcttt catttcctca tttatg                                         26
```

```
<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
tgtgtcctat atgatctt                                                  18
```

```
<210> SEQ ID NO 20
<211> LENGTH: 17
<212> TYPE: DNA
<213> ORGANISM: Artificial Sequence
<220> FEATURE:
<223> OTHER INFORMATION: Synthetic

<400> SEQUENCE: 20
tgtcctgtat gatctta                                                   17
```

```
<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
atcctaggtt tcagttcata gatggc                                         26
```

```
<210> SEQ ID NO 22
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 22
ggacaattgc atcaacatgt atacaa                                        26

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
atgactaaca tgtatctat                                                19

<210> SEQ ID NO 24
<211> LENGTH: 18
<212> TYPE: DNA
<213> ORGANISM: Artificial Sequence
<220> FEATURE:
<223> OTHER INFORMATION: Synthetic

<400> SEQUENCE: 24
tgactagcat gtatctat                                                 18

<210> SEQ ID NO 25
<211> LENGTH: 28
<212> TYPE: DNA
<213> ORGANISM: Artificial Sequence
<220> FEATURE:
<223> OTHER INFORMATION: Synthetic

<400> SEQUENCE: 25
aagaagaatt ttccattttg tttcatct                                      28

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gcatcaaacc ctggaacaat ct                                            22

<210> SEQ ID NO 27
<211> LENGTH: 14
<212> TYPE: DNA
<213> ORGANISM: Artificial Sequence
<220> FEATURE:
<223> OTHER INFORMATION: Synthetic

<400> SEQUENCE: 27
ccaacaccaa acta                                                     14

<210> SEQ ID NO 28
<211> LENGTH: 14
<212> TYPE: DNA
<213> ORGANISM: Artificial Sequence
<220> FEATURE:
<223> OTHER INFORMATION: Synthetic

<400> SEQUENCE: 28
caacaccaaa caaa                                                     14

<210> SEQ ID NO 29
```

```
<211> LENGTH: 26
<212> TYPE: DNA
<213> ORGANISM: Artificial Sequence
<220> FEATURE:
<223> OTHER INFORMATION: Synthetic

<400> SEQUENCE: 29
aaccccattt ttctacataa cacaca                                              26

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
caataaaaat gatacaacag agaaactaag aa                                       32

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
agtagtagct agtgaaata                                                      19

<210> SEQ ID NO 32
<211> LENGTH: 16
<212> TYPE: DNA
<213> ORGANISM: Artificial Sequence
<220> FEATURE:
<223> OTHER INFORMATION: Synthetic

<400> SEQUENCE: 32
agctagtcaa atattt                                                         16
```

US 8,921,647 B2

MOLECULAR MARKERS ASSOCIATED WITH YELLOW FLASH IN GLYPHOSATE TOLERANT SOYBEANS

CROSS-REFERENCE TO RELATED APPLICATIONS

This application claims the benefit of U.S. Provisional Application Ser. No. 61/380,024, filed Sep. 3, 2010 and incorporated herein by reference in its entirety.

INCORPORATION OF SEQUENCE LISTING

A sequence listing containing the file named "46_21_54534.txt" which is 19,743 bytes (measured in MS-Windows®) and created on Aug. 30, 2010, comprises 32 nucleotide sequences, is provided herewith via the USPTO's EFS system and is herein incorporated by reference in its entirety. Also incorporated herein by reference are the 32 nucleotide sequences and pertinent identifying information in the Sequence Listing containing the file named "46_21_54534.txt" which is 18477 bytes (measured in MS-Windows®), created on Aug. 30, 2010, and filed with U.S. Provisional Application Ser. No. 61/380,024 on Sep. 3, 2010.

Incorporation of Table 2

A listing of various soybean linkage group L (chromosome 19) markers is provided herewith in the Specification as Table 2. Also incorporated herein by reference is the listing of various soybean linkage group L (chromosome 19) markers that was provided in the document "Appendix to the Specification as Table 2" that was 4541064 bytes (as measured in MS-Windows®), filed with U.S. Provisional Application Ser. No. 61/380,024 on Sep. 3, 2010. Table 2 appears in the final pages of the specification.

BACKGROUND OF INVENTION

"Yellow Flash" is an undesirable phenotype observed in certain soybean varieties that comprise a transgene that confers tolerance to the broad-spectrum herbicide glyphosate. After application of glyphosate, or applications of glyphosate under certain environmental conditions such as high temperature, the leaves of certain soybean plant varieties comprising the transgene that confers glyphosate tolerance can exhibit a yellowish color (hence, the term "Yellow Flash"). The Yellow Flash phenotype can be observed approximately a week after herbicide application in certain soybean varieties comprising the transgene that confers glyphosate tolerance. The yellow flash phenotype is undesirable as it leads to a visually displeasing off-type yellow leaf color in soybean plants exposed to glyphosate.

SUMMARY OF INVENTION

Although the Yellow Flash phenotype can be observed approximately a week after herbicide application in certain soybean varieties comprising the transgene that confers glyphosate tolerance, distinct soybean varieties that comprise the same glyphosate tolerant transgene integrated at the same chromosomal locus (i.e. the same transgenic event) can show various degrees of yellow flash upon exposure to high doses of glyphosate. Some varieties comprising the glyphosate tolerant transgene insertion are highly resistance to high dosages of glyphosate, showing no yellow flash phenotype (i.e. a "no flash phenotype"), while other varieties comprising the same glyphosate tolerant transgene insertion are highly susceptible to high dosages of glyphosate, showing a severe yellow flash phenotype. Provided herein are soybean plants comprising an introgressed genomic region associated with a no flash phenotype. Also provided herein are markers that reside outside of a genomic region associated with a no flash phenotype and that facilitate breeding activities that include, but are not limited to, introgression of this genomic region. Markers and specific alleles thereof that are associated with a no flash phenotype are also provided. Methods of obtaining a soybean plant that exhibits a no flash phenotype and methods of obtaining a soybean plant comprising in its genome at least one no flash locus are also provided. Methods that provide for the introgression of a genomic region associated with a no flash phenotype into soybean germplasm that has a genomic region associated with a yellow flash phenotype. Identification of molecular markers associated with loci that confer the no flash phenotype has significant economic value. By using markers associated with the no flash trait, breeders can select soybean varieties with the favorable alleles (i.e. alleles that are not associated with the yellow flash trait) for use in trait integration. They can also use the markers to help them eliminate unfavorable alleles (i.e. alleles that are associated with the yellow flash trait) in soybean unfavorable allele. This invention thus provides for commercially desirable transgenic soybean lines that carry a genomic region that is associated with a "no flash" phenotype and tolerate high dosages of glyphosate.

Methods of identifying a soybean plant that comprises a genotype associated with a no flash phenotype are thus provided. In certain embodiments, methods of identifying a soybean plant that comprises a genotype associated with a no flash phenotype, comprising: detecting in the soybean plant an allele in at least one yellow flash marker locus associated with the no flash phenotype wherein the yellow flash marker locus is in a linkage group L genomic region flanked by loci BG406195 (SEQ ID NO: 13) and BU082700 (SEQ ID NO:14), and denoting that the plant comprises a genotype associated with a no flash phenotype. In certain embodiments, the methods further comprise the step of selecting the denoted plant from a population of plants. In certain embodiments of any of the aforementioned methods, the denoted plant comprises a transgene that confers tolerance to glyphosate are provided. In certain embodiments where the denoted plant comprises a transgene that confers tolerance to glyphosate, the soybean plant or progeny thereof is exposed to a dosage of glyphosate sufficient to cause yellow flash in a susceptible variety. In certain embodiments of the aforementioned methods, a plant that exhibits a no flash phenotype is selected. In certain embodiments of the aforementioned methods, the genotype associated with a no flash phenotype comprises at least one polymorphic allele of at least one marker in a first sub-region of the linkage group L region that is flanked by loci BG406195 (SEQ ID NO: 13) and BU551345 (SEQ ID NO: 16) and/or at least one polymorphic allele of at least one marker in a second sub-region of the linkage group L region that is flanked by loci TA14086_34305 (SEQ ID NO: 15) and BU082700 (SEQ ID NO: 14). In certain embodiments of the aforementioned methods, the genotype associated with a no flash phenotype comprises at least one polymorphic allele of at least one marker in the linkage group L region selected from the group consisting of M0129138 (SEQ ID NO:4), M0101742 (SEQ ID NO:5), M0093116 (SEQ ID NO:6), and M0129925 (SEQ ID NO:7) that is associated with a no flash phenotype.

Also provided are methods for obtaining a soybean plant comprising in its genome at least one no flash locus. In certain embodiments, a method for obtaining a soybean plant comprising in its genome at least one no flash locus, comprising the steps of: a. genotyping a plurality of soybean plants with respect to at least one yellow flash locus in a first linkage group L genomic region flanked by loci BG406195 (SEQ ID NO: 13) and BU082700 (SEQ ID NO:14); and, b. selecting a soybean plant comprising in its genome at least one no flash locus comprising a genotype associated with no flash phenotype are provided. In certain embodiments of these methods, the genotype associated with a no flash phenotype comprises at least one polymorphic allele of at least one marker in a first sub-region of the linkage group L region that is flanked by loci BG406195 (SEQ ID NO: 13) and BU551345 (SEQ ID NO: 16); and/or at least one polymorphic allele of at least one marker in a second sub-region of the linkage group L region that is flanked by loci TA14086_34305 (SEQ ID NO: 15) and BU082700 (SEQ ID NO: 14). In certain embodiments of the aforementioned methods, the genotype associated with a no flash phenotype comprises at least one polymorphic allele of at least one marker in the first linkage group L region, the first sub-region, or the second sub-region, wherein the marker is selected from the group consisting of M0129138 (SEQ ID NO:4), M0101742 (SEQ ID NO:5), M0093116 (SEQ ID NO:6), and M0129925 (SEQ ID NO:7). In certain embodiments, the plurality of soybean plants comprises a population that is obtained by: i) crossing a parent plant comprising at least one no flash locus with a parent plant comprising at least one yellow flash locus; or, ii) obtaining seed or progeny from a parental plant segregating for at least one no flash locus. In certain embodiments, the population contains plants that comprise a transgene that confers tolerance to glyphosate. In certain embodiments, the aforementioned methods can further comprise the step of assaying for the presence of at least one additional marker, wherein the additional marker is either linked or unlinked to the linkage group L genomic region. In certain embodiments of the aforementioned methods, the plurality of soybean plants, the soybean plant, and/or progeny thereof are exposed to a dosage of glyphosate sufficient to cause yellow flash in a susceptible variety. In certain embodiments of the aforementioned methods, a plant that exhibits a no flash phenotype is selected.

Also provided herewith are methods for producing a soybean plant comprising in its genome at least one introgressed no flash locus. In certain embodiments, a method for producing a soybean plant comprising in its genome at least one introgressed no flash locus comprising the steps of: a. crossing a first no flash soybean plant with a second soybean plant comprising: a yellow flash locus in a first linkage group L genomic region flanked by loci BG406195 (SEQ ID NO: 13) and BU082700 (SEQ ID NO: 14), and at least one linked polymorphic locus not present in the first no flash soybean plant to obtain a population segregating for the no flash loci and the linked polymorphic locus; b. detecting at least two polymorphic nucleic acids in at least one soybean plant from the population, wherein at least one of the polymorphic nucleic acids is located in the first linkage group L region and wherein at least one of the polymorphic amino acids is a linked polymorphic locus not present in the first no flash soybean plant; and c. selecting a soybean plant comprising a genotype associated with a no flash phenotype and at least one linked marker found in the second soybean plant comprising a yellow flash locus but not in the first no flash soybean plant, thereby obtaining a soybean plant comprising in its genome at least one introgressed no flash locus are provided. In certain embodiments of the methods, at least one of the first or the second soybean plants comprises a transgene that confers tolerance to glyphosate. In certain embodiments of the methods, the population, the selected soybean plant, and/or progeny of selected soybean plant is exposed to a dosage of glyphosate sufficient to cause yellow flash in a susceptible variety. In certain embodiments, the yellow flash locus comprises at least one polymorphic allele of at least one marker in a first sub-region of the linkage group L region that is flanked by loci BG406195 (SEQ ID NO: 13) and BU551345 (SEQ ID NO: 16); and/or at least one polymorphic allele of at least one marker in a second sub-region of the linkage group L region that is flanked by loci TA14086_34305 (SEQ ID NO: 15) and BU082700 (SEQ ID NO: 14). In certain embodiments of the aforementioned methods, the polymorphic nucleic acid detected in step (b) is detected with at least one marker selected from the group consisting of M0129138 (SEQ ID NO:4), M0101742 (SEQ ID NO:5), M0093116 (SEQ ID NO:6), and M0129925 (SEQ ID NO:7). In certain embodiments of the aforementioned methods, the polymorphic nucleic acid detected in step (b) is detected with at least one marker selected from the group consisting of M0101742 (SEQ ID NO:5) and M0129925 (SEQ ID NO:7). In certain embodiments of the aforementioned methods, the polymorphic nucleic acids are detected with marker M0101742 (SEQ ID NO:5) and with marker M0129925 (SEQ ID NO:7). In certain embodiments of the aforementioned methods, the linked polymorphic locus is detected with a genotypic marker, a phenotypic marker, or both. In certain embodiments of the methods, the linked polymorphic locus is detected with a marker that is located within about 1000, 500, 100, 40, 20, 10, or 5 kilobases (Kb) of the no flash locus. In certain embodiments of the methods, the linked polymorphic locus is detected with at least one marker selected from the group consisting of M0205928 (SEQ ID NO:3), M0205537 (SEQ ID NO:8), M0202715 (SEQ ID NO:9), M0206286 (SEQ ID NO:10), M0206054 (SEQ ID NO:11) and M0205375 (SEQ ID NO:12). Also provided herewith are soybean plants comprising an introgressed no flash locus made by the aforementioned methods. In certain embodiments, a soybean plant comprising an introgressed no flash locus and one or more polymorphic loci comprising alleles or combinations of alleles that are not found in a no flash soybean variety and that are linked to the introgressed no flash locus, wherein the plant is produced by the aforementioned methods are provided.

Also provided are soybean plants comprising an introgressed no flash locus and one or more polymorphic loci comprising alleles or combinations of alleles that are not found in a no flash soybean variety and that are linked to the introgressed no flash locus.

Also provided are substantially purified nucleic acid molecules comprising a nucleic acid molecule selected from the group consisting of M0129138 (SEQ ID NO:4), M0101742 (SEQ ID NO:5), M0093116 (SEQ ID NO:6), and M0129925 (SEQ ID NO:7), or a fragment thereof that contains a specific allelic variant of M0129138 (SEQ ID NO:4), M0101742 (SEQ ID NO:5), M0093116 (SEQ ID NO:6), or M0129925 (SEQ ID NO:7). In certain embodiments, the fragment that contains the allelic variant is at least 15, at least 18, at least 20, at least 22, at least 25, or at least 30 nucleotides in length.

In certain embodiments, methods for obtaining a soybean plant that exhibits a no flash phenotype comprising the steps of: a) crossing a soybean plant that exhibits a no flash phenotype with a soybean plant that exhibits a yellow flash phenotype, wherein at least one of the soybean plants comprises a transgene that confers tolerance to glyphosate, and b) selecting a progeny plant from the cross, wherein the progeny plant comprises the transgene that confers glyphosate tolerance and wherein the progeny plant exhibits a no flash phenotype are provided. In certain embodiments of the methods, the selection in step b can comprise: i) genotyping the progeny plant with respect to a yellow flash locus in a linkage group L genomic region flanked by loci BG406195 (SEQ ID NO: 13) and BU082700 (SEQ ID NO: 14); and/or ii) exposing the progeny plant to glyphosate and scoring the plant for a no flash phenotype. In certain embodiments of the methods, a soybean plant that exhibits a yellow flash phenotype comprises at least one linked or unlinked marker not present in the first no flash soybean plant. In certain embodiments, the progeny plant is further selected for the presence of the linked or unlinked marker.

Also provided are methods of breeding soybean plants comprising the steps of: a. selecting a first soybean plant comprising a genotype in the linkage group L genomic region flanked by loci BG406195 (SEQ ID NO: 13) and BU082700 (SEQ ID NO: 14) that is associated with a no flash phenotype from a population of soybean plants that is segregating for the genotype; and, b) crossing the selected soybean plant with a second soybean plant. In certain embodiments of these methods, one or both of the soybean plants comprises a transgene that confers glyphosate tolerance.

Further areas of applicability will become apparent from the description provided herein. It should be understood that the description and specific examples are intended for purposes of illustration only and are not intended to limit the scope of the present disclosure.

DETAILED DESCRIPTION OF INVENTION

I. Definition

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "denoting" when used in reference to a plant genotype refers to any method whereby a plant is indicated to have a certain genotype. Such indications of a certain genotype include, but are not limited to, any method where a plant is physically marked or tagged. Physical markings or tags that can be used include, but not limited to, a barcode, a radio-frequency identification (RFID), a label or the like. Indications of a certain genotype also include, but are not limited to, any entry into any type of written or electronic database whereby the plant's genotype is provided.

A "locus" is a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group L" corresponds to the soybean linkage group L described in Choi, et al., Genetics. 2007 May; 176(1): 685-696. Linkage group L, as used herein, also corresponds to soybean chromosome 19 (as described on the World Wide Web at soybase.org/LG2Xsome.php). As used herein, "polymorphism" means the presence of one or more variations of a nucleic acid sequence at one or more loci in a population of at least two members. The variation can comprise but is not limited to one or more nucleotide base substitutions, the insertion of one or more nucleotides, a nucleotide sequence inversion, and/or the deletion of one or more nucleotides.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, "marker" means a detectable characteristic that can be used to discriminate between organisms. Examples of such characteristics include, but are not limited to, genetic markers, biochemical markers, fermentation yield, fermentation efficiency, energy yield, secondary compounds, metabolites, morphological characteristics, and agronomic characteristics.

As used herein, "marker assay" means a method for detecting a polymorphism at a particular locus using a particular method. Marker assays thus include, but are not limited to, measurement of at least one phenotype (such as seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "genotype" means the genetic component of the phenotype and it can be indirectly characterized using markers or directly characterized by nucleic acid sequencing.

As used herein, the term "introgressed", when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a yellow flash locus with a corresponding no flash locus or by conversion of a locus from a yellow flash genotype to a no flash genotype.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, the termed "linked", when used in the context of markers and/or genomic regions, means that the markers and/or genomic regions are located on the same linkage group or chromosome.

As used herein, a "nucleic acid molecule," be it a naturally occurring molecule or otherwise may be "substantially purified", if desired, referring to a molecule separated from substantially all other molecules normally associated with it in its native state. More preferably, a substantially purified molecule is the predominant species present in a preparation. A substantially purified molecule may be at least about 60% free, preferably at least about 75% free, more preferably at least about 90% free, and most preferably at least about 95% free from the other molecules (exclusive of solvent) present in the natural mixture. The term "substantially purified" is not intended to encompass molecules present in their native state.

As used herein, "quantitative trait locus (QTL)" means a locus that controls to some degree numerically representable traits that are usually continuously distributed. As used herein, the term "transgene" means nucleic acid molecules in the form of DNA, such as cDNA or genomic DNA, and RNA, such as mRNA or microRNA, which may be single or double stranded.

As used herein, the term "event", when used in the context of describing a transgenic plant, refers to a particular transformed plant line. In a typical transgenic breeding program, a transformation construct responsible for a trait is introduced into the genome via a transformation method. Numerous independent transformants (events) are usually generated for each construct. These events are evaluated to select those with superior performance.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. *max* or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. *max, Glycine max* ssp. *Formosana*, and/or *Glycine soja* can be genotyped using compositions and methods provided herein.

As used herein, the term "bulk" refers to a method of managing a segregating population during inbreeding that involves growing the population in a bulk plot, harvesting the self pollinated seed of plants in bulk, and using a sample of the bulk to plant the next generation As used herein, the phrase "Single Plant Selection" (or the acronym "SPS") refers to a method that is often used instead of bulk method (see immediately above) to advance segregating germplasm in early generations. SPS is always used to advance germplasm to "Progeny Row" (Prow) and "Progeny Row Yield Trial" (PRYT) analyses.

As used herein, the phrase "Progeny Row" (Prow) refers to a plant breeding and analysis method where a row of progeny plants from SPS is grown for observation, further selection, and/or bulking As used herein, the phrase "Progeny Row Yield Trial" (PRYT) refers to a plant breeding and analysis method where a row of plants from a SPS is grown in a small yield trial with other SPS material. In most instances, the PRYT is usually from the same population and usually consists of one rep at one location.

As used herein, the term "comprising" means "including but not limited to".

II. Description of the Invention

Overview

In accordance with the present invention, Applicants have discovered genomic regions, associated markers, and associated methods for identifying and associating genotypes that effect a transgene-mediated glyphosate tolerance trait. For example, in one embodiment, a method of the invention comprises screening a plurality of transgenic germplasm entries displaying a heritable variation for at least one transgene mediated glyphosate tolerance trait wherein the heritable variation is linked to at least one genotype; and associating at least one genotype from the transgenic germplasm entries to at least one transgene mediated glyphosate tolerance trait. In another embodiment, a method of the invention comprises crossing at least two germplasm entries with a test germplasm entry for the evaluation of performance of at least one transgene mediated glyphosate tolerance trait in order to determine preferred crossing schemes. The methods of the present invention can be used with traditional breeding techniques as described below to more efficiently screen and identify genotypes affecting a transgene-mediated glyphosate tolerance trait.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (US Patent Application 2005/0015827). In this case, costly, time-intensive phenotyping assays required for determining if a plant or plants contains a genomic region associated with a "no flash" or "yellow flash" phenotype can be supplanted by genotypic assays that provide for identification of a plant or plants that contain the desired genomic region.

III. A Genomic Region Associated with a No Flash Phenotype

Provided herewith is a soybean genomic region that is shown herein to be associated with a desirable no flash phenotype when present in certain allelic forms and when combined with certain transgenic loci that confer glyphosate tolerance.

A soybean genomic region provided that can be associated with a desirable no flash phenotype when present in certain allelic forms is located on the telomere proximal end of the short arm of soybean linkage group L (chromosome 19). A series of markers useful in practicing the methods of this invention are provided herewith in Table 1. Additional markers useful in the practice of the invention are provided herewith in Table 2 of the Specification, which is incorporated herewith by reference in its entirety. Table 2 provides the Table 1 markers, additional nucleic acid markers or loci that have been disclosed in various databases, the relative positions of the markers on a physical map of linkage group L (soybean chromosome 19), and sources for the markers.

TABLE 1

Markers spanning a genomic region associated with a desirable no flash phenotype

| Marker or Locus Name | SEQ ID NO: | Map Position[1] | Allelic form(s) Associated with No Flash Phenotype[2] |
|---|---|---|---|
| M0205350 | 1 | 423935 | |
| M0114388 | 2 | 380897 | |
| M0205928 | 3 | 92526 | |
| M0129138[3] | 4 | 114013 | GG[7] or AA[8] |
| M0101742[4] | 5 | 112836 | TT[7] or CC[8] |
| M0093116[5] | 6 | 805580 | AA[7] or TT[8] |

TABLE 1-continued

Markers spanning a genomic region associated with a desirable no flash phenotype

| Marker or Locus Name | SEQ ID NO: | Map Position[1] | Allelic form(s) Associated with No Flash Phenotype[2] |
|---|---|---|---|
| M0129925[6] | 7 | 831128 | CC[7] or GG[7,8] |
| M0205537 | 8 | 890254 | |
| M0202715 | 9 | 921431 | |
| M0206286 | 10 | 1209977 | |
| M0206054 | 11 | 1465354 | |
| M0205375 | 12 | 2009800 | |
| BG406195 | 13 | 107207 | |
| BU082700 | 14 | 864145 | |

[1]The relative positions of the middle position of the listed markers or loci based on nucleotide positions on a physical map of soybean linkage group L (chromosome 19) of Table 2 are provided where nucleotide position 0 (zero) is telomere proximal and nucleotide position 2009800 is centromere proximal. Polymorphic nucleotide bases are designated in the sequence listing provided herewith according to the WIPO Standard ST.25 (1998), Table 1, as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2]Both the maternal and paternal alleles of the single nucleotide polymorphisms that can be associated with a non flash phenotype are shown.
[3]The identified polymorphic allele of marker M0129138 is located at nucleotide 218 of SEQ ID NO: 4.
[4]The identified polymorphic allele of marker M0101742 is located at nucleotide 1206 of SEQ ID NO: 5.
[5]The identified polymorphic allele of marker M0093116 is located at nucleotide 183 of SEQ ID NO: 6.
[6]The identified polymorphic allele of marker M0129925 is located at nucleotide 328 of SEQ ID NO: 7.
[7]The identified polymorphic allele of marker M0129138 "GG" can be associated with a no flash phenotype when the identified polymorphic alleles of the other markers are: "TT" for M0101742, "AA" for marker M0093116, and either "GG" or "CC" for marker M0129925.
[8]The identified polymorphic allele of marker M0129138 "AA" can be associated with a no flash phenotype when the identified polymorphic alleles of the other markers are: "CC" for M0101742, "TT" for marker M0093116, and "GG" for marker M0129925.

Also provided herein are sub-regions of the linkage group L region that is flanked by loci BG406195 (SEQ ID NO: 13) and BU082700 (SEQ ID: 14) that are associated with a no flash phenotype. A first sub-region of the linkage group L region associated with a no flash phenotype is flanked by loci BG406195 (SEQ ID NO: 13) and BU551345 (SEQ ID NO: 16). These loci flank a first sub-region that spans telomere proximal nucleotide 107039 to centromere proximal nucleotide 115956 in the physical map of linkage group L provided in Table 2 of the specification. Polymorphisms located in this first sub-region that are associated with a no flash phenotype can be detected with markers that include, but are not limited to, M0129138 (SEQ ID NO: 4) and M0101742 (SEQ ID NO: 5). A second sub-region of the linkage group L region associated with a no flash phenotype is flanked by loci TA14086_34305 (SEQ ID NO: 15) and BU082700 (SEQ ID NO: 14). These loci flank the second sub-region that spans telomere proximal nucleotide 800932 to centromere proximal nucleotide 864449 in the physical map of linkage group L provided in Table 2 of the specification. Polymorphisms located in this second sub-region that are associated with a no flash phenotype can be detected with markers that include, but are not limited to, M0093116 (SEQ ID NO: 6), and M0129925 (SEQ ID NO: 7). In certain embodiments of invention, a polymorphism associated with a no-flash phenotype is detected in only one of these sub-regions. In other embodiments of the invention, at least one polymorphism associated with a no-flash phenotype is detected in both of these sub-regions. Thus, one or more markers selected from the group consisting of M0129138 (SEQ ID NO: 4), M0101742 (SEQ ID NO: 5), and markers located between loci BG406195 (SEQ ID NO: 13) and BU551345 (SEQ ID NO: 16) can be used either independently of, or in combination with, one or more markers selected from the group consisting of M0093116 (SEQ ID NO: 6), and M0129925 (SEQ ID NO: 7), and markers located between loci TA14086_34305 (SEQ ID NO: 15) and BU082700 (SEQ ID NO: 14) to detect polymorphisms associated with a no flash phenotype. Conversely, one or more markers selected from the group consisting of M0093116 (SEQ ID NO:6), and M0129925 (SEQ ID NO:7), and markers located between loci TA14086_34305 (SEQ ID NO: 15) and BU082700 (SEQ ID NO: 14) can also be used independently of, or in combination with, any markers located in the first sub-region to detect polymorphisms associated with a no flash phenotype. In certain embodiments, a polymorphism in the first sub-region is detected with marker M0101742 (SEQ ID NO: 5) and a polymorphism in the second sub-region is detected with marker M0129925 (SEQ ID NO: 7).

Additional genetic markers can be used either in conjunction with the markers provided in Table 1 and/or Table 2 or independently of the markers provided in Table 1 and/or Table 2 to practice the methods of the instant invention. Publicly available marker databases from which useful markers can be obtained include, but are not limited to, the soybase-.org website on the internet (World Wide Web) that is administered by the United States Agricultural Research Service, the United States Department of Agriculture, and Iowa State University. Additional soybean markers that can be used and that have been described in the literature include, but are not limited to, Hyten et al., BMC Genomics. 11:38, 2010; Choi et al., Genetics. 176(1):685-96, 2007; Yoon et al., Theor Appl Genet. 2007 March; 114(5):885-99; and Hyten et al. Crop Sci. 2010 50: 960-968. Given the provision herein of a genomic region on linkage group L (chromosome 19) delimited or flanked by the telomere proximal locus BG406195 (SEQ ID NO: 13) of Table 2 and the centromere proximal locus BU082700 (SEQ ID NO: 14) of Table 2 as well as an assortment of soybean germplasms exhibiting either a "yellow-flash" or "no flash" phenotype, additional markers located either within or near this genomic region that are associated with these phenotypes can be obtained by merely typing the new markers in the various germplasms provided herewith. The genomic region on linkage group L (chromosome 19) delimited or flanked by the telomere proximal locus BG406195 (SEQ ID NO: 13) of Table 2 and the centromere proximal locus BU082700 (SEQ ID NO: 14) of Table 2 can also be mapped relative to markers provided in any publicly available or other soybean physical or genetic map to place this genetic locus on that map.

IV. Identification of Plants Exhibiting the "Flash" or "No-Flash" Phenotype

To observe the presence or absence of the "Yellow Flash" or no flash phenotypes, transgenic soybean plants comprising a transgene that confers glyphosate tolerance are typically exposed in early to mid-vegetative growth stages to one or more high doses of glyphosate. Typical doses of glyphosate that can elicit a yellow flash phenotype can range from about a 2-fold label application rate of a commercially available glyphosate formulation to about a 3-fold label application rate of a commercially available glyphosate formulation. In terms of acid equivalents of glyphosate acid applied, typical doses of glyphosate that can elicit a yellow flash phenotype can range from an application rate of about 1.5 pounds of acid equivalent per acre (about 1.68 kilograms per hectare) of glyphosate acid to about 2.25 pounds of acid equivalent per acre (i.e. about 2.52 kilograms per hectare) of glyphosate acid when the indicated amounts of glyphosate acid are provided in either a commercially available glyphosate formulation or when the indicated amounts of glyphosate acid is provided in a similar formulation suitable for application to glyphosate-tolerant crops. Commercially available glyphosate formulations that can be used include, but are not limited to, ROUNDUP ORIGINAL MAX®, ROUNDUP POWERMAX®, ROUNDUP ULTRAMAX®, or ROUNDUP WEATHERMAX® (Monsanto Co., St. Louis, Mo., USA); TOUCHDOWN IQ® or TOUCHDOWN TOTAL® (Syngenta, Wilmington, Del., USA); GLYPHOMAX®, GLYPHOMAX PLUS®, or GLYPHOMAX XRT® (Dow Agrosciences LLC, Indianapolis, Ind., USA) glyphosate formulations. In certain embodiments, the commercially available glyphosate formulation used is ROUNDUP WEATHERMAX®. In certain embodiments, doses of glyphosate that can elicit a yellow flash phenotype can range from about a 2 fold application rate of about 42.6 ounces per acre ROUNDUP WEATHERMAX® (1.68 kilograms per hectare) to about a three fold application rate of about 63.9 ounces per acre ROUNDUP WEATHERMAX® (i.e. about 2.52 kilograms per hectare) glyphosate formulation.

The Yellow Flash phenotype can be observed approximately a week after herbicide application in certain soybean varieties comprising the transgene that confers glyphosate tolerance. Glyphosate is typically applied during vegetative growth stages. In certain embodiments of these methods, glyphosate can be applied in weekly intervals (i.e. once a week) for any of 2, 3, 4 or more successive weeks to score for the presence of the yellow flash phenotype. In certain embodiments, soybean plants at about the V3-V4 vegetative development stage are exposed to an initial glyphosate spray followed by three subsequent sprays at weekly intervals. The first spray can be based on stage of growth and remaining sprays were scheduled at 7 day intervals following initial spray. As discussed herein, the vegetative stages of soybean are as follows: VE (emergence), VC (cotyledon stage), V1 (first trifoliolate leaf), V2 (second trifoliolate leaf), V3 (third trifoliolate leaf), V(n) (nth trifoliolate leaf), and V6 (flowering will soon start). A description of the soybean vegetative stages can be found on the world wide web (internet) at ag.ndsu.edu/pubs/plantsci/rowcrops/a1174/a1174w.htm (North Dakota State University publication A-1174, June 1999, Reviewed and Reprinted August 2004). Expression of the yellow flash trait can also be influenced by temperature, where the trait in varieties that display the yellow flash phenotype is more pronounced following treatment at temperatures of about 32 degrees Celsius or more.

A rating scale that evaluates the degree of yellow flash can also be employed to identify "flash" and "no flash" plants. An exemplary and non limiting scale for evaluating the yellow flash phenotype is as follows, where the low numbers correspond to a "no flash" phenotype and the high numbers correlate to a "flash" phenotype:
1: Green—No Yellowing
2: Mostly green, very slight yellowing <5% (1-2 plants with some yellowing)
3: 5-10% plants with yellowing
4: 11-20% plants with yellowing
5: 21-35% plants with yellowing
6: 36-50% plants with yellowing
7: 51-65% plants with yellowing
8: 66-80% plants with yellowing, some necrosis
9: 81-100% plants with yellowing and or necrosis

V. Introgression of a Genomic Region Associated with a No Flash Phenotype

Also provided herewith are unique soybean germplasm comprising an introgressed genomic region that is associated with a no flash phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (i.e. such as a no flash germplasm) and both linked and unlinked markers characteristic of the desired genetic background of a second germplasm (i.e. a yellow flash germplasm). In addition to the markers provided herewith that identify alleles of genomic region that is associated with a no flash phenotype, flanking markers that fall on both the telomere proximal end of the genomic region on linkage group L (chromosome 19) and the centromere proximal end of the linkage group L (chromosome 19) genomic region are also provided in Tables 1 and 2. Such flanking markers are useful in a variety of breeding efforts that include, but are not limited to, introgression of the genomic region associated with a no flash phenotype into a genetic background comprising markers associated with germplasm that ordinarily contains the allelic forms of the genomic region that is associated with a "yellow flash" phenotype. Telomere proximal flanking markers that can be used in these methods include, but are not limited to, M0205928 (SEQ ID NO: 3) and/or polymorphisms in any of the loci listed in Table 2 of the Specification located between starting base 16426 (the telomere proximal base) of locus asmbl__11856 and starting base 107039 of locus BG406195. Such polymorphisms can be identified by sequencing loci from flash and no flash germplasms. Centromere proximal flanking markers that can be used in these methods include, but are not limited to, M0202715 (SEQ ID NO: 9), M0206286 (SEQ ID NO: 10), M0206054 (SEQ ID NO: 11), and M0205375 (SEQ ID NO: 12). Additional markers located on linkage group L (chromosome 19) and other chromosomes are disclosed in US Patent Application Publication 20090208964. Publicly available marker databases from which additional useful markers located on linkage group L (chromosome 19) and other chromosomes can be obtained include, but are not limited to, the soybase.org website on the internet that is administered by the United States Agricultural Research Service, the United States Department of Agriculture, and Iowa State University. Soybean plants or germplasm comprising an introgressed genomic region that is associated with a no flash phenotype wherein at least 10%, 25%, 50%, 75%, 90%, or 99% of the remain genomic sequences carry markers characteristic of soybean plants or germplasm that are otherwise or ordinarily comprise a genomic region associated with the yellow flash phenotype are thus provided.

VI. Soybean Plants Comprising Genomic Region Associated with the Flash and No Flash Phenotypes and Transgenes that Confer Tolerance to Glyphosate A non-limiting and exemplary list of soybean plants that comprise genomic regions associated with either a flash or a no flash phenotype are provided herewith in Table 3.

TABLE 3

Soybean varieties comprising a genomic region associated with a no flash or flash phenotype.

| Branded Name[1] | Phenotype | U.S. Pat. No. | Variety Name in Patent | ATCC Depository Accession Number[2] |
|---|---|---|---|---|
| AG4201 | Flash | 7,071,388 | SE71112 | PTA-5728 |
| AG4601 | Flash | 5,659,116 | 927113675 | 97556. |
| AG4603 | Flash | 7,067,723 | SE73753 | PTA-5730 |
| AG4702 | Flash | 5,750,857 | 9390369478967 | 209547 |
| AG4902 | Flash | 6,143,953 | 931474956907 | PTA-2214 |
| DKB31-51 | Flash | 6,346,658 | 950045734453 | PTA-3871 |
| DKB37-51 | Flash | 7,294,764 | SD82997 | PTA-5737 |
| DKB38-52 | Flash | 6,660,912 | SD92955 | PTA-5382 |
| DKB40-51 | Flash | 6,683,233 | SD93038 | PTA-5329 |
| DKB46-51 | Flash | 6,933,423 | SE73090 | PTA-5733 |
| AG0801 | Non-Flash | 6,005,170 | 9422009600716 | PTA-269 |
| AG0803 | Non-Flash | 7,498,489 | 4498438 | PTA-9064 |
| AG0901 | Non-Flash | 6,080,917 | 942193611352 | 203207 |
| AG2403 | Non-Flash | 6,900,372 | SN71173 | PTA-5727 |
| AG2603 | Non-Flash | 7,388,131 | 4599695 | PTA-9070 |
| AG2703 | Non-Flash | 6,184,442 | 9323265446452 | PTA-2577 |
| AG3006 | Non-Flash | 7,482,516 | 0387907 | PTA-9029 |
| AG3302 | Non-Flash | 5,973,235 | 943470629664 | 203939 |
| AG3505 | Non-Flash | 7,569,750 | 4559809 | PTA-9023 |
| AG3703 | Non-Flash | 6,881,879 | SW90702 | PTA-5738 |
| AG3903 | Non-Flash | 6,632,982 | SW84112 | PTA-5299 |
| AG4403 | Non-Flash | 6,348,644 | 9472569612611 | PTA-3870 |
| AG4503 | Non-Flash | 7,378,578 | 0358232 | PTA-9003 |
| AG4703 | Non-Flash | 7,554,014 | 437973 | PTA-9066 |
| DKB06-51 | Non-Flash | 6,143,953 | 931474956907 | PTA-2214 |
| DKB08-51 | Non-Flash | 7,504,565 | 4878185 | PTA-9702 |
| DKB22-52 | Non-Flash | 6,858,783 | 0491727 | PTA-6187 |
| DKB29-51 | Non-Flash | 6,884,927 | 0509249 | PTA 6272 |
| DKB42-51 | Non-Flash | 7,479,582 | 4671685 | PTA-9027 |

[1]Branded names of ASGROW ® (designated "AG") and DEKALB ® soybean varieties from Monsanto Co. 800 N. Lindbergh Blvd., St. Louis, MO, USA.
[2]Deposit numbers of seed available through the American Type Culture Collection (ATCC), 10801 University Blvd., Manassas, Va., USA, 20110-2209.

Also provided herewith are additional soybean plants comprising a genomic region associated with a flash or no flash phenotype that are identified by use of the markers provided in Table 1 and/or Table 2 and/or methods provided herein. Any of the soybean plants identified in Table 3 or other soybean plants that are otherwise identified using the markers or methods provided herein can be used in methods that include, but are not limited to, methods of obtaining soybean plants with an introgressed no flash locus, obtaining a soybean plant that exhibits a no flash phenotype, or obtaining a soybean plant comprising in its genome a genetic region associated with a no flash phenotype.

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. No. 6,803,501, RE39,247, U.S. Pat. No. 6,225,114, U.S. Pat. No. 5,188,642, and U.S. Pat. No. 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and U.S. Pat. Reissue Pat. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in US Patent Publication 20090036308), or any combination of i (MON89788 soybean), ii (GTS 40-3-2 soybean), and iii (event 3560.4.3.5 soybean).

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in US Patent Application Publications 20100086963, 20090215060, and 20090025288, which are incorporated herein by reference in their entireties. Published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, also disclose apparatus and systems for the automated sampling of seeds as well as methods of sampling, testing and bulking seeds. Thus, in a certain embodiments, any of the methods provided herein can comprise screening for markers in individual seeds of a population wherein only seed with at least one genotype of interest is advanced.

VII. Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers form the basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include, but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with no flash loci, regions flanking no flash loci, regions linked to no flash loci, and/or regions that are unlinked to no flash loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with no flash loci, regions flanking no flash loci, regions linked to no flash loci, and/or regions that are unlinked to no flash loci can be used in certain embodiments of the instant invention.

Herein, nucleic acid analysis methods include, but are not limited to, PCR-based detection methods (for example, Taq-Man assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of Genotypes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of a Locus Associated with Yellow Flash

In yield trials being conducted at Thomasboro, Ill. in August, 2003, it was observed that some F3:5 soybean lines of the pedigree A3525/DKB31-51 (that contained a transgene that confers glyphosate tolerance and exhibited yellow flash when sprayed with glyphosate (i.e. ROUNDUP WEATHERMAX®) while other lines of the same pedigree showed glyphosate tolerance and no yellow flash symptoms. Repeat experiments conducted in 2004 produced similar results in 130 F3:6 lines in yield trials conducted at Hopedale, Ill. A3525 is a commercially available Asgrow® soybean variety and is also known under the variety name SN70025. DKB31-51 is described in U.S. Pat. No. 6,346,658 and samples of this seed have been deposited previously under ATCC accession number PTA-3871.

Fifty-three lines were categorized as either "Flash" or "No-Flash" with the remainder of the material falling between the extremes.

The fifty-three lines categorized in 2004 were planted at Covell, Ill. in 2005 and were sprayed with ROUNDUP WEATHERMAX® at a rates of about 42 oz/acre on a weekly basis beginning at about the V3 to V4 stage for up to four weeks, thus in certain instances attaining a total rate of glyphosate exposure of a 4 week span of about 168 oz/acre. Tissue samples were collected from one individual plant from each of fifteen lines that demonstrated the most severe yellow flash and fifteen that showed no symptoms. Table 4 shows the breeding and testing history of the materials used in this study.

TABLE 4

Breeding and testing history of the materials

| Gen. | Season | Year | Location | Bulk/SPS/Prow/PRYT |
|---|---|---|---|---|
| Cross | Summer | 01 | Ames, IA | Cross |
| $F_1$ | Winter | 01 | Isabella, Puerto Rico | Bulk |
| $F_2$ | Winter | 01 | Isabella, Puerto Rico | Pod Pick |
| $F_3$ | Summer | 02 | Bloomington, IL | SPS |
| $F_4$ | Winter | 02 | Rancagua, Chile | Progeny Row |
| $F_5$ | Summer | 03 | Bloomington, IL | Yield Trial |
| $F_6$ | Summer | 04 | Bloomington, IL | Yield Trial |
| $F_7$ | Summer | 05 | Bloomington, IL | Spray Trial |

SPS: Single Plant Selection.
Prow: Progeny Row.
PRYT: Progeny Row Yield Trial.

Example 2

Identification of Molecular Markers that are Associated with a "Yellow Flash" Phenotype To identify marker associated with yellow flash symptom, we used a "Genome Scan" approach. Fifteen samples from lines showing no flash and 15 samples from lines with severe flash were collected from a segregating population (F3:6).

DNA were extracted from these 30 samples and used as templates to screen a set of 2746 SNP markers that provide a high-density coverage of the entire soybean genome with approximate two markers per CentiMorgan Unit (cM). Allelic scores at each marker were collected and compared across 30 lines. Of the 2746 markers tested, 776 were segregating and 226 were heterozygous. Two markers, M0102027 and M0101742, clearly showed one allele in no flash and another allele in flash samples (Table 5), indicating a linkage between these two markers and the phenotypes. Having 15 plants showing the same allele and the same phenotype by chance is very low ($\frac{1}{2}^{15}$). Therefore, this could not be explained by a random event. A third marker, M0129138, show one allele on the flash lines and another allele on 14 out of 15 no flash lines, indicating a linkage of this marker to the flash phenotypes. M0101742 and M0129138 turned out to be mapped on the same chromosomal location with no recombination on the mapping population. Other data supporting the linkage is that all seven commercial varieties with known flash phenotypes matched perfectly with the allelic data on the two markers.

TABLE 5

Genotypes for Yellow Flash Phenotype

| Locus | Linkage Group | Map Position (cM) | Flash Varieties | | | No Flash Varieties | | | | |
|---|---|---|---|---|---|---|---|---|---|---|
| | | | DKB26-52 | DKB31-51 | DKB38-52 | CI3478 | AG3602 | AG3305 | 037014-11-18 | A3525 |
| M0101742 | L | 2.4 | CC | CC | CC | TT | TT | TT | TT | TT |
| M0129138 | L | 2.4 | AA | AA | AA | GG | GG | GG | GG | GG |
| M0093116 | L | 4.0 | AA | AA | AA | AA | AA | AA | AA | AA |
| M0129925 | L | 4.0 | CC | CC | CC | CC | CC | CC | CC | CC |
| Phenotype | | | FL | FL | FL | ? | NF | NF | NF | NF |

FL: exhibit yellow flash phenotype
NF: exhibit a no flash phenotype

Example 3

Analysis of the Genotype of Soybean Varieties and Yellow Flash Phenotype

Approximately 1,700 soybean varieties (lines) were assayed or typed for the presence or absence of allelic variants of the markers M0101742 (SEQ ID NO: 5), M0129138 (SEQ ID NO: 4), M0093116 (SEQ ID NO: 6), and M0129925 (SEQ ID NO: 7). Of these lines, complete scores for all four markers were obtained in 844 lines. A summary of the genotypes observed in these 844 lines is provided in Table 6.

TABLE 6

| # Samples (lines) | Genotype[1] | Phenotype |
|---|---|---|
| 706 | TTGGAACC | No Flash |
| 193 | CCAAAACC | Yellow Flash |
| 113 | CCAATTGG | |
| 46 | TTAAAACC | |
| 43 | TTGGAAGG | |

TABLE 6-continued

| # Samples (lines) | Genotype[1] | Phenotype |
|---|---|---|
| 16 | TTGGTTGG | |
| 11 | TTAATTGG | |
| 9 | CCAATTCC | All Plant Introductions (PIs) |
| 8 | CCAAAAGG | |
| 5 | TTGGTTCC | |
| 4 | TTAATTCC | All Plant Introductions (PIs) |
| 3 | TTAAAAGG | All Plant Introductions (PIs) |

TABLE 6-continued

| # Samples (lines) | Genotype[1] | Phenotype |
|---|---|---|
| 1 | CCGGTTGG | All Plant Introductions (PIs) |

[1]The genotype of a line is shown as N1N2N3N4N5N6N7N8, where N can be A, T, G, or C depending on the position and the line and where N1 is nucleotide 1, N2 is nucleotide 2, N3 is nucleotide 3, N4 is nucleotide 4, N5 is nucleotide 5, N6 is nucleotide 6, N7 is nucleotide 7, and N8 is nucleotide 8. The genotype represents the both the paternal and maternal allelic forms of the markers M0101742 (SEQ ID NO: 5; position 1206; nucleotides 1 and 2 in genotype shown), M0129138 (SEQ ID NO: 4; position 218; nucleotides 3 and 4 in genotype shown), M0093116 (SEQ ID NO: 6; position 183; nucleotides 5 and 6 in genotype shown), and M0129925 (SEQ ID NO: 7; position 328; nucleotides 3 and 4 in genotype shown). Thus the genotype "TTGGAACC" means that the line is "TT" for both the paternal and maternal contributions to the M0101742 polymorphism, "GG" for both the paternal and maternal contributions to the M0129138 polymorphism, "AA" for both the paternal and maternal contributions to the M0129116 polymorphism, and "CC" for both the paternal and maternal contributions to the M0129925 polymorphism.

Sixty 63 soybean varieties were subsequently selected from various genotype groups and tested for yellow flash essentially as described in Example 1 (i.e. were sprayed with Roundup WeatherMax® at a rates of about 42 oz/acre on a weekly basis beginning at about the V3 to V4 stage for up to four weeks, thus in certain instances attaining a total rate of glyphosate exposure of a 4 week span of about 168 oz/acre). The results of those analyses are provided in Table 7.

TABLE 7

Genotypes and Phenotypes of Selected Varieties

| M0101742 (SEQ ID NO: 5)[1] | M0129138 (SEQ ID NO: 4)[1] | M0093116 (SEQ ID NO: 6)[1] | M0129925 (SEQ ID NO: 7)[1] | Overall Flash Score[2] | Phenotype | Number of lines tested |
|---|---|---|---|---|---|---|
| CC | AA | TT | GG | 1.8 | No flash | 14 |
| CC | AA | AA | CC | 4.4 | Flash | 15 |
| TT | GG | TT | GG | 2.4 | Partial resistance | 1 |
| TT | GG | AA | GG | 2.6 | Partial resistance | 3 |
| TT | GG | AA | CC | 1.7 | No Flash | 30 |

The genotype represents the both the paternal and maternal allelic forms of the markers M0101742 (SEQ ID NO: 5 position 1206), M0129138 (SEQ ID NO: 4, position 218), M0093116 (SEQ ID NO: 6; position 183), and M0129925 (SEQ ID NO: 7, position 328).
Flash Rating Scale:
1: Green-No Yellowing
2: Mostly green, very slight yellowing <5% (1-2 plants with some yellowing)
3: 5-10% plants with yellowing
4: 11-20% plants with yellowing
5: 21-35% plants with yellowing
6: 36-50% plants with yellowing
7: 51-65% plants with yellowing
8: 66-80% plants with yellowing, some necrosis
9: 81-100% plants with yellowing and or necrosis For optimal prediction of yellow flash phenotype, all four markers (M0101742, M0129138, M0093116, and M0129925) can be used. However, one can achieve high predictability with only two markers, M0101742 and M0129925. Based on fingerprint information, these two markers would identify two genotypes: CCAAAACC and CCAATTCC. CCAAAACC is the predicted genotype for plants which exhibit yellow flash (193/844 varieties screened based on fingerprint analysis). CCAATTCC is an additional genotype which only represented 9/844 varieties based on fingerprint data. All 9 varieties comprising the CCAATTCC genotype were Plant Introductions (PIs). As used herein in reference to soybean, Plant Introductions (PIs) refer to mostly typical germplasms that have not been subjects of breeding improvements. For example, PIs are include lines that have not been obtained by intercrossing followed by selection. PIs can also include lines obtained from seeds or vegetative propagules of plants that have been introduced from another country. Therefore, the two markers M0101742 and M0129925 could distinguish between the three most common genotypes observed: CCAAAACC (associated with a yellow flash phenotype), TTGGAACC (associated with a non-flash phenotype) and CCAATTGG (associated with a non-flash phenotype). More specifically, where M0101742 is CC and M0129925 is CC, one would predict that most soybean lines thus identified, and that were obtained from, or related to, the varieties analyzed in this Example, would have a Yellow Flash phenotype.

Example 4

Genotypes and Phenotypes of Various Commercial Varietie

In field tests conducted in 2006, a number of commercial varieties were genotyped with the markers M0101742 (SEQ ID NO: 5), M0129138 (SEQ ID NO: 4), M0093116 (SEQ ID NO: 6), and M0129925 (SEQ ID NO: 7) and exposed to glyphosate to test for the presence or absence of the yellow flash phenotype essentially as described in Example 1 (i.e. were sprayed with ROUNDUP WEATHERMAX® at a rates of about 42 oz/acre on a weekly basis beginning at about the V3 to V4 stage for up to four weeks, thus in certain instances attaining a total rate of glyphosate exposure of a 4 week span of about 168 oz/acre). The results of this analysis is provided in Table 8.

TABLE 8

| Branded Name[1] | M0101742 (SEQ ID NO: 5)[1] | M0129138 (SEQ ID NO: 4)[1] | M0093116 (SEQ ID NO: 6)[1] | M0129925 (SEQ ID NO: 7)[1] | Phenotype | U.S. Pat. No. | Variety Name in Patent | ATCC Depository Accession Number[2] |
|---|---|---|---|---|---|---|---|---|
| AG4201 | CC | AA | AA | CC | Flash | 7,071,388 | SE71112 | PTA-5728 |
| AG4601 | CC | AA | AA | CC | Flash | 5,659,116 | 927113675 | 97556 |
| AG4603 | CC | AA | AA | CC | Flash | 7,067,723 | SE73753 | PTA-5730 |
| AG4702 | CC | AA | AA | CC | Flash | 5,750,857 | 9390369478967 | 209547 |
| AG4902 | CC | AA | AA | CC | Flash | 6,143,953 | 931474956907 | PTA-2214 |
| DKB31-51 | CC | AA | AA | CC | Flash | 6,346,658 | 950045734453 | PTA-3871 |
| DKB37-51 | CC | AA | AA | CC | Flash | 7,294,764 | SD82997 | PTA-5737 |

TABLE 8-continued

| Branded Name[1] | M0101742 (SEQ ID NO: 5)[1] | M0129138 (SEQ ID NO: 4)[1] | M0093116 (SEQ ID NO: 6)[1] | M0129925 (SEQ ID NO: 7)[1] | Phenotype | U.S. Pat. No. | Variety Name in Patent | ATCC Depository Accession Number[2] |
|---|---|---|---|---|---|---|---|---|
| DKB38-52 | CC | AA | AA | CC | Flash | 6,660,912 | SD92955 | PTA-5382 |
| DKB40-51 | CC | AA | AA | CC | Flash | 6,683,233 | SD93038 | PTA-5329 |
| DKB46-51 | CC | AA | AA | CC | Flash | 6,933,423 | SE73090 | PTA-5733 |
| AG0801 | TT | GG | AA | CC | Non-Flash | 6,005,170 | 9422009600716 | PTA-269 |
| AG0803 | TT | GG | AA | C | Non-Flash | 7,498,489 | 4498438 | PTA-9064 |
| AG0901 | C | A | T | G | Non-Flash | 6,080,917 | 942193611352 | 203207 |
| AG2403 | T | G | A | G | Non-Flash | 6,900,372 | SN71173 | PTA-5727 |
| AG2603 | T | G | A | C | Non-Flash | 7,388,131 | 4599695 | PTA-9070 |
| AG2703 | T | G | A | C | Non-Flash | 6,184,442 | 9323265446452 | PTA-2577 |
| AG3006 | T | G | A | C | Non-Flash | 7,482,516 | 0387907 | PTA-9029 |
| AG3302 | T | G | A | C | Non-Flash | 5,973,235 | 943470629664 | 203939 |
| AG3505 | T | G | A | C | Non-Flash | 7,569,750 | 4559809 | PTA-9023 |
| AG3703 | T | G | A | C | Non-Flash | 6,881,879 | SW90702 | PTA-5738 |
| AG3903 | T | G | AA | CC | Non-Flash | 6,632,982 | SW84112 | PTA-5299 |
| AG4403 | T | G | A | C | Non-Flash | 6,348,644 | 9472569612611 | PTA-3870 |
| AG4503 | T | G | A | C | Non-Flash | 7,378,578 | 0358232 | PTA-9003 |
| AG4703 | T | G | A | C | Non-Flash | 7,554,014 | 437973 | PTA-9066 |
| DKB06-51 | C | A | T | G | Non-Flash | 6,143,953 | 931474956907 | PTA-2214 |
| DKB08-51 | T | G | A | C | Non-Flash | 7,504,565 | 4878185 | PTA-9702 |
| DKB22-52 | T | G | A | C | Non-Flash | 6,858,783 | 0491727 | PTA-6187 |
| DKB29-51 | C | A | T | G | Non-Flash | 6,884,927 | 0509249 | PTA-6272 |
| DKB42-51 | T | G | A | C | Non-Flash | 7,479,582 | 4671685 | PTA-9027 |

[1]The genotype represents the both the paternal and maternal allelic forms of the markers M0101742 (SEQ ID NO: 5 position 1206), M0129138 (SEQ ID NO: 4; position 218), M0093116 (SEQ ID NO: 6; position 183), and M0129925 (SEQ ID NO: 7; position 328)
[2]Deposit numbers of seed available through the American Type Culture Collection (ATCC), 10801 University Blvd., Manassas, Va., USA, 20110-2209.

Example 5

Exemplary Marker Assays for Detecting Polymorphisms

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with a no flash phenotype are given in Table 9.

TABLE 9

Exemplary Assays for Detecting Polymorphisms

| Marker or Locus Name | Marker SEQ ID | SNP Position | SEQ ID Forward Primer | SEQ ID Reverse Primer | SEQ ID Probe 1 | SEQ ID Probe 2 |
|---|---|---|---|---|---|---|
| M0129138 | 4 | 218 | 17 | 18 | 19 | 20 |
| M0101742 | 5 | 1206 | 21 | 22 | 23 | 24 |
| M0093116 | 6 | 183 | 25 | 26 | 27 | 28 |
| M0129925 | 7 | 328 | 29 | 30 | 31 | 32 |

Example 6

Oligonucleotide Probes Useful for Detecting Polymorphisms by Single Base Extension Methods Oligonucleotides can also be used to detect or type the polymorphisms disclosed herein by single base extension (SBE)-based SNP detection methods. Exemplary oligonucleotides for use in SBE-based SNP detection are provided in Table 10. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 4 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected. Exemplary forward and reverse SBE probes are provided in Table 10.

TABLE 10

Exemplary SBE Probes for Detecting Polymorphisms

| Marker or Locus Name | Marker SEQ ID NO: | SNP Position | Probe (SBE) | Probe (SEQ ID NO.) |
|---|---|---|---|---|
| M0129138 | 4 | 218 | TGTGTCCTATATGATCTT | 19 |
| M0129138 | 4 | 218 | TGTCCTGTATGATCTTA | 20 |
| M0101742 | 5 | 1206 | TGACTAGCATGTATCTAT | 23 |
| M0101742 | 5 | 1206 | ATGACTAACATGTATCTAT | 24 |
| M0093116 | 6 | 183 | CCAACACCAAACTA | 27 |
| M0093116 | 6 | 183 | CAACACCAAACAA | 28 |
| M0129925 | 7 | 328 | AGTAGTAGCTAGTGAAATA | 31 |
| M0129925 | 7 | 328 | AGCTAGTCAAATATTT | 32 |

Example 7

Summary Table of Nucleic Acid Sequences

TABLE 11

Nucleotide Sequences

| Marker or Locus Name | SEQ ID NO: | Sequence |
|---|---|---|
| M0205350 | 1 | gggcttctccgctcgaacttatgcaagggctatgtgatggtgatgatgattgaatttgaagctgctactgca ttactctctttggtaatgaatttgaagaagcagaaagaaaggaaatgatggtctttacaccgtcaattttaat atwtgtaagtgtaaactctgtagtagcacagtgatgtagtgtagattaggcatttggcagcgtggtaaatat tcttagattgaattgtgttatcaacagtattaaacgttttaggctgaatgaatgatattgatgaatttataaggt ggggaggctaagatggaatcatgtagtta |
| M0114388 | 2 | aattacacacatcatgatcttgtaatcatcatctcccaaatcagggatagccttggccttcttacc ccagggattccataccactgcactctcattatcaccaaaccaataagtgacatcaattgtagattaaattaa caaactttatgtaaatctgaatgctggatctggcccttataaagtgaaaaacacgttgtagagactaaagta agtaatccccttgttttttgatgaggaaatgaacagttgatattatgtgcacttgtataacaaaacatggatatt ttaaaatatcagtcgttgattttctcatcaataaattaggattgttttactctctaaagtgacttgttcagattaga agagccaaatagatacaatgccatgcaaaattttttattctctgactaataactaataacaacctgcatctgg cattcctttcttctggagtacaaaagttctttttttctcatggtctatgatggcaattttagttgggctrtgcaagt acactcctgtccatctacaaggtaaccacaaatgtccttagagaacacttgaaaaaaaagttgatttggtatc tattatatatattcatacactcgaaaatcaatcagaatatatataggttatgtgcacttatgtgcttatgatgtca atttttcttagcctgtgagacacctccaaccaattgaatgaaaggaccagaaaatcaaattatacctctccat caaaagtgagtgcatctgcctgctctgtgaaccttgatctgttcaacagattgtcaaagtaatccagtgtct ccaatccctcaatacgcacttc |
| M0205928 | 3 | attcctatttcctacacaacactacactgtctggtggaagaatctcttcactctccatgcaacaacgttggct atgtctccttattctctctctttgttagcctctgtctccccaaaatgcacacccttctttctttctcctcatcaca ctctccacatcttccaaaccacaacataaccaaatccaataataaactctctcattccatcaatggactttca tcmtgcccttcttctcctttgctccccagtgccacaaaatcttctccctttctcatttccacttcaaaaattgca tctttcagggtccttgctgcttcctctatacctgatgctagaagtgatgaaccagccaaaactagtgatttctt aaaaactcttcag |
| M0129138 | 4 | cgccagcttgcatgcctgcagttccaagaattatttcaaaccgctgcttccattttagaatccttgttatgtcc ttttctgcacagtagattagtatgtcacaagttgcatgttgggccggttgatttttatgaaattaataagagtta aatatgttttttagtccttgcaaataggaaaaagttctccttttggtcctcaattatgaaaatgtgtcctrtatgat cttatttacataaatgaggaaatgaaagcagatgatacttttatgaaggacaaagattacatttgacacatttt cataaatgagtgactaaaaagaagcatttttattttttagtgattaaattaattggaaacattacaagattacttt ggtcatgggttcaagaatccggaaacagtttctttgcatatgcaagggtaatgctgcttacaatatccctcc cccataccttggcatagtgaggagcctccgggcaatggaatacactagttttttatagtacaatattttcattt agagttactgtgggacaaaaggaacttaccaaaaatgaattgatctaagctcttgttaggtaggtactcata cacaatgaggctctcagggccttcaatgctgcaacccaatagtttgacaaggttcttgtgttgcattccact aatcaaattcacttcattgaaagaatcatccacccattgcctattattgaagaccaatctcttaacagcaaca tcattcccatttggcagagtccctttgtatacagaaccagatcctccttgacctatctttcttgaagagctgaa |

TABLE 11-continued

Nucleotide Sequences

| Marker or Locus Name | SEQ ID NO: | Sequence |
|---|---|---|
| | | ataatccgtcgccttctctagagtttcatatttgtaattcaagctagaattcttcaaggaaggaggaacctca<br>ataaaattgttttctgagtgattcaggagaaaatgaaatacagcatcagcaaaattaacaaacaatcattcc<br>aaatatatattattggtatgaacaagagtgttctccagaacattacttcttctcttttggtgaaggccacataa<br>gagactgcaagagtgagaactacaac |
| M0101742 | 5 | acacagaaatcacaaacaagtggtgactacttacccatattcaccaaagaaatgaaaaacttctagaac<br>ttgtgacaaaacaaaactgggggactcactctgagggcatgtcatcaacaacaaccactcctatctatgg<br>cttggcacaatgcttccaagacctttccagcattgattgccttcaatgctttgcagccagccgcaccaagct<br>ccctcgctgcctcccttcggtttcggctcgaatttaccttgatggctgcttccttcgctatgacaattacagtt<br>tctacactgaaaactatgacccctttgagggacacagtgaattgcacctcagagtatggttctgtggttggtg<br>atggtgagaagttggtgtttgctgagagtgttggcaaagtggttgagagtgtggtgagggtggctgtgaa<br>taataatgagggaagaggcttttttgcagttggagaaggtgggggagtttatgcattggcacagtgctgg<br>aaaactgttgggtaaaagggtgtagtgattgcttgaggaaagctgaaaatgaggtcaaaggatgtttgc<br>ctaagagggaagggagggccttgaatactgggtgctatttgaagtactcaactgttaagttctacaatcaa<br>ggaggtcaagatggtcaaggagatggtaagagctgttgctctagtttgaagttttttatattcttcattagtttc<br>ttggttccttttggataaacttctcaaccactagttataggagaaaaaatgaattaaacatctcttgtaagtt<br>aaaatcaatttgtgcacttcgataagttttataaaaactctctcgtttaacttttccaaaagctgagatgtataa<br>gttaattttaacttacagaagaagtttgattcattttttgcttttatgttcttctccttttaagtattattgagaagc<br>ttatcggttggaatttggaaactgaagctcaactgggaatttcaattgcatattgttaccatgcagtttcaaattc<br>cttgtgttgcttataggttaaatgacaaatggagaaggaaagaagtaaagatgaatgttactgtatcattgt<br>gaatgaaatgctgcttttcaactttaactttgctataactcttaggttagttttggtgtctaaagtttgtcctgaat<br>agaatcctaggtttcagttcatagatggcatagatacatgytagtcatttattttgtacatgttgatgcaatt<br>gtccatgttttaattttcagattcttccagaaaacgagtcattatagcagcagggtcagtctt |
| M0093116 | 6 | attatatgagggctcttgggttttcaaggacactgatgcaccttacctgtaagaatatgattttgttattatt<br>attattatatttattgtgagtctatatatataagaagaattttccattttgtttcatctaattaatatagttttaata<br>atttttaaatttttgctttgtttaatgcttwgtttggtgttggaaattaagattgttccagggtttgatgctgctggtg<br>tggtggtgagagtgggaagtaaagtgagcaaattcaaggttggagatgaagtttatggtgatatcattgag<br>tatgcttggaataatccaaagaccattgggactttggcagaatatactgctactgaggagaaagtgttggc<br>tcacaaaccctccaatttaagctttattgaagcagctagccctt |
| M0129925 | 7 | aggcaccaaaccaagggatttaaaatttattaaattataaacatgaaatgattaaataaagagttgaattcc<br>cataattttatacgttttattaaatttcactcagcaaaaaatgtattaaaaaatatattattcccatttgtctgtctt<br>tatttatgtcatctatttttaattttttctgatgtatttaactggggccaaactgaaacatgttgatcatgcaaaggc<br>ctactccaccatttcacatgtacgtgtcatcacccagcaacccccattttttctacataacacacactccctctct<br>aacactcacactccaataacaaatatttsactagctactactcttcttagtttctctgttgtatcattttttattgcta<br>tatcctaatcaaacttcactctcaaaatgagtgatcccacactagcacaacagcatctagtcaaagtccac<br>acaacaacacacgaaacagttgttaccacacacaatcataaccaaacaccctcaataaatgtgtgttact<br>gaattatttaatttatttgtacacctaactatgattaatatttaatttcttcaaaactttgtttatgcatgataaccgtg<br>attaattttttatttttttccccctatgattgagaacaggcctcaggtgaaaagaagaagattgtggggggttct<br>acaaagggaatgaatatgctaaattgaatccaaattttgttggatgtgttgaaggtgcattgggaatacgtg<br>agtggctggaatcacagggtcatcagtacattgtcactgatgacaaagaaggacctgattctggttagta<br>cttagtatcttgccaacttaattcaagtttgagtaaactatttattttttgatgatttgatctataaaagtgtacaaca<br>ttgtgaaattagtctctaacattgtcacattagtctctgaaattaagataaatttcatatgacaaatgacatgttat<br>taactcttttttcgtactgtaaattgaaaaatgtggctacgtgttatatgaaaattggttgggacctggtctcgg<br>atcatgtaataatttctatcaaacaaggtatcagagtaatcaacactataatatcatggaatgcaaatgtgttt<br>gtcccttcaagattttaattgcttgaactcaatggaatttgatgttct |
| M0205537 | 8 | aggaaatactagattttgatatactattatttaataattttcctactcgactaaaatgaaaaaaaaaaacactaa<br>aataatgatatcactaatattattagctgaattttttttgtttgttgaatcttttagttgactgaatttagtatttgac<br>taaaamaagaatcatatcacaaactaatttgcctgtaactcattgcttttaaaaattgcttttaaaataattgtcagcaa<br>gtctagatttttaatgattagatagatagctaacaaaaataccacactggatacatatgaaatcaatattaag<br>tttaaagagatgcaaatacgcaatcgatttgattaatgaatttcaaatgttctgcgttaaattaattcaattaccttttt<br>aaattgaatgttttcattcctgggctctg |
| M0202715 | 9 | atgatgggatcttgcatatgcccgttggagactccggcgaggttgctttggaccacaagcttcttccgtca<br>taagcttatgatcttctaataattaataattcacgcacacaaacaaacaaacaaacaaacaaaaacacttc<br>ataacaacaacaacaaccccttctgaaattctcaacacaagtttcaaaaaacagagtaaaagaaacagag<br>caaaaacacacacacaaaaacacaaacacagacacccttttaagtattaaggtgtctctttctctcsccgga<br>aagtttctccgtcggcggtggtgattgaccggagtgccatggagtctggacgggattttctttggtgcctctg<br>cttcaagcggcaacaacatgctcttctcggcacaactgaact |
| M0206286 | 10 | tagtaaagccaccaactccaacaccaacttccccagtggtgtaccctcctcctnnntttccatctccacca<br>gctcctgtgtggaaatcaaacaagggtaagtgtgtaccacatctatstctttagtaactcctttccgatctcta<br>atgtaattaaatgaaatgattctgtcacatttttctgctaatttaactttttacgttatttagaaaaaaaatataaaa<br>gaaatttgtatcacttttttctttaaaaatagggaaaaatatgtgtgataaaatagataatgttttacaatttcattac<br>agaaatactttatattttataatgttaatatttttttattttttcacaatttttttcttctttcttattagttttggac<br>ttaaattaaataattatttttaatcctgtcatgtgggttttagtattcttaataatttattttttcttgtttttgattactgta<br>aaatgttttagtaaggcttaactaaaacagacaaagaaaaatattttcaagaagatttaaaatgaaaaaaagaatctta<br>taatacatggattaaaaaaattagtgaagccttacttttgttttttctttttctttgttacacgtcttcaccttgttgt<br>ctttgttatccttttcacatctaatgatggatgtgagagaagaaccatgcatggtcttaattgtttatgtgattaat<br>ggctttaaagtatagaactttttaagtaagatcagttgagttaattaatgaaacatggtctttttgttttccaaattt<br>ttttgtgggcagattgcattccactaagggattataggtgctcattacactcaaggaagaaattgt |

TABLE 11-continued

Nucleotide Sequences

| Marker or Locus Name | SEQ ID NO: | Sequence |
|---|---|---|
| M0206054 | 11 | atcttggttttccaatcgcgcagcccgagcggccatcwgaacaacagtatctacgtcaactccttttagcaaaaatct<br>acagaaaacattgaaaacacttgtgtgagcatacgacaaggcaaataagaaaacaacacagtacaaaactgacta<br>cttctaacctcaataagattcttgtcaactgtcagtttattcaaagtcaaagttccagttttgtcgctacataataca<br>tccattcctgccatctcttctattgctgtcattcttttagtaatagcaccctgcaatgattatataaagcataaacta<br>taaagactaacatctaattgattaaaacttgagacaactgtcgtttttcaagaagcactaatgtctacctgctgagctaag<br>cgatgggatccaattgccattgtcactgacaaaacagtaggcatggcaataggaattcctccgataagaagcacgagc<br>agattgtcaatcccaggacgatattcccggtgttgaattgggtacatgacaatgat |
| M0205375 | 12 | ctttgattcttgccagtcttttttcattctttttcattcttaaatccatcaaatgaacctattgatatgactgaaacct<br>tggattagccaagactaaagctactccacttgagattttaattaagccacgattatcttctagttgttatytataaa<br>agcatgtgaatcttgtcttagcggtttgtggaaagtctgttgttaaactatgtgatcttcttttagataaatcaggtt<br>tgcctgataaattatattttcgtcaaaagggcattttggaattcacaaaattgtcatcatgtggtgttgaaataagg<br>tgtgttgtaataaggtttaaggctt |
| BG406195 | 13 | tattgtcttttgtgaatgatcaataacttcctaatggtaattcctttcattagagagcccatggatttatattcccat<br>ggtttggaaaaaagttcttcaagcagtgtaagtaacaccaatggttttactgaaaatctggtattcggtgacgcttat<br>taacatcaatttgaccaatggttttactatgacgcttattaacatcagttaacggtatgaagcttgggaaagctgtt<br>ggaaaatggggtctttgagatgcttgatgcaagtttgccatcatgacttccatttcacacttagacattgagtggtga<br>acgtccatagtatttgatataaatg |
| BU082700 | 14 | gcaccagtccacacaaagaagattgtccacagagatgttaaaacagaaaatatgcttctggacaagacacgaacc<br>ttgaaaatagctgattttggagtagctcgtattgaggcctccaatcctcatgacatgacaggtgaaactggaacccctt<br>ggttacatggctcctgaggtacatgcttcaattccttttgaaaattctctctcctgtgcattgttctttggggtttg<br>tttcaaacacccttaatgtctagtccttacctcagaaaattttgaaaatgctggcttaggacttgttacttgcgaccg<br>gctctgttgtctaactaattgtgaaagaactgggttgaatatttttggacttaaaatataaggaaaaattactaaaca<br>ggaattcttgattaaaatattaaccatgttggaaagataaggacattgaattgttccatcactgtccttactttcatc<br>aggaattcctttttgttttatagttcacccaacaattatgtatatatccatgttggtttttggtacataattacaggaag<br>aaatctttacctcagtcccatttacaattactgagatctagaactgcagcatgtcactactcactaatcttga |
| TA14086_<br>34305 | 15 | atggcaagcatttctagcattccatcacacataaaaacttgggtttattctgaatatgggaacacagaagagattcta<br>aaatttgatcccaacgtacctataccagacatcaaggaagaccaggtgctcatcaaggttgtggctacagctcttaat<br>cctgtggattataagagggctcttggctatttcaagaacactgactctcccttacctgtaagatcatgattttaaatt<br>tatatttgcgtggattattaattagtatagtttccattttgtataccaccttatataattcttttttgtttaaatata<br>ttttagttttataatttatattttttttttgttattgtaaatttttttgtttttgtttttataaatta<br>tgtttgttttatttttctttcctaaattatttagataatgttttgaatagtaaaaaaatattataacaataaaaat<br>aaaataaacataatttgtaagaatcaaaaataaaaataatttgtaagtaaaaaaataaaaaataaataaattataag<br>gattaaaattgtatttaagccatttttttttatcattgcattgttaatttgtgtttggtttttgaaattaagagtgt<br>tccggggtacgatgttgctggtgtggtggtaagagtgggaagtaaagtgaggaaattcaaggttggggatgaggttta<br>tggtgatatcaatgagtatgctgtgaataatccaaagaccattgggactttggcagagtacactgctactgaagagaa<br>attgttggctcacaaaccctccaatttgagctttattgaagctgctagccttccttagctatcatcactgcttatca<br>aggacttgaaagagttgattttctgctggaaaatctatacttgttctaggaggtgctggtggagttggatcccttgt<br>tattcaggtttgatatcttccatctccattggttaatttgacaataagtttcaattaaacagtgtcttactgaaatat<br>tgagccattaatttcactttttcagtattttagttatttattttattcttcttctctaatcatatgatttaggagcaa<br>tgatatttagatatctctctaaatttcagacacctcatatcatatcatttatcatttattatattttctcttttcctc<br>tctatctctcttagcataattatataattaataatgaattgttgggtatttgattgatatgatgtagctcg<br>ccaagcacgttttggcgcatccaaggttgcagctactgctagttccgcaaaactggatttattaaggaaacttggga<br>gcagactttcctattgattacacaaaggagaattttgaagagcttgcagagaagtttgatgtagtgtacgatacaata<br>ggtcagatgttgaaattgaacttaaattatttgtttcacatgaagtcagtttggtcatgactaatacaatattaacat<br>atgagatgtggtatgagtacaacaattggtacagaactattagttttataccttcttacttatttatgacatgtaa<br>taaataatgtacaccagagatattaacacaaaagaatgttgttatacaattaatttaaagtgcattaacatgtaacat<br>acaacttattacttttgttatcttattattgattaccatgtgtaataagattgttgataataaattacttttaaga<br>attgttatctattttttttattagtggatagtataaaagtatttttcatgtgtatcaatattattattgaaaatgaaga<br>catggttgattccaaaaacagggcagagtgacaaggcattgaaggctatcaaagaagggggaaagttgtgacaatag<br>caccaccagcaactccacctgctatcccattctttctcacttcagatggtgctgtgttggagaagttacaacctcact<br>tagaaagtgggaaggtgaagccagtattggatcctaagagtccctttccattttctcagattgtggaagcatattcat<br>acttgaagacaaatagagccattgggaaagtagtcatacatcccatccttgaacatatataactatgcaaatatact<br>atcaagtcctgctgtgcattctgaccttaatttgtgttaataaggttaatatttatatgattgataaggagagagc |
| BU551345 | 16 | tttagtcattagaattttacttgtttactcggttcgaaagttccatctcgctggtctcaattactattaaaaaatctc<br>atattgcttacctcaattagtgggatgaggtttaagtacgtgatgaacaacttcacttnntgctaattagtttgaagt<br>tataatgtaacatgctctatccttcttttggttggttgcttgggggggagctcccnnnnacatggaattattgggaat<br>caagcttccataattgtttcttcacttcttgatggcctaattaagctgcatgtgctagagaactcagaggggctgtag<br>gacacaccaatcttcttaaatgtgtttgatgaggagctgtctatgctaaaacctaatggagatgtttgatct |

Polymorphic nucleotide bases are designated in Table 11 and in the sequence listing provided herewith according to the WIPO Standard ST.25 (1998), Table 1, as follows: r=g or a (purine); y=t/u or c (pyrimidine); m=a or c; (amino); k=g or t/u (keto); s=g or c (strong interactions 3H-bonds); w=a or t/u (weak interactions 2H-bonds); b=g or c or t/u (not a); d=a or g or t/u (not c); h=a or c or t/u (not g); v=a or g or c (not t, not u); and n=a or g or c or t/u (unknown, or other; any.)

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

| Table 2 of the Specification | | | | |
|---|---|---|---|---|
| Locus/ Display Name (1) | Source (2) | Start Base (3) | End Base (4) | ADDITTIONAL LOCUS INFORMATION (5) |
| asmbl_11856 | Vigna_unguiculata | 16426 | 16586 | NA |
| TA2790_3886 | Phaseolus_coccineus_release_2 | 16423 | 17393 | ADP-ribosylation factor [*Vigna unguiculata* (Cowpea)] |
| TA43459_3847 | Glycine_max_release_2 | 16434 | 18055 | ADP-ribosylation factor 1 [*Oryza sativa* (Rice)] |
| TC276541 | GMGI.071508 | 16434 | 18076 | UniRef100_P36397 Cluster: ADP-ribosylation factor 1; n = 1; *Arabidopsis thaliana*|Rep: ADP-ribosylation factor 1 - *Arabidopsis thaliana* (Mouse-ear cress) = partial (38%) |
| CD392203 | Glycine_max_release_2 | 16216 | 18687 | ADP-ribosylation factor [*Glycine max* (Soybean)] |
| BQ610865 | Glycine_max_release_2 | 16327 | 18667 | ADP-ribosylation factor 1 [*Oryza sativa* (Rice)] |
| EH046324 | Arachis_stenosperma_release_5 | 16405 | 18745 | Cluster: ADP-ribosylation factor 1, n = 1, *Arabidopsis thaliana*|Rep: ADP-ribosylation factor 1 - *Arabidopsis thaliana* (Mouse-ear cress) |
| AW202311 | Glycine_max_release_2 | 16378 | 19070 | ADP-ribosylation factor [*Glycine max* (Soybean)] |
| TC242702 | GMGI.071508 | 16234 | 20195 | UniRef100_Q38JU3 Cluster: ADP ribosylation factor 002; n = 2; core eudicotyledons|Rep: ADP ribosylation factor 002 - *Daucus carota* (Carrot) = complete |
| BI321678 | Glycine_max_release_2 | 17384 | 19066 | ADP-ribosylation factor [*Zea mays* (Maize)] |
| AW348317 | Glycine_max_release_2 | 16355 | 20097 | ADP-ribosylation factor [*Glycine max* (Soybean)] |
| EH042959 | Arachis_stenosperma_release_5 | 16401 | 20182 | Cluster: ADP-ribosylation factor 1, n = 2, *Medicago*|Rep: ADP-ribosylation factor 1 - *Medicago truncatula* (Barrel medic) |
| TC20337 | LJGI.070108 | 16420 | 20191 | UniRef100_Q5QQ33 Cluster: ADP-ribosylation factor 1, n = 2, *Medicago*|Rep: ADP-ribosylation factor 1 - *Medicago truncatula* (Barrel medic), complete |
| EH047563 | Arachis_stenosperma_release_5 | 16430 | 20182 | Cluster: ADP-ribosylation factor 1, n = 2, *Medicago*|Rep: ADP-ribosylation factor 1 - *Medicago truncatula* (Barrel medic) |
| TA2789_3886 | Phaseolus_coccineus_release_2 | 16436 | 20196 | ADP-ribosylation factor 1-like protein [*Solanum tuberosum* (Potato)] |
| TA43462_3847 | Glycine_max_release_2 | 16229 | 20438 | ADP-ribosylation factor [*Medicago sativa* (Alfalfa)] |
| TA1120_34305 | Lotus_japonicus_release_1 | 16522 | 20191 | ADP-ribosylation factor [*Medicago sativa* (Alfalfa)] |
| TA2306_3848 | Glycine_soja_release_2 | 16442 | 20440 | ADP-ribosylation factor [*Medicago sativa* (Alfalfa)] |
| TC273941 | GMGI.071508 | 16426 | 20464 | homologue to UniRef100_Q38JU3 Cluster: ADP ribosylation factor 002; n = 2; core eudicotyledons|Rep: ADP ribosylation factor 002 - *Daucus carota* (Carrot) = complete |
| TC238119 | GMGI.071508 | 16455 | 20449 | UniRef100_Q38JU3 Cluster: ADP ribosylation factor 002; n = 2; core eudicotyledons|Rep: ADP ribosylation factor 002 - |

Table 2 of the Specification

| Locus/ Display Name (1) | Source (2) | Start Base (3) | End Base (4) | ADDITIONAL LOCUS INFORMATION (5) |
|---|---|---|---|---|
| EG373880 | Arachis_hypogaea_release_5 | 17101 | 20182 | *Daucus carota* (Carrot) = complete Cluster: ADP-ribosylation factor 1, n = 2, *Medicago*\|Rep: ADP-ribosylation factor 1 - *Medicago truncatula* (Barrel medic) |
| BF066818 | Glycine_max_release_2 | 17081 | 20378 | ADP-ribosylation factor 1 [*Populus tomentosa*] |
| BF596154 | Glycine_max_release_2 | 17083 | 20397 | ADP-ribosylation factor [*Hyacinthus orientalis* (Common hyacinth)] |
| AW760997 | Glycine_max_release_2 | 17116 | 20397 | ADP-ribosylation factor [*Hyacinthus orientalis* (Common hyacinth)] |
| BF424079 | Glycine_max_release_2 | 17112 | 20417 | ADP-ribosylation factor [*Hyacinthus orientalis* (Common hyacinth)] |
| AW596022 | Glycine_max_release_2 | 17121 | 20415 | ADP-ribosylation factor 1 [*Populus tomentosa*] |
| TA43446_3847 | Glycine_max_release_2 | 17106 | 20436 | ADP-ribosylation factor [*Hyacinthus orientalis* (Common hyacinth)] |
| TA43455_3847 | Glycine_max_release_2 | 17125 | 20452 | ADP-ribosylation factor [*Hyacinthus orientalis* (Common hyacinth)] |
| BW595867 | Lotus_japonicus_release_1 | 17418 | 20191 | ADP-ribosylation factor [*Hyacinthus orientalis* (Common hyacinth)] |
| AW507598 | Glycine_max_release_2 | 17343 | 20437 | ADP-ribosylation factor [*Hyacinthus orientalis* (Common hyacinth)] |
| TA43447_3847 | Glycine_max_release_2 | 17343 | 20445 | ADP-ribosylation factor [*Hyacinthus orientalis* (Common hyacinth)] |
| TA43448_3847 | Glycine_max_release_2 | 17355 | 20438 | ADP-ribosylation factor 1 [*Populus tomentosa*] |
| AW596189 | Glycine_max_release_2 | 17358 | 20442 | ADP-ribosylation factor 1 [*Populus tomentosa*] |
| BI469983 | Glycine_max_release_2 | 17410 | 20438 | ADP-ribosylation factor 1 [*Populus tomentosa*] |
| AW472058 | Glycine_max_release_2 | 18655 | 20160 | ADP-ribosylation factor 1 [*Daucus carota* (Carrot)] |
| CB063805 | Glycine_max_release_2 | 18623 | 20432 | ADP-ribosylation factor 1 [*Populus tomentosa*] |
| BM891090 | GMGI.071508 | 18995 | 20429 | homologue to UniRef100_A7PRL9 Cluster: Chromosome chr14 scaffold_27 = whole genome shotgun sequence; n = 1; *Vitis vinifera*\|Rep: Chromosome chr14 scaffold_27 = whole genome shotgun sequence - *Vitis vinifera* (Grape) = partial (42%) |
| BM731935 | Glycine_max_release_2 | 19949 | 20444 | ADP-ribosylation factor 1 [*Populus tomentosa*] |
| AW695591 | MTGI.071708 | 30054 | 31388 | similar to UniRef100_Q40542 Cluster: NPK2, n = 1, *Nicotiana tabacum*\|Rep: NPK2 - *Nicotiana tabacum* (Common tobacco), partial (35%) |
| TC130040 | MTGI.071708 | 30054 | 31482 | similar to UniRef100_A7PM42 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (30%) |

Table 2 of the Specification

| Locus/ Display Name (1) | Source (2) | Start Base (3) | End Base (4) | ADDITIONAL LOCUS INFORMATION (5) |
|---|---|---|---|---|
| TC122822 | MTGI.071708 | 30054 | 34162 | Protein kinase, Nuclear transport factor 2 |
| Pvcon9203 | Phaseolus_vulgaris | 31194 | 34247 | UniRef100_A7PM42 Chromosome chr14 scaffold_21, whole genome shotgun sequence n = 1 Tax = *Vitis vinifera* RepID = A7PM42_VITVI E-0 |
| TA66103_3847 | Glycine_max_release_2 | 31879 | 34559 | Protein kinase; Nuclear transport factor 2 [*Medicago truncatula* (Barrel medic)] |
| CA801261 | GMGI.071508 | 33896 | 34304 | similar to UniRef100_Q40542 Cluster: NPK2; n = 1; *Nicotiana tabacum*|Rep: NPK2 - *Nicotiana tabacum* (Common tobacco) = partial (16%) |
| TC120073 | MTGI.071708 | 35367 | 38178 | Glycoside hydrolase, family 28 |
| NP004759 | GMGI.071508 | 34976 | 39622 | GB|AF128266.1|AAD46483.1 polygalacturonase PG1 |
| AF128266 | Glycine_max_release_2 | 34980 | 39622 | Polygalacturonase PG1 [*Glycine max* (Soybean)] |
| TA69799_3847 | Glycine_max_release_2 | 58988 | 65870 | Ubiquitin-associated [*Medicago truncatula* (Barrel medic)] |
| TA7619_47247 | Lotus_corniculatus_release_1 | 63855 | 65940 | Putative DNA cytosine methyltransferase Zmet3 related cluster |
| TA8711_34305 | Lotus_japonicus_release_1 | 63855 | 65940 | UBA-like [*Medicago truncatula* (Barrel medic)] |
| TC34762 | LJGI.070108 | 65619 | 65940 | NA |
| Pvcon5587 | Phaseolus_vulgaris | 65216 | 67090 | UniRef100_A7PM76 Chromosome chr14 scaffold_21, whole genome shotgun sequence n = 1 Tax = *Vitis vinifera* RepID = A7PM76_VITVI E-0 |
| TA5046_3885 | Phaseolus_vulgaris_release_2 | 65808 | 67002 | UBA-like [*Medicago truncatula* (Barrel medic)] |
| asmbl_11857 | Vigna_unguiculata | 65951 | 67042 | NA |
| TA58707_3847 | Glycine_max_release_2 | 66006 | 67253 | UBA-like [*Medicago truncatula* (Barrel medic)] |
| TC241193 | GMGI.071508 | 66006 | 67253 | similar to UniRef100_A7PM76 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (38%) |
| BI967232 | Glycine_max_release_2 | 66170 | 67203 | UBA-like [*Medicago truncatula* (Barrel medic)] |
| AV417590 | LJGI.070108 | 66745 | 67090 | similar to UniRef100_A7PM76 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (19%) |
| AV768315 | Lotus_japonicus_release_1 | 66699 | 67155 | UBA-like [*Medicago truncatula* (Barrel medic)] |
| TC32114 | LJGI.070108 | 66699 | 67275 | similar to UniRef100_Q76KU6 Cluster: DNA methyltransferase, n = 1, *Nicotiana tabacum*|Rep: DNA methyltransferase - *Nicotiana tabacum* (Common tobacco), partial (20%) |
| TA1535_34305 | Lotus_japonicus_release_1 | 66745 | 67277 | UBA-like [*Medicago truncatula* (Barrel medic)] |
| TA2793_47247 | Lotus_corniculatus_release_1 | 66745 | 67277 | DNA methyltransferase related cluster |

-continued

Table 2 of the Specification

| Locus/ Display Name (1) | Source (2) | Start Base (3) | End Base (4) | ADDITTIONAL LOCUS INFORMATION (5) |
|---|---|---|---|---|
| AV768911 | Lotus_japonicus_release_1 | 66943 | 67155 | Ubiquitin-associated [*Medicago truncatula* (Barrel medic)] |
| CB540531 | Phaseolus_vulgaris | 73267 | 73561 | UniRef100_A7PM74 Chromosome chr14 scaffold_21, whole genome shotgun sequence n = 1 Tax = *Vitis vinifera* RepID = A7PM74_VITVI 5.00E−27 |
| BE347690 | GMGI.071508 | 73509 | 73770 | similar to UniRef100_Q5VQL1-2 Cluster: Isoform 2 of Q5VQL1; n = 1; *Oryza sativa Japonica* Group\|Rep: Isoform 2 of Q5VQL1 - *Oryza sativa* subsp. *japonica* (Rice) = partial (5%) |
| BE347690 | Glycine_max_release_2 | 73509 | 73822 | WW/Rsp5/WWP; Helicase = C-terminal [*Medicago truncatula* (Barrel medic)] |
| BE608496 | GMGI.071508 | 73444 | 73947 | similar to UniRef100_A7PM74 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (16%) |
| AI416763 | GMGI.071508 | 74073 | 74520 | similar to UniRef100_Q9SP26 Cluster: P72 DEAD box protein; n = 1; *Pisum sativum*\|Rep: P72 DEAD box protein - *Pisum sativum* (Garden pea) = partial (16%) |
| AI416763 | Glycine_max_release_2 | 74073 | 74743 | ATP-dependent RNA helicase-like protein DB10 [*Nicotiana sylvestris* (Wood tobacco)] |
| BW615083 | LJGI.070108 | 74256 | 74855 | similar to UniRef100_A7PM74 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (24%) |
| TA8332_34305 | Lotus_japonicus_release_1 | 74256 | 75446 | WW/Rsp5/WWP, Helicase, C-terminal [*Medicago truncatula* (Barrel medic)] |
| TC27807 | LJGI.070108 | 74343 | 75446 | similar to UniRef100_Q9SP26 Cluster: P72 DEAD box protein, n = 1, *Pisum sativum*\|Rep: P72 DEAD box protein - *Pisum sativum* (Garden pea), partial (34%) |
| asmbl_11858 | Vigna_unguiculata | 75228 | 75500 | NA |
| TA60825_3847 | Glycine_max_release_2 | 74963 | 75981 | P72 DEAD box protein [*Pisum sativum* (Garden pea)] |
| TC249436 | GMGI.071508 | 74985 | 75966 | similar to UniRef100_Q9SP26 Cluster: P72 DEAD box protein; n = 1; *Pisum sativum*\|Rep: P72 DEAD box protein - *Pisum sativum* (Garden pea) = partial (12%) |
| TC269249 | GMGI.071508 | 86882 | 87576 | similar to UniRef100_A7PM72 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (42%) |

-continued

Table 2 of the Specification

| Locus/ Display Name (1) | Source (2) | Start Base (3) | End Base (4) | ADDITIONAL LOCUS INFORMATION (5) |
|---|---|---|---|---|
| TA64136_3847 | Glycine_max_release_2 | 86882 | 89066 | Putative phosphate/phosphoenolpyruvate translocator [*Arabidopsis thaliana* (Mouse-ear cress)] |
| CO982132 | Glycine_max_release_2 | 87225 | 91497 | Phosphate/phosphoenolpyruvate translocator [*Nicotiana tabacum* (Common tobacco)] |
| TC274531 | GMGI.071508 | 87225 | 91497 | similar to UniRef100_A4UTS3 Cluster: Chloroplast phosphoenolpyruvate/phosphate translocator; n = 1; *Pisum sativum*|Rep: Chloroplast phosphoenolpyruvate/phosphate translocator - *Pisum sativum* (Garden pea) = partial (53%) |
| Pvcon2802 | Phaseolus_vulgaris | 87119 | 92616 | UniRef100_A9PD12 Putative uncharacterized protein n = 1 Tax = *Populus trichocarpa* RepID = A9PD12_POPTR 1.00E−121 |
| TA4406_3885 | Phaseolus_vulgaris_release_2 | 89055 | 92616 | Phosphate/phosphoenolpyruvate translocator [*Nicotiana tabacum* (Common tobacco)] |
| TA74766_3847 | Glycine_max_release_2 | 91397 | 92725 | Phosphoenolpyruvate/phosphate translocator [*Mesembryanthemum crystallinum* (Common ice plant)] |
| TC265023 | GMGI.071508 | 91686 | 92725 | similar to UniRef100_A7PM71 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (15%) |
| M0205928 | SEQ. LISTING | 92718 | 92334 | SEQ ID NO: 3 |
| BG406195 | GMGI.071508 | 107039 | 107366 | (SEQ ID NO: 13) |
| BG406195 | Glycine_max_release_2 | 107039 | 107375 | NA |
| M0101742 | SEQ. LISTING | 112189 | 113483 | SEQ ID NO: 5 |
| BG550728 | GMGI.071508 | 112663 | 113757 | weakly similar to UniRef100_A7PM60 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (13%) |
| BG550728 | Glycine_max_release_2 | 112663 | 113867 | Receptor-like serine/threonine kinase [*Arabidopsis thaliana* (Mouse-ear cress)] |
| CV535605 | Phaseolus_vulgaris | 112548 | 113982 | UniRef100_A7PM60 Chromosome chr14 scaffold_21, whole genome shotgun sequence n = 1 Tax = *Vitis vinifera* RepID = A7PM60_VITVI 9.00E−79 |
| M0129138 | SEQ. LISTING | 114532 | 113494 | SEQ ID NO: 4 |
| BU551345 | Glycine_max_release_2 | 115956 | 116339 | (SEQ ID NO: 16) |
| TA58315_3847 | Glycine_max_release_2 | 118318 | 120087 | NA |
| TC236438 | GMGI.071508 | 118318 | 120087 | NA |
| BE611751 | Glycine_max_release_2 | 119165 | 119645 | NA |
| BE611751 | GMGI.071508 | 119229 | 119645 | NA |
| TA70371_3847 | Glycine_max_release_2 | 137417 | 137864 | Hypothetical protein [*Medicago truncatula* (Barrel medic)] |

Table 2 of the Specification

| Locus/ Display Name (1) | Source (2) | Start Base (3) | End Base (4) | ADDITTIONAL LOCUS INFORMATION (5) |
|---|---|---|---|---|
| TC267549 | GMGI.071508 | 137417 | 137864 | similar to UniRef100_Q9FI64 Cluster: Genomic DNA = chromosome 5 = TAC clone: K21I16; n = 1; *Arabidopsis thaliana*\|Rep: Genomic DNA = chromosome 5 = TAC clone: K21I16 - *Arabidopsis thaliana* (Mouse-ear cress) = partial (43%) |
| BG156330 | GMGI.071508 | 155872 | 156903 | similar to UniRef100_A7PM41 Cluster: Chromosome chr14 scaffold_21 = whole genome shotgun sequence; n = 2; *Vitis vinifera*\|Rep: Chromosome chr14 scaffold_21 = whole genome shotgun sequence - *Vitis vinifera* (Grape) = partial (23%) |
| BG156330 | Glycine_max_release_2 | 155872 | 157058 | WD40-like [*Medicago truncatula* (Barrel medic)] |
| Pvcon10326 | Phaseolus_vulgaris | 155691 | 157835 | UniRef100_A7PM41 Chromosome chr14 scaffold_21, whole genome shotgun sequence n = 1 Tax = *Vitis vinifera* RepID = A7PM41_VITVI 3.00E−93 |
| CD397113 | Glycine_max_release_2 | 157474 | 157813 | NA |
| TA12653_34305 | Lotus_japonicus_release_1 | 159489 | 161341 | NADP-specific isocitrate dehydrogenase [*Lupinus albus* (White lupin)] |
| TC27381 | LJGI.070108 | 159489 | 161341 | similar to UniRef100_Q7Y0W7 Cluster: NADP-specific isocitrate dehydrogenase, n = 1, *Lupinus albus*\|Rep: NADP-specific isocitrate dehydrogenase - *Lupinus albus* (White lupin), partial (25%) |
| DT084057 | Glycine_soja_release_2 | 161638 | 162192 | NADP-specific isocitrate dehydrogenase [*Lupinus albus* (White lupin)] |
| BE661051 | Glycine_max_release_2 | 170271 | 172034 | Cyclin-like F-box [*Medicago truncatula* (Barrel medic)] |
| TA11305_34305 | Lotus_japonicus_release_1 | 170700 | 172307 | Cyclin-like F-box [*Medicago truncatula* (Barrel medic)] |
| TC34049 | LJGI.070108 | 170700 | 172307 | similar to UniRef100_A7PF14 Cluster: Chromosome chr11 scaffold_13, whole genome shotgun sequence, n = 1, *Vitis vinifera*\|Rep: Chromosome chr11 scaffold_13, whole genome shotgun sequence - *Vitis vinifera* (Grape), partial (32%) |
| NP7256876 | MTGI.071708 | 171929 | 173188 | GB\|AC157983.16\|ABE86510.1 Cyclin-like F-box |
| TA68495_3847 | Glycine_max_release_2 | 194920 | 195696 | Oleosin [*Sesamum indicum* (Oriental sesame) (Gingelly)] |
| TC265354 | GMGI.071508 | 194920 | 195696 | weakly similar to UniRef100_P29530 Cluster: P24 oleosin isoform A; n = 1; *Glycine max*\|Rep: P24 oleosin isoform A - *Glycine max* (Soybean) = partial (40%) |
| BE658264 | Glycine_max_release_2 | 195176 | 195925 | Oleosin [*Sesamum indicum* (Oriental sesame) (Gingelly)] |
| CV539661 | Phaseolus_vulgaris | 217885 | 218101 | No significant hit (e−20) |
| CA912681 | Phaseolus_coccineus_release_2 | 220374 | 220748 | *Arabidopsis thaliana* genomic DNA, chromosome 3, P1 clone: MGF10 [*Arabidopsis thaliana* (Mouse-ear cress)] |

-continued

Table 2 of the Specification

| Locus/ Display Name (1) | Source (2) | Start Base (3) | End Base (4) | ADDITIONAL LOCUS INFORMATION (5) |
|---|---|---|---|---|
| CA785107 | Glycine_soja_release_2 | 221393 | 221885 | NA |
| TC276537 | GMGI.071508 | 221407 | 222104 | weakly similar to UniRef100_Q4RYK7 Cluster: Chromosome 3 SCAF14975 = whole genome shotgun sequence; n = 1; *Tetraodon nigroviridis*|Rep: Chromosome 3 SCAF14975 = whole genome shotgun sequence - *Tetraodon nigroviridis* (Green puffer) = partial (21%) |
| TA71044_3847 | Glycine_max_release_2 | 221407 | 222133 | NA |
| CD406643 | Glycine_max_release_2 | 222113 | 222297 | NA |
| AV416316 | LJGI.070108 | 223773 | 223869 | similar to UniRef100_A7PM35 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (9%) |
| EC911350 | Phaseolus_vulgaris | 224587 | 225958 | UniRef100_A5C233 Putative uncharacterized protein n = 1 Tax = *Vitis vinifera* RepID = A5C233_VITVI 3.00E−77 |
| BU760697 | GMGI.071508 | 224857 | 225965 | similar to UniRef100_A7PM35 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (22%) |
| BU760697 | Glycine_max_release_2 | 224857 | 226145 | Protein At5g19130 [*Arabidopsis thaliana* (Mouse-ear cress)] |
| TC119982 | MTGI.071708 | 224248 | 226812 | Gaa1-like, GPI transamidase component |
| CV541515 | Phaseolus_vulgaris | 225934 | 226374 | UniRef100_A7PM35 Chromosome chr14 scaffold_21, whole genome shotgun sequence n = 1 Tax = *Vitis vinifera* RepID = A7PM35_VITVI 2.00E−34 |
| TA76349_3847 | Glycine_max_release_2 | 226118 | 226768 | Protein At5g19130 [*Arabidopsis thaliana* (Mouse-ear cress)] |
| TA12045_47247 | Lotus_corniculatus_release_1 | 226354 | 226789 | GPAA1-like protein related cluster |
| TA13675_34305 | Lotus_japonicus_release_1 | 226354 | 226789 | Protein At5g19130 [*Arabidopsis thaliana* (Mouse-ear cress)] |
| TC29330 | LJGI.070108 | 226354 | 226789 | similar to UniRef100_A7PM35 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (13%) |
| NP7254537 | MTGI.071708 | 233411 | 237212 | GB|AC152349.11|ABP03404.1 Protein of unknown function DUF266, plant |
| EH256962 | GMGI.071508 | 235306 | 237649 | similar to UniRef100_A7PM54 Cluster: Chromosome chr14 scaffold_21 = whole genome shotgun sequence; n = 1; *Vitis vinifera*|Rep: Chromosome chr14 scaffold_21 = whole |

Table 2 of the Specification

| Locus/ Display Name (1) | Source (2) | Start Base (3) | End Base (4) | ADDITIONAL LOCUS INFORMATION (5) |
|---|---|---|---|---|
| | | | | genome shotgun sequence - *Vitis vinifera* (Grape) = partial (33%) |
| CX708677 | Glycine_max_release_2 | 247269 | 248145 | NA |
| BW599077 | LJGI.070108 | 255475 | 261945 | similar to UniRef100_A7QD90 Cluster: Peptidyl-prolyl cis-trans isomerase, n = 1, *Vitis vinifera*\|Rep: Peptidyl-prolyl cis-trans isomerase - *Vitis vinifera* (Grape), partial (18%) |
| BW625918 | LJGI.070108 | 257810 | 262980 | similar to UniRef100_Q93YQ8 Cluster: Peptidyl-prolyl cis-trans isomerase, n = 1, *Arabidopsis thaliana*\|Rep: Peptidyl-prolyl cis-trans isomerase - *Arabidopsis thaliana* (Mouse-ear cress), partial (32%) |
| DT083826 | Glycine_soja_release_2 | 260886 | 261121 | NA |
| CB063628 | GMGI.071508 | 271592 | 271900 | similar to UniRef100_A7PM52 Cluster: Chromosome chr14 scaffold_21 whole genome shotgun sequence; n = 1; *Vitis vinifera*\|Rep: = partial (2%) |
| CB063628 | Glycine_max_release_2 | 271592 | 271928 | NA |
| TA5835_34305 | Lotus_japonicus_release_1 | 273868 | 275906 | Vegetative cell wall protein gp1-like [*Oryza sativa* (japonica cultivar-group)] |
| TC32024 | LJGI.070108 | 275152 | 275906 | similar to UniRef100_A7PM52 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (9%) |
| TC252667 | GMGI.071508 | 275739 | 276506 | similar to UniRef100_A7PM52 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (12%) |
| AW311416 | Glycine_max_release_2 | 276269 | 276455 | NA |
| WmFPC_Contig850 | | 99810 | 475910 | NA |
| CV534998 | Phaseolus_vulgaris | 288050 | 288585 | UniRef100_A7PM50 Chromosome chr14 scaffold_21, whole genome shotgun sequence n = 1 Tax = *Vitis vinifera* RepID = A7PM50_VITVI 6.00E−39 |
| TA75806_3847 | Glycine_max_release_2 | 288290 | 290376 | *Arabidopsis thaliana* genomic DNA = chromosome 3 = P1 clone: MGF10 [*Arabidopsis thaliana* (Mouse-ear cress)] |
| TC276120 | GMGI.071508 | 288290 | 290376 | similar to UniRef100_A7PM50 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (62%) |
| BI786388 | GMGI.071508 | 291666 | 292088 | similar to UniRef100_A7PM49 Cluster: Chromosome chr14 scaffold_21 = whole genome shotgun sequence; n = 1; *Vitis vinifera*\|Rep: Chromosome |

-continued

Table 2 of the Specification

| Locus/ Display Name (1) | Source (2) | Start Base (3) | End Base (4) | ADDITTIONAL LOCUS INFORMATION (5) |
|---|---|---|---|---|
| | | | | chr14 scaffold_21 = whole genome shotgun sequence - *Vitis vinifera* (Grape) = partial (7%) |
| BI786388 | Glycine_max_release_2 | 291666 | 292099 | NA |
| TA63308_3847 | Glycine_max_release_2 | 291633 | 294397 | NA |
| TC243765 | GMGI.071508 | 293681 | 294426 | weakly similar to UniRef100_Q0JDM0 Cluster: Os04g0394300 protein; n = 1; *Oryza sativa Japonica* Group\|Rep: Os04g0394300 protein - *Oryza sativa* subsp. *japonica* (Rice) = partial (3%) |
| TA6412_34305 | Lotus_japonicus_release_1 | 293803 | 294412 | NA |
| TC24112 | LJGI.070108 | 293803 | 294412 | NA |
| CA899930 | Phaseolus_coccineus_release_2 | 294054 | 294263 | NA |
| TA3887_3886 | Phaseolus_coccineus_release_2 | 302301 | 303033 | Hypothetical protein MJH23.3 [*Arabidopsis thaliana* (Mouse-ear cress)] |
| AW705271 | Glycine_max_release_2 | 302299 | 303855 | Hypothetical protein MJH23.3 [*Arabidopsis thaliana* (Mouse-ear cress)] |
| TC237313 | GMGI.071508 | 303227 | 306007 | similar to UniRef100_A7PM30 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (54%) |
| TA61594_3847 | Glycine_max_release_2 | 303227 | 306056 | Similarity to RNA binding protein [*Arabidopsis thaliana* (Mouse-ear cress)] |
| asmbl_11859 | Vigna_unguiculata | 303952 | 305921 | NA |
| toGm05 | DAGchainer | 30059 | 580791 | Ks0.2335 |
| BU544029 | Glycine_max_release_2 | 305220 | 305762 | NA |
| TC23280 | LJGI.070108 | 305373 | 305839 | similar to UniRef100_A7PM30 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (17%) |
| AI461058 | Glycine_max_release_2 | 305614 | 305834 | NA |
| BE555571 | Glycine_max_release_2 | 305656 | 306011 | NA |
| asmbl_11860 | Vigna_unguiculata | 319622 | 320527 | NA |
| EV270366 | GMGI.071508 | 319893 | 320575 | similar to UniRef100_P15792 Cluster: Protein kinase PVPK-1; n = 1; *Phaseolus vulgaris*\|Rep: Protein kinase PVPK-1 - *Phaseolus vulgaris* (Kidney bean) (French bean) = partial (34%) |
| J04555 | Phaseolus_vulgaris_release_2 | 318937 | 322709 | Protein kinase PVPK-1 [*Phaseolus vulgaris* (Kidney bean) (French bean)] |
| TA11578_34305 | Lotus_japonicus_release_1 | 320355 | 322024 | Protein kinase PVPK-1 [*Phaseolus vulgaris* (Kidney bean) (French bean)] |
| TC35252 | LJGI.070108 | 320355 | 322381 | homologue to UniRef100_P15792 Cluster: Protein kinase PVPK-1, n = 1, *Phaseolus vulgaris*\|Rep: Protein kinase PVPK-1 - *Phaseolus vulgaris* (Kidney bean) (French bean), partial (48%) |
| Pvcon4227 | Phaseolus_vulgaris | 320098 | 322709 | UniRef100_P15792 Protein kinase PVPK-1 n = 1 Tax = *Phaseolus vulgaris* RepID = KPK1_PHAVU E-0 |

Table 2 of the Specification

| Locus/Display Name (1) | Source (2) | Start Base (3) | End Base (4) | ADDITTIONAL LOCUS INFORMATION (5) |
|---|---|---|---|---|
| CA900819 | Phaseolus_coccineus_release_2 | 325129 | 325547 | Sucrase-like protein [*Arabidopsis thaliana* (Mouse-ear cress)] |
| CA900820 | Phaseolus_coccineus_release_2 | 325119 | 328122 | AT3g27570/MMJ24_12 [*Arabidopsis thaliana* (Mouse-ear cress)] |
| TC269193 | GMGI.071508 | 325136 | 329359 | weakly similar to UniRef100_A7PM27 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (47%) |
| TA4354_3885 | Phaseolus_vulgaris_release_2 | 325476 | 329154 | AT5g40510/MNF13_30 [*Arabidopsis thaliana* (Mouse-ear cress)] |
| asmbl_11861 | Vigna_unguiculata | 326881 | 329154 | NA |
| CF920945 | Glycine_max_release_2 | 326967 | 329359 | AT3g27570/MMJ24_12 [*Arabidopsis thaliana* (Mouse-ear cress)] |
| SATT723 | | 337605 | 337828 | |
| Satt723 | ePCR | 337605 | 337828 | Map3.0 SSR L/Gm19 cM: 1.5 |
| TC244213 | GMGI.071508 | 354373 | 354996 | similar to UniRef100_A7PL06 Cluster: Chromosome chr7 scaffold_20 = whole genome shotgun sequence; n = 1; *Vitis vinifera*|Rep: Chromosome chr7 scaffold_20 = whole genome shotgun sequence - *Vitis vinifera* (Grape) = partial (17%) |
| BU090380 | Glycine_max_release_2 | 354683 | 354871 | NA |
| BP058294 | Lotus_japonicus_release_1 | 355950 | 356319 | Protein ycf2 [*Lotus japonicus*] |
| Pvcon2444 | Phaseolus_vulgaris | 354593 | 360732 | UniRef100_A7PL07 Chromosome chr7 scaffold_20, whole genome shotgun sequence n = 1 Tax = *Vitis vinifera* RepID = A7PL07_VITVI 1.00E−144 |
| asmbl_11862 | Vigna_unguiculata | 359273 | 359896 | NA |
| CA800649 | Glycine_max_release_2 | 377994 | 379933 | AT3g01590/F4P13_13 [*Arabidopsis thaliana* (Mouse-ear cress)] |
| TC245493 | GMGI.071508 | 377994 | 381638 | similar to UniRef100_A7PM21 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (96%) |
| CO984617 | Glycine_max_release_2 | 379899 | 381537 | At5g14500 [*Arabidopsis thaliana* (Mouse-ear cress)] |
| M0114388 | SEQ. LISTING | 381308 | 380486 | SEQ ID NO: 2 |
| AW704585 | Glycine_max_release_2 | 381210 | 381673 | At5g14500 [*Arabidopsis thaliana* (Mouse-ear cress)] |
| TC248588 | GMGI.071508 | 383419 | 383857 | NA |
| asmbl_11863 | Vigna_unguiculata | 383428 | 384088 | NA |
| TC126554 | MTGI.071708 | 383593 | 384668 | weakly similar to UniRef100_Q940C3 Cluster: AT3g27530/MMJ24_7, n = 2, *Arabidopsis thaliana*|Rep: AT3g27530/MMJ24_7 - *Arabidopsis thaliana* (Mouse-ear cress), partial (38%) |
| AJ002216 | Pisum_sativum_release_2 | 384088 | 384751 | Emb|CAA07228.1 [*Arabidopsis thaliana* (Mouse-ear cress)] |

Table 2 of the Specification

| Locus/ Display Name (1) | Source (2) | Start Base (3) | End Base (4) | ADDITTIONAL LOCUS INFORMATION (5) |
|---|---|---|---|---|
| BI702257 | GMGI.071508 | 384067 | 384789 | similar to UniRef100_Q940C3 Cluster: AT3g27530/MMJ24_7; n = 2; *Arabidopsis thaliana*\|Rep: AT3g27530/MMJ24_7 - *Arabidopsis thaliana* (Mouse-ear cress) = partial (14%) |
| BG451913 | MTGI.071708 | 386353 | 388007 | similar to UniRef100_Q9LT59 Cluster: Emb\|CAA07228.1, n = 1, *Arabidopsis thaliana*\|Rep: Emb\|CAA07228.1 - *Arabidopsis thaliana* (Mouse-ear cress), partial (19%) |
| CV533025 | Phaseolus_vulgaris | 388647 | 389345 | UniRef100_UPI000016357E GC6 (GOLGIN CANDIDATE 6) binding/protein transporter Tax = n = 1 RepID = UPI000016357E 6.00E−27 |
| AV777312 | LJGI.070108 | 389152 | 391279 | similar to UniRef100_Q9LT59 Cluster: Emb\|CAA07228.1, n = 1, *Arabidopsis thaliana*\|Rep: Emb\|CAA07228.1 - *Arabidopsis thaliana* (Mouse-ear cress), partial (19%) |
| BM187543 | GMGI.071508 | 394984 | 395407 | similar to UniRef100_A7PM13 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (36%) |
| BM187543 | Glycine_max_release_2 | 394984 | 395559 | Gb\|AAF01546.1 [*Arabidopsis thaliana* (Mouse-ear cress)] |
| DN652256 | LJGI.070108 | 395487 | 395708 | similar to UniRef100_A7P4B1 Cluster: Chromosome chr1 scaffold_5, whole genome shotgun sequence, n = 1, *Vitis vinifera*\|Rep: Chromosome chr1 scaffold_5, whole genome shotgun sequence - *Vitis vinifera* (Grape), partial (19%) |
| DT044393 | Arachis_hypogaea_release_5 | 395462 | 395746 | Cluster: Hypothetical protein T23K23.27, n = 1, *Arabidopsis thaliana*\|Rep: Hypothetical protein T23K23.27 - *Arabidopsis thaliana* (Mouse-ear cress) |
| FD789910 | Phaseolus_vulgaris | 395555 | 395927 | UniRef100_A7P4B1 Chromosome chr1 scaffold_5, whole genome shotgun sequence n = 1 Tax = *Vitis vinifera* RepID = A7P4B1_VITVI 2.00E−59 |
| EH259382 | GMGI.071508 | 395577 | 396156 | similar to UniRef100_A7PM13 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (34%) |
| TA69305_3847 | Glycine_max_release_2 | 403237 | 404175 | NA |
| TC243910 | GMGI.071508 | 403237 | 404175 | similar to UniRef100_A7PM14 Cluster: Chromosome chr14 scaffold_21 = whole genome shotgun sequence; n = 1; *Vitis vinifera*\|Rep: Chromosome chr14 scaffold_21 = whole |

Table 2 of the Specification

| Locus/ Display Name (1) | Source (2) | Start Base (3) | End Base (4) | ADDITTIONAL LOCUS INFORMATION (5) |
|---|---|---|---|---|
| | | | | genome shotgun sequence - *Vitis vinifera* (Grape) = partial (5%) |
| CA785084 | Glycine_soja_release_2 | 403526 | 404055 | NA |
| CV541170 | Phaseolus_vulgaris | 404688 | 406556 | UniRef100_Q9LT57 Emb\|CAB45506.1 n = 1 Tax = *Arabidopsis thaliana* RepID = Q9LT57_ARATH 1.00E−113 |
| BF071095 | GMGI.071508 | 406510 | 407127 | similar to UniRef100_Q9LT57 Cluster: Emb\|CAB45506.1; n = 1; *Arabidopsis thaliana*\|Rep: Emb\|CAB45506.1 - *Arabidopsis thaliana* (Mouse-ear cress) = partial (8%) |
| BF071095 | Glycine_max_release_2 | 406527 | 407127 | NA |
| BM270669 | Glycine_max_release_2 | 409910 | 410532 | NA |
| BM270669 | GMGI.071508 | 410045 | 410532 | similar to UniRef100_A7PM16 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (9%) |
| BG550673 | GMGI.071508 | 421541 | 422250 | similar to UniRef100_A7PM12 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (26%) |
| BG550673 | Glycine_max_release_2 | 421541 | 422354 | Hypothetical protein F18O22_260 [*Arabidopsis thaliana* (Mouse-ear cress)] |
| BU551363 | Glycine_max_release_2 | 422150 | 422745 | NA |
| CD407423 | Glycine_max_release_2 | 423719 | 423842 | NA |
| M0205350 | SEQ Listing | 424095 | 423776 | SEQ ID NO: 1 |
| EV270239 | GMGI.071508 | 425649 | 426181 | similar to UniRef100_Q0WVR7 Cluster: TRNA synthase-like protein; n = 1; *Arabidopsis thaliana*\|Rep: TRNA synthase-like protein - *Arabidopsis thaliana* (Mouse-ear cress) = partial (5%) |
| BI424448 | GMGI.071508 | 451332 | 451679 | similar to UniRef100_P82353 Cluster: Non-specific lipid-transfer protein 2; n = 1; *Prunus armeniaca*\|Rep: Non-specific lipid-transfer protein 2 - *Prunus armeniaca* (Apricot) = partial (68%) |
| TA49179_3847 | Glycine_max_release_2 | 451332 | 451827 | Nonspecific lipid-transfer protein 2 [*Prunus armeniaca* (Apricot)] |
| TC252453 | GMGI.071508 | 451397 | 451828 | weakly similar to UniRef100_Q43681 Cluster: Probable non-specific lipid-transfer protein AKCS9 precursor; n = 1; *Vigna unguiculata*\|Rep: Probable non-specific lipid-transfer protein AKCS9 precursor - *Vigna unguiculata* (Cowpea) = partial (86%) |
| BE609938 | Glycine_max_release_2 | 451607 | 451756 | Probable lipid transfer protein family protein [*Tamarix androssowii*] |

Table 2 of the Specification

| Locus/Display Name (1) | Source (2) | Start Base (3) | End Base (4) | ADDITTIONAL LOCUS INFORMATION (5) |
|---|---|---|---|---|
| BQ612382 | Glycine_max_release_2 | 451777 | 452217 | NA |
| NS0102027 | | 466228 | 466889 | |
| Pvcon7917 | Phaseolus_vulgaris | 466120 | 467338 | UniRef100_A5C9E2 Putative uncharacterized protein n = 1 Tax = *Vitis vinifera* RepID = A5C9E2_VITVI 6.00E−44 |
| asmbl_11864 | Vigna_unguiculata | 467520 | 468191 | NA |
| TA49596_3847 | Glycine_max_release_2 | 470086 | 472059 | Methionine aminopeptidase 2B [*Arabidopsis thaliana* (Mouse-ear cress)] |
| TC255857 | GMGI.071508 | 470086 | 476828 | homologue to UniRef100_A7PXX3 Cluster: Methionine aminopeptidase; n = 1; *Vitis vinifera*|Rep: Methionine aminopeptidase - *Vitis vinifera* (Grape) = partial (91%) |
| FD792539 | Phaseolus_vulgaris | 472774 | 475674 | UniRef100_A7PXX3 Methionine aminopeptidase n = 1 Tax = *Vitis vinifera* RepID = A7PXX3_VITVI 5.00E−56 |
| TA3829_3848 | Glycine_soja_release_2 | 471918 | 476623 | Methionine aminopeptidase 2B [*Arabidopsis thaliana* (Mouse-ear cress)] |
| BU765955 | Glycine_max_release_2 | 472787 | 475846 | Methionine aminopeptidase 2B [*Arabidopsis thaliana* (Mouse-ear cress)] |
| EG530516 | Arachis_hypogaea_release_5 | 472835 | 476690 | Cluster: Methionine aminopeptidase 2B, n = 1, *Arabidopsis thaliana*|Rep: Methionine aminopeptidase 2B - *Arabidopsis thaliana* (Mouse-ear cress) |
| AV425234 | LJGI.070108 | 475562 | 475924 | homologue to UniRef100_A7PXX3 Cluster: Methionine aminopeptidase, n = 1, *Vitis vinifera*|Rep: Methionine aminopeptidase - *Vitis vinifera* (Grape), partial (22%) |
| TA49598_3847 | Glycine_max_release_2 | 474794 | 476709 | Methionine aminopeptidase 2B [*Arabidopsis thaliana* (Mouse-ear cress)] |
| FD797260 | Phaseolus_vulgaris | 475768 | 476654 | UniRef100_A7PXX3 Methionine aminopeptidase n = 1 Tax = *Vitis vinifera* RepID = A7PXX3_VITVI 6.00E−55 |
| BE823844 | Glycine_max_release_2 | 475751 | 476828 | Methionine aminopeptidase 2B [*Arabidopsis thaliana* (Mouse-ear cress)] |
| BG726070 | Glycine_max_release_2 | 476668 | 476807 | NA |
| BQ080926 | GMGI.071508 | 480002 | 480636 | similar to UniRef100_A7PY54 Cluster: Chromosome chr15 scaffold_37 = whole genome shotgun sequence; n = 1; *Vitis vinifera*|Rep: Chromosome chr15 scaffold_37 = whole genome shotgun sequence - *Vitis vinifera* (Grape) = partial (39%) |
| TA69442_3847 | Glycine_max_release_2 | 480002 | 481069 | Hypothetical protein F22I13.40 [*Arabidopsis thaliana* (Mouse-ear cress)] |
| TC262427 | GMGI.071508 | 480002 | 481069 | similar to UniRef100_A7P8Q6 Cluster: Chromosome chr3 scaffold_8 = whole genome shotgun sequence; n = 1; *Vitis vinifera*|Rep: Chromosome chr3 scaffold_8 = whole genome shotgun sequence - *Vitis vinifera* (Grape) = partial (20%) |

Table 2 of the Specification

| Locus/ Display Name (1) | Source (2) | Start Base (3) | End Base (4) | ADDITIONAL LOCUS INFORMATION (5) |
|---|---|---|---|---|
| BU548976 | Glycine_max_release_2 | 481474 | 481970 | Multi antimicrobial extrusion protein MatE [*Medicago truncatula* (Barrel medic)] |
| CX547082 | Glycine_max_release_2 | 481345 | 482173 | Multi antimicrobial extrusion protein MatE [*Medicago truncatula* (Barrel medic)] |
| TC236122 | GMGI.071508 | 481300 | 482612 | NA |
| TA57759_3847 | Glycine_max_release_2 | 481300 | 482627 | Multi antimicrobial extrusion protein MatE [*Medicago truncatula* (Barrel medic)] |
| AV420909 | LJGI.070108 | 481846 | 482201 | weakly similar to UniRef100_A7QTE8 Cluster: Chromosome undetermined scaffold_167, whole genome shotgun sequence, n = 1, *Vitis vinifera*\|Rep: Chromosome undetermined scaffold_167, whole genome shotgun sequence - *Vitis vinifera* (Grape), partial (24%) |
| AW597322 | Glycine_max_release_2 | 481965 | 482825 | Multi antimicrobial extrusion protein MatE [*Medicago truncatula* (Barrel medic)] |
| BM270610 | Glycine_max_release_2 | 482034 | 483008 | Multi antimicrobial extrusion protein MatE [*Medicago truncatula* (Barrel medic)] |
| BI972603 | GMGI.071508 | 482632 | 483190 | weakly similar to UniRef100_A7P3G6 Cluster: Chromosome chr1 scaffold_5 = whole genome shotgun sequence; n = 1; *Vitis vinifera*\|Rep: Chromosome chr1 scaffold_5 = whole genome shotgun sequence - *Vitis vinifera* (Grape) = partial (20%) |
| BI972603 | Glycine_max_release_2 | 482632 | 484113 | Multi antimicrobial extrusion protein MatE [*Medicago truncatula* (Barrel medic)] |
| TA66198_3847 | Glycine_max_release_2 | 482595 | 484230 | Multi antimicrobial extrusion protein MatE [*Medicago truncatula* (Barrel medic)] |
| TC253566 | GMGI.071508 | 482648 | 484405 | weakly similar to UniRef100_A7QTE8 Cluster: Chromosome undetermined scaffold_167 = whole genome shotgun sequence; n = 1; *Vitis vinifera*\|Rep: Chromosome undetermined scaffold_167 = whole genome shotgun sequence - *Vitis vinifera* (Grape) = partial (44%) |
| asmbl_11865 | Vigna_unguiculata | 482937 | 484289 | NA |
| BG881371 | Glycine_max_release_2 | 483075 | 484230 | Multi antimicrobial extrusion protein MatE [*Medicago truncatula* (Barrel medic)] |
| WmFPC_Contig7443 | | 384071 | 598745 | NA |
| AW695419 | MTGI.071708 | 491367 | 494466 | similar to UniRef100_A7PU69 Cluster: Chromosome chr7 scaffold_31, whole genome shotgun sequence, n = 1, *Vitis vinifera*\|Rep: Chromosome chr7 scaffold_31, whole genome shotgun sequence - *Vitis vinifera* (Grape), partial (11%) |
| BF645755 | MTGI.071708 | 494870 | 497474 | similar to UniRef100_A7PU69 Cluster: Chromosome chr7 scaffold_31, whole genome shotgun sequence, n = 1, *Vitis vinifera*\|Rep: Chromosome chr7 scaffold_31, whole genome shotgun sequence - *Vitis vinifera* (Grape), partial (14%) |

Table 2 of the Specification

| Locus/ Display Name (1) | Source (2) | Start Base (3) | End Base (4) | ADDITTIONAL LOCUS INFORMATION (5) |
|---|---|---|---|---|
| BE475242 | GMGI.071508 | 497000 | 497327 | similar to UniRef100_A7NWE7 Cluster: Chromosome chr5 scaffold_2 whole genome shotgun sequence; n = 1; *Vitis vinifera*\|Rep: = partial (1%) |
| BE475242 | Glycine_max_release_2 | 497000 | 497549 | Hypothetical protein At3g23590/MDB19_8 [*Arabidopsis thaliana* (Mouse-ear cress)] |
| BW611072 | LJGI.070108 | 497387 | 497795 | similar to UniRef100_A7PU69 Cluster: Chromosome chr7 scaffold_31, whole genome shotgun sequence, n = 1, *Vitis vinifera*\|Rep: Chromosome chr7 scaffold_31, whole genome shotgun sequence - *Vitis vinifera* (Grape), partial (10%) |
| BQ613050 | Glycine_max_release_2 | 497409 | 498014 | ORF protein [*Arabidopsis thaliana* (Mouse-ear cress)] |
| CV541244 | Phaseolus_vulgaris | 500143 | 500464 | UniRef100_A9PGX2 Putative uncharacterized protein n = 1 Tax = *Populus trichocarpa* RepID = A9PGX2_POPTR 3.00E−28 |
| CX856527 | Glycine_max_release_2 | 501517 | 501735 | NA |
| BG839076 | Glycine_max_release_2 | 503126 | 505209 | F2P3.12 protein [*Arabidopsis thaliana* (Mouse-ear cress)] |
| FD790090 | Phaseolus_vulgaris | 503370 | 505191 | No significant hit (e−20) |
| TC236383 | GMGI.071508 | 503107 | 505675 | similar to UniRef100_O82505 Cluster: Elongation factor Ts; n = 1; *Arabidopsis thaliana*\|Rep: Elongation factor Ts - *Arabidopsis thaliana* (Mouse-ear cress) = partial (32%) |
| TA56246_3847 | Glycine_max_release_2 | 503107 | 505848 | Ethylene-responsive elongation factor EF-Ts precursor [*Lycopersicon esculentum* (Tomato)] |
| TC239475 | GMGI.071508 | 503126 | 506560 | similar to UniRef100_Q9SWW0 Cluster: Ethylene-responsive elongation factor EF-Ts precursor; n = 1; *Solanum lycopersicum*\|Rep: Ethylene-responsive elongation factor EF-Ts precursor - *Solanum lycopersicum* (Tomato) (*Lycopersicon esculentum*) = partial (74%) |
| TA56245_3847 | Glycine_max_release_2 | 505512 | 506546 | Ethylene-responsive elongation factor EF-Ts precursor [*Lycopersicon esculentum* (Tomato)] |
| BG839060 | Glycine_max_release_2 | 505661 | 506530 | At4g11120 [*Arabidopsis thaliana* (Mouse-ear cress)] |
| CV543527 | Phaseolus_vulgaris_release_2 | 508539 | 508771 | Eukaryotic translation initiation factor 5 [*Phaseolus vulgaris* (Kidney bean) (French bean)] |
| CD393454 | Glycine_max_release_2 | 510651 | 511000 | Ribosomal protein L22 [*Glycine max* (Soybean)] |
| TC245517 | GMGI.071508 | 510651 | 511270 | homologue to UniRef100_O48879 Cluster: Ribosomal protein L22; n = 1; *Glycine max*\|Rep: Ribosomal protein L22 - *Glycine max* (Soybean) = partial (80%) |
| asmbl_11866 | Vigna_unguiculata | 510868 | 511269 | NA |
| TA51206_3847 | Glycine_max_release_2 | 510702 | 512712 | Ribosomal protein L22 [*Glycine max* (Soybean)] |
| TC249077 | GMGI.071508 | 510771 | 512771 | homologue to UniRef100_O48879 Cluster: Ribosomal protein L22; n = 1; *Glycine max*\|Rep: Ribosomal |

Table 2 of the Specification

| Locus/ Display Name (1) | Source (2) | Start Base (3) | End Base (4) | ADDITIONAL LOCUS INFORMATION (5) |
|---|---|---|---|---|
| BG316244 | Glycine_max_release_2 | 511015 | 512722 | protein L22 - *Glycine max* (Soybean) = partial (98%) Ribosomal protein L22 [*Glycine max* (Soybean)] |
| BQ155270 | MTGI.071708 | 513084 | 514936 | similar to UniRef100_A7PR59 Cluster: Chromosome chr14 scaffold_26, whole genome shotgun sequence, n = 1, *Vitis vinifera*|Rep: Chromosome chr14 scaffold_26, whole genome shotgun sequence - *Vitis vinifera* (Grape), partial (52%) |
| TC30151 | LJGI.070108 | 514647 | 516395 | similar to UniRef100_A7PR59 Cluster: Chromosome chr14 scaffold_26, whole genome shotgun sequence, n = 1, *Vitis vinifera*|Rep: Chromosome chr14 scaffold_26, whole genome shotgun sequence - *Vitis vinifera* (Grape), partial (29%) |
| BP044357 | Lotus_japonicus_release_1 | 514647 | 516409 | S-locus protein 8 [*Brassica campestris* (Field mustard)] |
| CB540591 | Phaseolus_vulgaris | 514839 | 516355 | No significant hit (e−20) |
| TA65114_3847 | Glycine_max_release_2 | 523413 | 524053 | At1g22990/F19G10_22 [*Arabidopsis thaliana* (Mouse-ear cress)] |
| TC259745 | GMGI.071508 | 523413 | 524067 | similar to UniRef100_A7P3I8 Cluster: Chromosome chr1 scaffold_5 = whole genome shotgun sequence; n = 2; *Vitis vinifera*|Rep: Chromosome chr1 scaffold_5 = whole genome shotgun sequence - *Vitis vinifera* (Grape) = partial (56%) |
| TA4332_47247 | Lotus_corniculatus_release_1 | 529321 | 530051 | Actin-11 related cluster |
| TA6031_34305 | Lotus_japonicus_release_1 | 529321 | 530051 | Actin [*Striga asiatica*] |
| TC32457 | LJGI.070108 | 529321 | 530051 | homologue to UniRef100_P30167 Cluster: Actin-58, n = 1, *Solanum tuberosum*|Rep: Actin-58 - *Solanum tuberosum* (Potato), partial (39%) |
| AW351005 | Glycine_max_release_2 | 529380 | 530095 | Actin [*Striga asiatica*] |
| TA43521_3847 | Glycine_max_release_2 | 529306 | 530175 | Actin-11 [*Arabidopsis thaliana* (Mouse-ear cress)] |
| asmbl_11867 | Vigna_unguiculata | 529342 | 530189 | NA |
| AU240079 | LJGI.070108 | 529747 | 530013 | homologue to UniRef100_P93372 Cluster: Actin-66, n = 1, *Nicotiana tabacum*|Rep: Actin-66-*Nicotiana tabacum* (Common tobacco), partial (25%) |
| AU240079 | Lotus_japonicus_release_1 | 529747 | 530039 | Actin-11 [*Arabidopsis thaliana* (Mouse-ear cress)] |
| EE127018 | Arachis_hypogaea_release_5 | 529933 | 530285 | Cluster: Hypothetical protein, n = 1, *Oryza sativa* (indica cultivar-group)|Rep: Hypothetical protein - *Oryza sativa* subsp. *indica* (Rice) |
| TC240040 | GMGI.071508 | 529306 | 531078 | homologue to UniRef100_P02581 Cluster: Actin-1; n = 1; *Glycine max*|Rep: Actin-1 - *Glycine max* (Soybean) = complete |
| AW666288 | Glycine_max_release_2 | 529980 | 530789 | Actin [*Phaseolus acutifolius* (Tepary bean)] |
| TA43509_3847 | Glycine_max_release_2 | 529888 | 530911 | Actin [*Glycine max* (Soybean)] |
| TA6074_34305 | Lotus_japonicus_release_1 | 530031 | 531095 | Actin-1 [*Sorghum bicolor* (Sorghum) (*Sorghum vulgare*)] |

Table 2 of the Specification

| Locus/ Display Name (1) | Source (2) | Start Base (3) | End Base (4) | ADDITTIONAL LOCUS INFORMATION (5) |
|---|---|---|---|---|
| TC26188 | LJGI.070108 | 530031 | 531095 | homologue to UniRef100_A1Y2A0 Cluster: Actin, n = 1, *Aegiceras corniculatum*|Rep: Actin - *Aegiceras corniculatum*, partial (81%) |
| BM142797 | Glycine_max_release_2 | 530212 | 531095 | Actin [*Trifolium pratense* (Red clover)] |
| BP036880 | Lotus_japonicus_release_1 | 530235 | 531095 | Actin/actin-like [*Medicago truncatula* (Barrel medic)] |
| AW349632 | Glycine_max_release_2 | 533113 | 533701 | NA |
| AI900119 | Glycine_max_release_2 | 533044 | 534995 | NA |
| TA51800_3847 | Glycine_max_release_2 | 533054 | 535063 | NA |
| TC241826 | GMGI.071508 | 533055 | 535063 | similar to UniRef100_Q2Z1Y5 Cluster: Pm52 protein; n = 1; *Prunus mume*|Rep: Pm52 protein - *Prunus mume* (Japanese flowering apricot) = partial (73%) |
| BU494245 | LJGI.070108 | 533191 | 534994 | weakly similar to UniRef100_Q2Z1Y5 Cluster: Pm52 protein, n = 1, *Prunus mume*|Rep: Pm52 protein - *Prunus mume* (Japanese flowering apricot), partial (59%) |
| AI440735 | Glycine_max_release_2 | 534517 | 535020 | NA |
| AI440735 | GMGI.071508 | 534522 | 535020 | similar to UniRef100_Q2Z1Y5 Cluster: Pm52 protein; n = 1; *Prunus mume*|Rep: Pm52 protein - *Prunus mume* (Japanese flowering apricot) = partial (41%) |
| TC250013 | GMGI.071508 | 536842 | 537680 | UniRef100_Q8L7J4 Cluster: Pyruvate kinase; n = 1; *Glycine max*|Rep: Pyruvate kinase - *Glycine max* (Soybean) = partial (29%) |
| TA10574_343051 | Lotus_japonicus_release_1 | 537149 | 537628 | Pyruvate kinase [*Glycine max* (Soybean)] |
| TC26632 | LJGI.070108 | 537149 | 537628 | homologue to UniRef100_Q42806 Cluster: Pyruvate kinase, cytosolic isozyme, n = 1, *Glycine max*|Rep: Pyruvate kinase, cytosolic isozyme - *Glycine max* (Soybean), partial (26%) |
| CV536725 | Phaseolus_vulgaris_release_2 | 537147 | 537846 | Pyruvate kinase = cytosolic isozyme [*Glycine max* (Soybean)] |
| asmbl_11868 | Vigna_unguiculata | 537127 | 538325 | NA |
| TC25282 | LJGI.070108 | 537149 | 538489 | homologue to UniRef100_Q8L7J4 Cluster: Pyruvate kinase, n = 1, *Glycine max*|Rep: Pyruvate kinase - *Glycine max* (Soybean), partial (29%) |
| TA47094_3847 | Glycine_max_release_2 | 536842 | 539314 | Pyruvate kinase [*Glycine max* (Soybean)] |
| Pvcon4373 | Phaseolus_vulgaris | 537147 | 539113 | UniRef100_Q42806 Pyruvate kinase, cytosolic isozyme n = 1 Tax = *Glycine max* RepID = KPYC_SOYBN E-0 |
| TC124922 | MTGI.071708 | 537491 | 538783 | homologue to UniRef100_Q42806 Cluster: Pyruvate kinase, cytosolic isozyme, n = 1, *Glycine max*|Rep: Pyruvate kinase, cytosolic isozyme - *Glycine max* (Soybean), partial (64%) |
| BF598352 | Glycine_soja_release_2 | 538308 | 538971 | Pyruvate kinase [*Citrus sinensis* (Sweet orange)] |

-continued

Table 2 of the Specification

| Locus/ Display Name (1) | Source (2) | Start Base (3) | End Base (4) | ADDITTIONAL LOCUS INFORMATION (5) |
|---|---|---|---|---|
| BG044770 | Glycine_soja_release_2 | 538624 | 539149 | Pyruvate kinase [*Citrus sinensis* (Sweet orange)] |
| TC249941 | GMGI.071508 | 538549 | 539314 | UniRef100_Q8L7J4 Cluster: Pyruvate kinase; n = 1; *Glycine max*|Rep: Pyruvate kinase - *Glycine max* (Soybean) = partial (37%) |
| BE608312 | Glycine_max_release_2 | 542536 | 544875 | Hypothetical protein [*Arabidopsis thaliana* (Mouse-ear cress)] |
| TC253996 | GMGI.071508 | 542045 | 546856 | similar to UniRef100_A7QNQ5 Cluster: Chromosome undetermined scaffold_133 = whole genome shotgun sequence; n = 1; *Vitis vinifera*|Rep: Chromosome undetermined scaffold_133 = whole genome shotgun sequence - *Vitis vinifera* (Grape) = partial (80%) |
| TC258772 | GMGI.071508 | 548268 | 548805 | NA |
| CV533614 | Phaseolus_vulgaris | 548540 | 548638 | No significant hit |
| TA57756_3847 | Glycine_max_release_2 | 548268 | 551375 | Putative microtubule-severing protein subunit [*Oryza sativa* (*japonica* cultivar-group)] |
| TC239891 | GMGI.071508 | 548323 | 551375 | similar to UniRef100_A7QNQ6 Cluster: Chromosome undetermined scaffold_133 = whole genome shotgun sequence; n = 1; *Vitis vinifera*|Rep: Chromosome undetermined scaffold_133 = whole genome shotgun sequence - *Vitis vinifera* (Grape) = partial (12%) |
| EH221990 | GMGI.071508 | 550796 | 551633 | weakly similar to UniRef100_A7QNQ6 Cluster: Chromosome undetermined scaffold_133 = whole genome shotgun sequence; n = 1; *Vitis vinifera*|Rep: Chromosome undetermined scaffold_133 = whole genome shotgun sequence - *Vitis vinifera* (Grape) = partial (7%) |
| EV263369 | GMGI.071508 | 552842 | 553615 | similar to UniRef100_A8D2Q2 Cluster: ATP synthase protein 8; n = 1; *Caranx ignobilis*|Rep: ATP synthase protein 8 - *Caranx ignobilis* = partial (37%) |
| BU964969 | Glycine_max_release_2 | 556336 | 556943 | NA |
| BU964969 | GMGI.071508 | 556494 | 556943 | similar to UniRef100_Q9MYM4 Cluster: Lysosomal alpha-glucosidase precursor; n = 1; *Bos taurus*|Rep: Lysosomal alpha-glucosidase = partial (1%) |
| EH221989 | GMGI.071508 | 562783 | 563692 | homologue to UniRef100_A7QNQ6 Cluster: Chromosome undetermined scaffold_133 = whole genome shotgun sequence; n = 1; *Vitis vinifera*|Rep: Chromosome undetermined scaffold_133 = whole genome shotgun sequence - *Vitis vinifera* (Grape) = partial (3%) |
| AW831441 | GMGI.071508 | 573069 | 573567 | NA |
| AW831441 | Glycine_max_release_2 | 573069 | 573639 | NA |
| TA6761_34305 | Lotus_japonicus_release_1 | 573706 | 580487 | Sphingosine kinase [*Lotus japonicus*] |

-continued

Table 2 of the Specification

| Locus/ Display Name (1) | Source (2) | Start Base (3) | End Base (4) | ADDITIONAL LOCUS INFORMATION (5) |
|---|---|---|---|---|
| TC20288 | LJGI.070108 | 573706 | 580487 | UniRef100_Q5KR50 Cluster: Sphingosine kinase, n = 1, *Lotus japonicus*\|Rep: Sphingosine kinase - *Lotus japonicus*, complete |
| TC122322 | MTGI.071708 | 574490 | 580620 | homologue to UniRef100_Q5KR50 Cluster: Sphingosine kinase, n = 1, *Lotus japonicus*\|Rep: Sphingosine kinase - *Lotus japonicus*, partial (66%) |
| BI701010 | Glycine_max_release_2 | 577145 | 579375 | Sphingosine kinase [*Lotus japonicus*] |
| Pvcon3123 | Phaseolus_vulgaris | 577107 | 580468 | UniRef100_Q5KR50 Sphingosine kinase n = 1 Tax = *Lotus japonicus* RepID = Q5KR50_LOTJA E-0 |
| TA49258_3847 | Glycine_max_release_2 | 579511 | 580791 | Sphingosine kinase [*Lotus japonicus*] |
| TC235674 | GMGI.071508 | 579511 | 580791 | homologue to UniRef100_Q5KR50 Cluster: Sphingosine kinase; n = 1; *Lotus japonicus*\|Rep: Sphingosine kinase - *Lotus japonicus* = partial (26%) |
| BI969866 | Glycine_max_release_2 | 579600 | 580756 | Sphingosine kinase [*Lotus japonicus*] |
| EH043869 | Arachis_stenosperma_release_5 | 579729 | 580660 | Cluster: Sphingosine kinase, n = 1, *Lotus japonicus*\|Rep: Sphingosine kinase - *Lotus japonicus* |
| BQ786742 | Glycine_max_release_2 | 580594 | 580719 | NA |
| BM108235 | Glycine_max_release_2 | 581688 | 582006 | NA |
| AW508189 | Glycine_max_release_2 | 581725 | 582244 | Hypothetical protein [*Arabidopsis thaliana* (Mouse-ear cress)] |
| TC238711 | GMGI.071508 | 581688 | 582562 | similar to UniRef100_A7QNQ7 Cluster: Chromosome undetermined scaffold_133 = whole genome shotgun sequence; n = 1; *Vitis vinifera*\|Rep: Chromosome undetermined scaffold_133 = whole genome shotgun sequence - *Vitis vinifera* (Grape) = partial (50%) |
| TA46155_3847 | Glycine_max_release_2 | 581745 | 582556 | Hypothetical protein [*Arabidopsis thaliana* (Mouse-ear cress)] |
| AW278369 | GMGI.071508 | 581988 | 582389 | similar to UniRef100_A7QNQ7 Cluster: Chromosome undetermined scaffold_133 = whole genome shotgun sequence; n = 1; *Vitis vinifera*\|Rep: Chromosome undetermined scaffold_133 = whole genome shotgun sequence - *Vitis vinifera* (Grape) = partial (44%) |
| AW278369 | Glycine_max_release_2 | 581988 | 582418 | Hypothetical protein [*Arabidopsis thaliana* (Mouse-ear cress)] |
| CD394810 | Glycine_max_release_2 | 582134 | 582328 | NA |
| BG047332 | Glycine_max_release_2 | 591288 | 592013 | OSJNBb0065L13.3 protein [*Oryza sativa (japonica cultivar-group)*] |
| TC272805 | GMGI.071508 | 591358 | 592013 | similar to UniRef100_A7NXM8 Cluster: Chromosome chr5 scaffold_2 = whole genome shotgun sequence; n = 1; *Vitis* |

Table 2 of the Specification

| Locus/ Display Name (1) | Source (2) | Start Base (3) | End Base (4) | ADDITIONAL LOCUS INFORMATION (5) |
|---|---|---|---|---|
| BW599171 | LJGI.070108 | 593399 | 593875 | vinifera\|Rep: Chromosome chr5 scaffold_2 = whole genome shotgun sequence - *Vitis vinifera* (Grape) = partial (15%) weakly similar to UniRef100_A7PT63 Cluster: Chromosome chr8 scaffold_29, whole genome shotgun sequence, n = 1, *Vitis vinifera*\|Rep: Chromosome chr8 scaffold_29, whole genome shotgun sequence - *Vitis vinifera* (Grape), partial (24%) |
| BE057829 | Glycine_max_release_2 | 606858 | 607008 | NA |
| TC275159 | GMGI.071508 | 606858 | 607456 | NA |
| BE612118 | GMGI.071508 | 615853 | 616253 | weakly similar to UniRef100_A7GPV4 Cluster: Citrate transporter; n = 1; *Bacillus cereus* subsp. *cytotoxis* NVH 391-98\|Rep: Citrate transporter - *Bacillus cereus* subsp. *cytotoxis* (strain NVH 391-98) = partial (5%) |
| BE612118 | Glycine_max_release_2 | 615869 | 616269 | NA |
| CA910895 | Phaseolus_coccineus_release_2 | 622174 | 622531 | *Arabidopsis thaliana* genomic DNA, chromosome 5, P1 clone: MPO12 [*Arabidopsis thaliana* (Mouse-ear cress)] |
| BU763992 | Glycine_max_release_2 | 625192 | 625591 | NA |
| TA51978_3847 | Glycine_max_release_2 | 625330 | 626304 | Putative ethylene-responsive protein [*Oryza sativa* (*japonica* cultivar-group)] |
| TC236117 | GMGI.071508 | 625330 | 626304 | similar to UniRef100_A7PM86 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (43%) |
| TC263881 | GMGI.071508 | 625192 | 627651 | similar to UniRef100_A7PM86 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (76%) |
| TA51979_3847 | Glycine_max_release_2 | 625252 | 627642 | Putative ethylene response protein [*Capsicum chinense* (Scotch bonnet) (Bonnet pepper)] |
| TC236300 | GMGI.071508 | 625318 | 627642 | similar to UniRef100_A7PM86 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (98%) |
| CA910548 | Phaseolus_coccineus_release_2 | 625559 | 627607 | Putative ethylene response protein [*Capsicum chinense* (Scotch bonnet) (Bonnet pepper)] |
| Pvcon5808 | Phaseolus_vulgaris | 625567 | 627610 | UniRef100_A7PM86 Chromosome chr14 scaffold_21, whole genome shotgun sequence n = 1 |

Table 2 of the Specification

| Locus/ Display Name (1) | Source (2) | Start Base (3) | End Base (4) | ADDITIONAL LOCUS INFORMATION (5) |
|---|---|---|---|---|
| EV269595 | GMGI.071508 | 627204 | 627569 | Tax = *Vitis vinifera* RepID = A7PM86_VITVI 2.00E−77 similar to UniRef100_A7PM86 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (29%) |
| BI273677 | Glycine_max_release_2 | 637550 | 637816 | NA |
| BP049107 | Lotus_corniculatus_release_1 | 647584 | 649419 | Cinnamoyl CoA reductase-like protein related cluster |
| TC258382 | GMGI.071508 | 646415 | 652371 | weakly similar to UniRef100_A7PM88 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (72%) |
| TA50222_3847 | Glycine_max_release_2 | 646722 | 652222 | Cinnamoyl CoA reductase-like protein [*Arabidopsis thaliana* (Mouse-ear cress)] |
| SATT495 |  | 650288 | 650531 |  |
| Satt495 | ePCR | 650288 | 650531 | Map3.0 SSR L/Gm19 cM: 2.7 |
| AW099618 | GMGI.071508 | 649276 | 652222 | weakly similar to UniRef100_A7PM88 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (23%) |
| TA50296_3847 | Glycine_max_release_2 | 674409 | 676421 | NA |
| BQ629031 | Glycine_max_release_2 | 674669 | 676494 | NA |
| BM520842 | Glycine_soja_release_2 | 674685 | 676538 | NA |
| TC264557 | GMGI.071508 | 674741 | 676494 | NA |
| BU765059 | Glycine_max_release_2 | 674828 | 676698 | NA |
| BU765059 | GMGI.071508 | 674925 | 676698 | weakly similar to UniRef100_A7L4B0 Cluster: Protein kinase; n = 1; *Carica papaya*\|Rep: Protein kinase - *Carica papaya* (Papaya) = partial (6%) |
| TC264815 | GMGI.071508 | 674409 | 678111 | weakly similar to UniRef100_A7L4B0 Cluster: Protein kinase; n = 1; *Carica papaya*\|Rep: Protein kinase - *Carica papaya* (Papaya) = partial (14%) |
| asmbl_11869 | Vigna_unguiculata | 676473 | 676672 | NA |
| TA50295_3847 | Glycine_max_release_2 | 674775 | 678957 | NA |
| Pvcon1987 | Phaseolus_vulgaris | 674506 | 679702 | UniRef100_A7L4B0 Protein kinase n = 1 Tax = *Carica papaya* RepID = A7L4B0_CARPA 1.00E−127 |
| BM528477 | Glycine_max_release_2 | 676507 | 678111 | NA |
| TA11531_47247 | Lotus_corniculatus_release_1 | 676692 | 678714 | Protein kinase-like protein related cluster |
| TA13031_343051 | Lotus_japonicus_release_1 | 676692 | 678714 | Hypothetical protein At5g14720 [*Arabidopsis thaliana* (Mouse-ear cress)] |
| TC31122 | LJGI.070108 | 676701 | 678714 | similar to UniRef100_A7L4B0 Cluster: Protein kinase, n = 1, |

-continued

| Locus/ Display Name (1) | Source (2) | Start Base (3) | End Base (4) | ADDITIONAL LOCUS INFORMATION (5) |
|---|---|---|---|---|
| TC255388 | GMGI.071508 | 679127 | 681361 | *Carica papaya*\|Rep: Protein kinase - *Carica papaya* (*Papaya*), partial (14%) homologue to UniRef100_A7PM90 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (44%) |
| TC124284 | MTGI.071708 | 679117 | 681419 | homologue to UniRef100_A7PM90 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (48%) |
| DV565290 | Phaseolus_vulgaris | 681368 | 681460 | No significant hit (e−20) |
| toGm05 | DAGchainer | 603011 | 803108 | Ks0.2166 |
| NP7265365 | MTGI.071708 | 703588 | 713159 | GB\|AC124951.19\|ABE84834.1 ATPase, E1-E2 type, Peptidase M, neutral zinc metallopeptidases, zinc-binding site |
| BF325038 | Glycine_max_release_2 | 711165 | 712911 | ATPase = E1-E2 type; Peptidase M = neutral zinc metallopeptidases = zinc-binding site [*Medicago truncatula* (Barrel medic)] |
| FE897117 | Phaseolus_vulgaris | 715539 | 715874 | UniRef100_Q93VL6 NBS-LRR resistance-like protein J78 n = 1 Tax = *Phaseolus vulgaris* RepID = Q93VL6_PHAVU 2.00E−47 |
| TC264844 | GMGI.071508 | 731939 | 732440 | weakly similar to UniRef100_A7PD05 Cluster: Chromosome chr17 scaffold_12 = whole genome shotgun sequence; n = 1; *Vitis vinifera*\|Rep: Chromosome chr17 scaffold_12 = whole genome shotgun sequence - *Vitis vinifera* (Grape) = partial (13%) |
| TA67235_3847 | Glycine_max_release_2 | 731939 | 733078 | NA |
| CD404253 | GMGI.071508 | 732439 | 733078 | homologue to UniRef100_A7PM92 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (8%) |
| BU091162 | GMGI.071508 | 737876 | 738292 | NA |
| BU091162 | Glycine_max_release_2 | 737876 | 738363 | NA |
| asmbl_11870 | Vigna_unguiculata | 740144 | 741401 | NA |
| BI470779 | GMGI.071508 | 740189 | 741746 | similar to UniRef100_Q9XQB0 Cluster: Carbonic anhydrase; n = 1; *Vigna radiata* var. *radiata*\|Rep: Carbonic anhydrase - *Phaseolus aureus* (Mung bean) (*Vigna radiata*) = partial (30%) |

Table 2 of the Specification

| Locus/<br>Display Name<br>(1) | Source (2) | Start<br>Base (3) | End<br>Base (4) | ADDITIONAL LOCUS<br>INFORMATION (5) |
|---|---|---|---|---|
| TA43150_3847 | Glycine_max_release_2 | 740126 | 742524 | Carbonic anhydrase [*Phaseolus aureus* (Mung bean) (*Vigna radiata*)] |
| BG509786 | GMGI.071508 | 740265 | 742434 | homologue to UniRef100_Q9XQB0 Cluster: Carbonic anhydrase; n = 1; *Vigna radiata* var. *radiata*|Rep: Carbonic anhydrase - *Phaseolus aureus* (Mung bean) (*Vigna radiata*) = partial (34%) |
| BG509786 | Glycine_max_release_2 | 740265 | 742656 | Carbonic anhydrase [*Zea mays* (Maize)] |
| DT083317 | Glycine_soja_release_2 | 740299 | 742670 | Carbonic anhydrase [*Zea mays* (Maize)] |
| AW781596 | Glycine_max_release_2 | 740182 | 742860 | Carbonic anhydrase [*Phaseolus aureus* (Mung bean) (*Vigna radiata*)] |
| BU089680 | Glycine_max_release_2 | 741070 | 742671 | Carbonic anhydrase [*Zea mays* (Maize)] |
| BM887226 | Glycine_max_release_2 | 741037 | 742852 | Carbonic anhydrase [*Zea mays* (Maize)] |
| BU089600 | Glycine_max_release_2 | 741070 | 742891 | Carbonic anhydrase [*Zea mays* (Maize)] |
| TC23104 | LJGI.070108 | 740127 | 744319 | similar to UniRef100_Q9XQB0 Cluster: Carbonic anhydrase, n = 1, *Vigna radiata* var. *radiata*|Rep: Carbonic anhydrase - *Phaseolus aureus* (Mung bean) (*Vigna radiata*), partial (98%) |
| TA2934_3885 | Phaseolus_vulgaris_release_2 | 739932 | 744687 | Carbonic anhydrase [*Zea mays* (Maize)] |
| TC238511 | GMGI.071508 | 740118 | 744639 | homologue to UniRef100_Q9XQB0 Cluster: Carbonic anhydrase; n = 1; *Vigna radiata* var. *radiata*|Rep: Carbonic anhydrase - *Phaseolus aureus* (Mung bean) (*Vigna radiata*) = complete |
| TA377_34305 | Lotus_japonicus_release_1 | 740127 | 744704 | Carbonic anhydrase [*Zea mays* (Maize)] |
| Pvcon229 | Phaseolus_vulgaris | 740125 | 744728 | UniRef100_Q9XQB0 Carbonic anhydrase n = 1 Tax = *Vigna radiata* var. *radiata* RepID = Q9XQB0_PHAAU 1.00E-176 |
| TA2935_3885 | Phaseolus_vulgaris_release_2 | 740178 | 744687 | Carbonic anhydrase [*Zea mays* (Maize)] |
| TA2376_3848 | Glycine_soja_release_2 | 740118 | 744805 | Carbonic anhydrase [*Phaseolus aureus* (Mung bean) (*Vigna radiata*)] |
| TA43157_3847 | Glycine_max_release_2 | 740117 | 744844 | Carbonic anhydrase [*Zea mays* (Maize)] |
| TA43160_3847 | Glycine_max_release_2 | 741051 | 744186 | Carbonic anhydrase = chloroplast precursor (EC 4.2.1.1) (Carbonate dehydratase) [Contains: Carbonic anhydrase = 27 kDa isoform; Carbonic anhydrase = 25 kDa isoform] [*Pisum sativum* (Garden pea)] |
| TC135779 | MTGI.071708 | 741364 | 744530 | homologue to UniRef100_P17067 Cluster: Carbonic anhydrase, chloroplast precursor (Carbonate dehydratase) [Contains: Carbonic anhydrase, 27 kDa isoform, Carbonic anhydrase, 25 kDa isoform], n = 1, *Pisum sativum*|Rep: Carbonic |

Table 2 of the Specification

| Locus/ Display Name (1) | Source (2) | Start Base (3) | End Base (4) | ADDITTIONAL LOCUS INFORMATION (5) |
|---|---|---|---|---|
| | | | | anhydrase, chloroplast precursor (Carbonate dehydratase) [Contains: Carbonic anhydrase, 27 kDa isoform, Carbonic anhydrase, 25 kDa isoform]- *Pisum sativum* (Garden pea), partial (79%) |
| TA4174_3848 | Glycine_soja_release_2 | 742624 | 743398 | Carbonic anhydrase [*Phaseolus aureus* (Mung bean) (*Vigna radiata*)] |
| Pvcon228 | Phaseolus_vulgaris | 741374 | 744687 | UniRef100_Q9XQB0 Carbonic anhydrase n = 1 Tax = *Vigna radiata* var. *radiata* RepID = Q9XQB0_PHAAU 1.00E−137 |
| TA43163_3847 | Glycine_max_release_2 | 741381 | 744770 | Carbonic anhydrase [*Zea mays* (Maize)] |
| TC247359 | GMGI.071508 | 741381 | 744770 | homologue to UniRef100_Q9XQB0 Cluster: Carbonic anhydrase; n = 1; *Vigna radiata* var. *radiata*\|Rep: Carbonic anhydrase - *Phaseolus aureus* (Mung bean) (*Vigna radiata*) = partial (62%) |
| BG045644 | Glycine_soja_release_2 | 742643 | 743622 | Carbonic anhydrase = chloroplast precursor (EC 4.2.1.1) (Carbonate dehydratase) [Contains: Carbonic anhydrase = 27 kDa isoform; Carbonic anhydrase = 25 kDa isoform] [*Pisum sativum* (Garden pea)] |
| Pvcon227 | Phaseolus_vulgaris | 741681 | 744687 | UniRef100_Q9XQB0 Carbonic anhydrase n = 1 Tax = *Vigna radiata* var. *radiata* RepID = Q9XQB0_PHAAU 1.00E−133 |
| TC124201 | MTGI.071708 | 741922 | 744665 | homologue to UniRef100_P17067 Cluster: Carbonic anhydrase, chloroplast precursor (Carbonate dehydratase) [Contains: Carbonic anhydrase, 27 kDa isoform, Carbonic anhydrase, 25 kDa isoform], n = 1, *Pisum sativum*\|Rep: Carbonic anhydrase, chloroplast precursor (Carbonate dehydratase) [Contains: Carbonic anhydrase, 27 kDa isoform, Carbonic anhydrase, 25 kDa isoform]- *Pisum sativum* (Garden pea), partial (57%) |
| CB543710 | Phaseolus_vulgaris_release_2 | 742464 | 744532 | Carbonic anhydrase [*Phaseolus aureus* (Mung bean) (*Vigna radiata*)] |
| CB539509 | Phaseolus_vulgaris_release_2 | 742480 | 744557 | Carbonic anhydrase [*Zea mays* (Maize)] |
| TC126947 | MTGI.071708 | 742434 | 744665 | homologue to UniRef100_P17067 Cluster: Carbonic anhydrase, chloroplast precursor (Carbonate dehydratase) [Contains: Carbonic anhydrase, 27 kDa isoform, Carbonic anhydrase, 25 kDa isoform], n = 1, *Pisum sativum*\|Rep: Carbonic |

Table 2 of the Specification

| Locus/ Display Name (1) | Source (2) | Start Base (3) | End Base (4) | ADDITIONAL LOCUS INFORMATION (5) |
|---|---|---|---|---|
| | | | | anhydrase, chloroplast precursor (Carbonate dehydratase) [Contains: Carbonic anhydrase, 27 kDa isoform, Carbonic anhydrase, 25 kDa isoform]- *Pisum sativum* (Garden pea), partial (51%) |
| asmbl_11871 | Vigna_unguiculata | 742823 | 744369 | NA |
| asmbl_11872 | Vigna_unguiculata | 742628 | 744687 | NA |
| asmbl_11874 | Vigna_unguiculata | 742641 | 744687 | NA |
| TA43165_3847 | Glycine_max_release_2 | 742658 | 744772 | Carbonic anhydrase [*Phaseolus aureus* (Mung bean) (*Vigna radiata*)] |
| TC241035 | GMGI.071508 | 742658 | 744772 | homologue to UniRef100_Q9XQB0 Cluster: Carbonic anhydrase; n = 1; *Vigna radiata* var. *radiata*\|Rep: Carbonic anhydrase - *Phaseolus aureus* (Mung bean) (*Vigna radiata*) = partial (38%) |
| TA480_3888 | Pisum_sativum_release_2 | 742823 | 744641 | Carbonic anhydrase, chloroplast precursor (EC 4.2.1.1) (Carbonate dehydratase) [Contains: Carbonic anhydrase, 27 kDa isoform, Carbonic anhydrase, 25 kDa isoform] [*Pisum sativum* (Garden pea)] |
| TC240357 | GMGI.071508 | 742650 | 744828 | homologue to UniRef100_Q9XQB0 Cluster: Carbonic anhydrase; n = 1; *Vigna radiata* var. *radiata*\|Rep: Carbonic anhydrase - *Phaseolus aureus* (Mung bean) (*Vigna radiata*) = partial (38%) |
| BE346766 | Glycine_max_release_2 | 743636 | 744227 | Carbonic anhydrase = chloroplast precursor (EC 4.2.1.1) (Carbonate dehydratase) [Contains: Carbonic anhydrase = 27 kDa isoform; Carbonic anhydrase = 25 kDa isoform] [*Pisum sativum* (Garden pea)] |
| AW596246 | Glycine_max_release_2 | 743636 | 744243 | Carbonic anhydrase [*Phaseolus aureus* (Mung bean) (*Vigna radiata*)] |
| BE807206 | Glycine_max_release_2 | 743636 | 744244 | Carbonic anhydrase [*Phaseolus aureus* (Mung bean) (*Vigna radiata*)] |
| CB280659 | Phaseolus_vulgaris_release_2 | 743613 | 744419 | Carbonic anhydrase [*Phaseolus aureus* (Mung bean) (*Vigna radiata*)] |
| asmbl_11875 | Vigna_unguiculata | 743587 | 744642 | NA |
| DT083076 | Glycine_soja_release_2 | 743565 | 744678 | Carbonic anhydrase [*Phaseolus aureus* (Mung bean) (*Vigna radiata*)] |
| TC29040 | LJGI.070108 | 743565 | 744702 | similar to UniRef100_Q9XQB0 Cluster: Carbonic anhydrase, n = 1, *Vigna radiata* var. *radiata*\|Rep: Carbonic anhydrase - *Phaseolus aureus* (Mung bean) (*Vigna radiata*), partial (31%) |
| TA134_47247 | Lotus_corniculatus_release_1 | 743568 | 744704 | Carbonic anhydrase related cluster |
| TA378_34305 | Lotus_japonicus_release_1 | 743568 | 744704 | Carbonic anhydrase, prokaryotic and plant [*Medicago truncatula* (Barrel medic)] |
| TC24201 | LJGI.070108 | 743584 | 744704 | similar to UniRef100_Q9XQB0 Cluster: Carbonic anhydrase, n = 1, *Vigna radiata* var. *radiata*\|Rep: Carbonic |

Table 2 of the Specification

| Locus/ Display Name (1) | Source (2) | Start Base (3) | End Base (4) | ADDITIONAL LOCUS INFORMATION (5) |
|---|---|---|---|---|
| | | | | anhydrase - *Phaseolus aureus* (Mung bean) (*Vigna radiata*), partial (25%) |
| CB539196 | Phaseolus_vulgaris_release_2 | 743626 | 744687 | Carbonic anhydrase [*Phaseolus aureus* (Mung bean) (*Vigna radiata*)] |
| AV413187 | LJGI.070108 | 744089 | 744647 | similar to UniRef100_P27140 Cluster: Carbonic anhydrase, chloroplast precursor, n = 4, *Arabidopsis thaliana*|Rep: Carbonic anhydrase, chloroplast precursor - *Arabidopsis thaliana* (Mouse-ear cress), partial (17%) |
| AV413187 | Lotus_japonicus_release_1 | 744089 | 744672 | Carbonic anhydrase, chloroplast precursor [*Arabidopsis thaliana* (Mouse-ear cress)] |
| CD860850 | Pisum_sativum_release_2 | 744145 | 744641 | Carbonic anhydrase, chloroplast precursor [*Arabidopsis thaliana* (Mouse-ear cress)] |
| CD403834 | Glycine_max_release_2 | 744076 | 744732 | Carbonic anhydrase = chloroplast precursor [*Arabidopsis thaliana* (Mouse-ear cress)] |
| CD415400 | Glycine_max_release_2 | 744251 | 744691 | NA |
| asmbl_11873 | Vigna_unguiculata | 744448 | 744649 | NA |
| CB541850 | Phaseolus_vulgaris | 747218 | 747570 | No significant hit (e−20) |
| BM953717 | Glycine_max_release_2 | 747199 | 748912 | Peptidase S1 and S6 = chymotrypsin/Hap [*Medicago truncatula* (Barrel medic)] |
| EH256926 | GMGI.071508 | 747192 | 749279 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (21%) |
| TA51716_3847 | Glycine_max_release_2 | 747191 | 749327 | Putative DegP protease [*Oryza sativa* (*japonica* cultivar-group)] |
| TC243148 | GMGI.071508 | 747199 | 749327 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (25%) |
| AV768772 | LJGI.070108 | 747281 | 749288 | homologue to UniRef100_O22609 Cluster: Protease Do-like 1, chloroplast precursor, n = 1, *Arabidopsis thaliana*|Rep: Protease Do-like 1, chloroplast precursor - *Arabidopsis thaliana* (Mouse-ear cress), partial (23%) |
| BE807421 | Glycine_max_release_2 | 748776 | 749688 | Peptidase S1 and S6 = chymotrypsin/Hap [*Medicago truncatula* (Barrel medic)] |
| TA51715_3847 | Glycine_max_release_2 | 747251 | 752927 | Peptidase S1 and S6 = chymotrypsin/Hap [*Medicago truncatula* (Barrel medic)] |
| TC260884 | GMGI.071508 | 747251 | 752942 | homologue to UniRef100_A7Q7E6 Cluster: Chromosome chr18 scaffold_59 = whole genome shotgun sequence; n = 1; *Vitis vinifera*|Rep: Chromosome |

Table 2 of the Specification

| Locus/ Display Name (1) | Source (2) | Start Base (3) | End Base (4) | ADDITIONAL LOCUS INFORMATION (5) |
|---|---|---|---|---|
| | | | | chr18 scaffold_59 = whole genome shotgun sequence - *Vitis vinifera* (Grape) = partial (80%) |
| BE474482 | Glycine_max_release_2 | 751068 | 752387 | Peptidase S1 and S6 = chymotrypsin/Hap [*Medicago truncatula* (Barrel medic)] |
| BE474482 | GMGI.071508 | 751070 | 752387 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (19%) |
| TC261290 | GMGI.071508 | 755656 | 757218 | similar to UniRef100_A7PM96 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (33%) |
| BG646067 | MTGI.071708 | 756996 | 759297 | similar to UniRef100_A7PM96 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (33%) |
| BE555567 | Glycine_max_release_2 | 757210 | 762134 | Hypothetical protein [*Medicago truncatula* (Barrel medic)] |
| BE555567 | GMGI.071508 | 757746 | 762134 | similar to UniRef100_A7PM96 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (31%) |
| BE058948 | Glycine_max_release_2 | 762117 | 763784 | Hypothetical protein [*Medicago truncatula* (Barrel medic)] |
| BE058948 | GMGI.071508 | 762818 | 763784 | similar to UniRef100_A7PM96 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (25%) |
| TC138874 | MTGI.071708 | 768876 | 770881 | similar to UniRef100_Q40318 Cluster: Coil protein, n = 1, *Medicago sativa*|Rep: Coil protein - *Medicago sativa* (Alfalfa), partial (60%) |
| TC124470 | MTGI.071708 | 768770 | 771318 | similar to UniRef100_Q1RU40 Cluster: Lipolytic enzyme, G-D-S-L, n = 1, *Medicago truncatula*|Rep: Lipolytic enzyme, G-D-S-L - *Medicago truncatula* (Barrel medic), partial (77%) |
| TC268582 | GMGI.071508 | 768733 | 771727 | weakly similar to UniRef100_A7PMA0 Cluster: Chromosome chr14 scaffold_21 = whole genome |

Table 2 of the Specification

| Locus/ Display Name (1) | Source (2) | Start Base (3) | End Base (4) | ADDITIONAL LOCUS INFORMATION (5) |
|---|---|---|---|---|
| | | | | shotgun sequence; n = 1; *Vitis vinifera*|Rep: Chromosome chr14 scaffold_21 = whole genome shotgun sequence - *Vitis vinifera* (Grape) = partial (89%) |
| BE059369 | Glycine_max_release_2 | 770328 | 771326 | Lipolytic enzyme = G-D-S-L [*Medicago truncatula* (Barrel medic)] |
| BE329784 | GMGI.071508 | 770783 | 771236 | similar to UniRef100_Q1RU40 Cluster: Lipolytic enzyme = G-D-S-L; n = 1; *Medicago truncatula*|Rep: Lipolytic enzyme = G-D-S-L - *Medicago truncatula* (Barrel medic) = partial (27%) |
| BE329784 | Glycine_max_release_2 | 770783 | 771288 | Lipolytic enzyme = G-D-S-L [*Medicago truncatula* (Barrel medic)] |
| TA68573_3847 | Glycine_max_release_2 | 773983 | 774836 | Putative kinesin light chain [*Oryza sativa* (japonica cultivar-group)] |
| TC259227 | GMGI.071508 | 773983 | 774836 | similar to UniRef100_A7PD12 Cluster: Chromosome chr17 scaffold_12 = whole genome shotgun sequence; n = 1; *Vitis vinifera*|Rep: Chromosome chr17 scaffold_12 = whole genome shotgun sequence - *Vitis vinifera* (Grape) = partial (13%) |
| AI759741 | Glycine_max_release_2 | 774118 | 774822 | Putative kinesin light chain [*Oryza sativa* (japonica cultivar-group)] |
| asmbl_11876 | Vigna_unguiculata | 774030 | 774978 | NA |
| TC139308 | MTGI.071708 | 774935 | 775598 | similar to UniRef100_A7PMA1 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (34%) |
| AW186182 | Glycine_max_release_2 | 775276 | 775796 | Similarity to kinesin light chain [*Arabidopsis thaliana* (Mouse-ear cress)] |
| AW186182 | GMGI.071508 | 775464 | 775796 | similar to UniRef100_A7PD12 Cluster: Chromosome chr17 scaffold_12 = whole genome shotgun sequence; n = 1; *Vitis vinifera*|Rep: Chromosome chr17 scaffold_12 = whole genome shotgun sequence - *Vitis vinifera* (Grape) = partial (16%) |
| BF010272 | GMGI.071508 | 783671 | 784035 | UniRef100_Q00K67 Cluster: Major surface antigen; n = 1; Hepatitis B virus|Rep: Major surface antigen - Hepatitis B virus (HBV) = partial (5%) |
| TA54422_3847 | Glycine_max_release_2 | 783644 | 784982 | Alcohol dehydrogenase superfamily = zinc-containing [*Medicago truncatula* (Barrel medic)] |
| BI971258 | Glycine_max_release_2 | 783921 | 784926 | Auxin-induced protein [*Vigna radiata*] |
| CV542673 | Phaseolus_vulgaris_release_2 | 784213 | 785346 | Quinone oxidoreductase-like protein [*Helianthus annuus* (Common sunflower)] |
| TC239445 | GMGI.071508 | 783904 | 786356 | similar to UniRef100_O23939 Cluster: Ripening-induced protein; n = 1; *Fragaria* |

-continued

Table 2 of the Specification

| Locus/ Display Name (1) | Source (2) | Start Base (3) | End Base (4) | ADDITTIONAL LOCUS INFORMATION (5) |
|---|---|---|---|---|
| | | | | vesca\|Rep: Ripening-induced protein - *Fragaria vesca* (Woodland strawberry) = partial (84%) |
| TA3037_3848 | Glycine_soja_release_2 | 784204 | 786191 | Quinone oxidoreductase-like protein [*Helianthus annuus* (Common sunflower)] |
| BG045149 | Glycine_soja_release_2 | 784943 | 785469 | Quinone oxidoreductase [*Fragaria ananassa* (Strawberry)] |
| TA54423_3847 | Glycine_max_release_2 | 784420 | 786354 | Quinone oxidoreductase-like protein [*Helianthus annuus* (Common sunflower)] |
| BG046280 | Glycine_soja_release_2 | 786163 | 786344 | NA |
| CA901808 | Phaseolus_coccineus_release_2 | 800890 | 801759 | Alcohol dehydrogenase superfamily, zinc-containing [*Medicago truncatula* (Barrel medic)] |
| TA14086_34305 | Lotus_japonicus_release_1 | 800932 | 801745 | Alcohol dehydrogenase superfamily, zinc-containing [*Medicago truncatula* (Barrel medic)] (SEQ ID NO: 15) |
| TC23841 | LJGI.070108 | 800932 | 801745 | similar to UniRef100_Q43677 Cluster: Auxin-induced protein; n = 1, *Vigna radiata*\|Rep: Auxin-induced protein - *Vigna radiata*, partial (40%) |
| M0093116 | SEQ. Listing | 805373 | 805788 | SEQ ID NO: 6 |
| TC252650 | GMGI.071508 | 805357 | 806601 | similar to UniRef100_Q43677 Cluster: Auxin-induced protein; n = 1; *Vigna radiata*\|Rep: Auxin-induced protein - *Vigna radiata* = partial (54%) |
| BARC-039375-07304 | ePCR&blat | 805660 | 806532 | Map3.0 SNP L/Gm19 cM: 3.4 |
| TA65006_3847 | Glycine_max_release_2 | 805357 | 807089 | Quinone oxidoreductase-like protein [*Helianthus annuus* (Common sunflower)] |
| TA65005_3847 | Glycine_max_release_2 | 806611 | 807310 | Alcohol dehydrogenase superfamily = zinc-containing [*Medicago truncatula* (Barrel medic)] |
| TC274718 | GMGI.071508 | 806611 | 807310 | similar to UniRef100_Q43677 Cluster: Auxin-induced protein; n = 1; *Vigna radiata*\|Rep: Auxin-induced protein - *Vigna radiata* = partial (30%) |
| AW397551 | Glycine_max_release_2 | 811245 | 811796 | Auxin-induced protein [*Vigna radiata*] |
| Pvcon4580 | Phaseolus_vulgaris | 811330 | 813524 | UniRef100_Q43677 Auxin-induced protein n = 1 Tax = *Vigna radiata* RepID = Q43677_9FABA 1.00E−133 |
| asmbl_11877 | Vigna_unguiculata | 812523 | 812779 | NA |
| BE608172 | Glycine_max_release_2 | 821487 | 822389 | Protein farnesyltransferase subunit beta [*Pisum sativum* (Garden pea)] |
| BQ273477 | Glycine_max_release_2 | 821559 | 822383 | NA |
| TC246895 | GMGI.071508 | 821516 | 822443 | similar to UniRef100_Q04903 Cluster: Protein farnesyltransferase subunit beta; n = 1; *Pisum sativum*\|Rep: Protein farnesyltransferase subunit beta - *Pisum sativum* (Garden pea) = partial (15%) |
| TC241767 | GMGI.071508 | 824186 | 828116 | similar to UniRef100_Q7XHJ0 Cluster: Formate dehydrogenase; n = 1; *Quercus robur*\|Rep: Formate dehydrogenase - *Quercus robur* (English oak) = partial (97%) |

Table 2 of the Specification

| Locus/Display Name (1) | Source (2) | Start Base (3) | End Base (4) | ADDITTIONAL LOCUS INFORMATION (5) |
|---|---|---|---|---|
| TA40711_3847 | Glycine_max_release_2 | 824209 | 828372 | Formate dehydrogenase [*Quercus robur* (English oak)] |
| AI522957 | Glycine_max_release_2 | 826883 | 827087 | Formate dehydrogenase [*Quercus robur* (English oak)] |
| BG044450 | Glycine_soja_release_2 | 826544 | 827461 | Formate dehydrogenase = mitochondrial precursor [*Solanum tuberosum* (Potato)] |
| asmbl_11878 | Vigna_unguiculata | 826586 | 827463 | NA |
| CA800817 | Glycine_soja_release_2 | 826705 | 827869 | Formate dehydrogenase [*Quercus robur* (English oak)] |
| TC240429 | GMGI.071508 | 826957 | 828379 | similar to UniRef100_Q9ZRI8 Cluster: Formate dehydrogenase = mitochondrial precursor; n = 1; *Hordeum vulgare*|Rep: Formate dehydrogenase = mitochondrial precursor - *Hordeum vulgare* (Barley) = partial (40%) |
| AW350528 | Glycine_max_release_2 | 826986 | 828379 | Formate dehydrogenase 1 = mitochondrial precursor [*Oryza sativa* (Rice)] |
| BG882062 | Glycine_max_release_2 | 827372 | 828284 | Formate dehydrogenase 1 = mitochondrial precursor [*Oryza sativa* (Rice)] |
| BE347639 | Glycine_max_release_2 | 827443 | 828262 | Formate dehydrogenase 1 = mitochondrial precursor [*Oryza sativa* (Rice)] |
| CA782711 | Glycine_soja_release_2 | 827371 | 828357 | Formate dehydrogenase 1 = mitochondrial precursor [*Oryza sativa* (Rice)] |
| TA40821_3847 | Glycine_max_release_2 | 829640 | 832253 | Formate dehydrogenase [*Quercus robur* (English oak)] |
| BE330555 | Glycine_max_release_2 | 829875 | 832057 | Formate dehydrogenase = mitochondrial precursor [*Solanum tuberosum* (Potato)] |
| BU090495 | Glycine_max_release_2 | 829863 | 832082 | Formate dehydrogenase [*Quercus robur* (English oak)] |
| BG044406 | Glycine_soja_release_2 | 829915 | 832082 | Formate dehydrogenase [*Quercus robur* (English oak)] |
| AW508186 | GMGI.071508 | 830914 | 831336 | similar to UniRef100_A7PMA5 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (15%) |
| M0129925 | SEQ LISTING | 830552 | 831704 | SEQ ID NO: 7 |
| AW508186 | Glycine_max_release_2 | 830914 | 831970 | Formate dehydrogenase = mitochondrial precursor [*Solanum tuberosum* (Potato)] |
| AW508145 | Glycine_max_release_2 | 830909 | 832061 | Formate dehydrogenase [*Quercus robur* (English oak)] |
| TA40373_3847 | Glycine_max_release_2 | 830863 | 832118 | Formate dehydrogenase [*Quercus robur* (English oak)] |
| AW397259 | Glycine_max_release_2 | 831219 | 832141 | Formate dehydrogenase [*Quercus robur* (English oak)] |
| TC261330 | GMGI.071508 | 829795 | 833576 | similar to UniRef100_Q7XHJ0 Cluster: Formate dehydrogenase; n = 1; *Quercus robur*|Rep: Formate dehydrogenase - *Quercus robur* (English oak) = partial (96%) |
| TC249502 | GMGI.071508 | 830866 | 832529 | similar to UniRef100_Q7XHJ0 Cluster: Formate dehydrogenase; n = 1; *Quercus robur*|Rep: Formate dehydrogenase - *Quercus robur* (English oak) = partial (72%) |
| TA40376_3847 | Glycine_max_release_2 | 830879 | 833356 | Formate dehydrogenase [*Quercus robur* (English oak)] |

Table 2 of the Specification

| Locus/ Display Name (1) | Source (2) | Start Base (3) | End Base (4) | ADDITIONAL LOCUS INFORMATION (5) |
|---|---|---|---|---|
| asmbl_11879 | Vigna_unguiculata | 831735 | 833050 | NA |
| AW569072 | GMGI.071508 | 832471 | 832890 | similar to UniRef100_Q7XHJ0 Cluster: Formate dehydrogenase; n = 1; *Quercus robur*\|Rep: Formate dehydrogenase - *Quercus robur* (English oak) = partial (9%) |
| AW569072 | Glycine_max_release_2 | 832471 | 832929 | Formate dehydrogenase [*Quercus robur* (English oak)] |
| TA40339_3847 | Glycine_max_release_2 | 832130 | 833531 | Formate dehydrogenase 1 = mitochondrial precursor [*Oryza sativa* (Rice)] |
| TA5191_3885 | Phaseolus_vulgaris_release_2 | 832192 | 833517 | Formate dehydrogenase [*Quercus robur* (English oak)] |
| FD790937 | Phaseolus_vulgaris | 833039 | 833412 | UniRef100_A6N0B2 Mitochondrial formate dehydrogenase 1 (Fragment) n = 1 Tax = *Oryza sativa Indica* Group RepID = A6N0B2_ORYSI 3.00E−30 |
| CA913454 | Phaseolus_coccineus_release_2 | 841331 | 841722 | NA |
| TA70199_3847 | Glycine_max_release_2 | 841305 | 841824 | NA |
| asmbl_11326 | Vigna_unguiculata | 841326 | 841889 | NA |
| TA3611_3848 | Glycine_soja_release_2 | 841347 | 842640 | Hypothetical protein OJ1593_C11.11 [*Oryza sativa* (*japonica* cultivar-group)] |
| TA5381_34305 | Lotus_japonicus_release_1 | 841455 | 842700 | Calcium homeostasis regulator CHoR1 [*Solanum tuberosum* (Potato)] |
| TC20706 | LJGI.070108 | 841455 | 842700 | weakly similar to UniRef100_Q5QTN8 Cluster: Calcium homeostasis regulator CHoR1, n = 1, *Solanum tuberosum*\|Rep: Calcium homeostasis regulator CHoR1 - *Solanum tuberosum* (Potato), partial (52%) |
| Pvcon2378 | Phaseolus_vulgaris | 841347 | 843522 | UniRef100_A7PMA9 Chromosome chr14 scaffold_21, whole genome shotgun sequence n = 1 Tax = *Vitis vinifera* RepID = A7PMA9_VITVI 4.00E−94 |
| TC252755 | GMGI.071508 | 841305 | 843655 | similar to UniRef100_A7PMA9 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (74%) |
| EX305183 | Phaseolus_vulgaris | 841682 | 843613 | UniRef100_A7PMA9 Chromosome chr14 scaffold_21, whole genome shotgun sequence n = 1 Tax = *Vitis vinifera* RepID = A7PMA9_VITVI 1.00E−67 |
| BI498351 | GMGI.071508 | 844582 | 845168 | NA |
| TA66563_3847 | Glycine_max_release_2 | 844582 | 847078 | Hypothetical protein [*Ipomoea trifida* (Morning glory)] |
| TC247953 | GMGI.071508 | 844582 | 847220 | similar to UniRef100_A7Q5T8 Cluster: Chromosome chr14 scaffold_54 = whole genome shotgun sequence; n = 1; *Vitis vinifera*\|Rep: Chromosome chr14 scaffold_54 = whole genome shotgun sequence - *Vitis vinifera* (Grape) = partial (58%) |

Table 2 of the Specification

| Locus/ Display Name (1) | Source (2) | Start Base (3) | End Base (4) | ADDITIONAL LOCUS INFORMATION (5) |
|---|---|---|---|---|
| TA3593_3848 | Glycine_soja_release_2 | 844668 | 847194 | Hypothetical protein [*Ipomoea trifida* (Morning glory)] |
| TA56324_3847 | Glycine_max_release_2 | 854425 | 856413 | Similarity to intracellular protein [*Arabidopsis thaliana* (Mouse-ear cress)] |
| TC235843 | GMGI.071508 | 854425 | 856413 | similar to UniRef100_A7PMB1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (40%) |
| CD406351 | Glycine_max_release_2 | 855627 | 856402 | Similarity to intracellular protein [*Arabidopsis thaliana* (Mouse-ear cress)] |
| TC276442 | GMGI.071508 | 855627 | 856402 | similar to UniRef100_A7PMB1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (14%) |
| TC273993 | GMGI.071508 | 863632 | 864262 | homologue to UniRef100_A7PMB2 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (26%) |
| BU082700 | Glycine_max_release_2 | 863841 | 864449 | Hypothetical protein OJ1126_B10.9 [*Oryza sativa* (*japonica* cultivar-group)] (SEQ ID NO: 14) |
| AW459960 | Glycine_max_release_2 | 863632 | 865288 | Hypothetical protein F4P13.4 [*Arabidopsis thaliana* (Mouse-ear cress)] |
| AL385435 | MTGI.071708 | 863952 | 865397 | homologue to UniRef100_A7PD25 Cluster: Chromosome chr17 scaffold_12, whole genome shotgun sequence, n = 1, *Vitis vinifera*\|Rep: Chromosome chr17 scaffold_12, whole genome shotgun sequence - *Vitis vinifera* (Grape), partial (37%) |
| AI856244 | GMGI.071508 | 864500 | 864958 | UniRef100_A7PMB2 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (6%) |
| asmbl_11881 | Vigna_unguiculata | 863829 | 865710 | NA |
| TC238318 | GMGI.071508 | 863970 | 865869 | homologue to UniRef100_A7PMB2 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (34%) |

Table 2 of the Specification

| Locus/ Display Name (1) | Source (2) | Start Base (3) | End Base (4) | ADDITIONAL LOCUS INFORMATION (5) |
|---|---|---|---|---|
| TA63907_3847 | Glycine_max_release_2 | 864500 | 865869 | Hypothetical protein F4P13.4 [*Arabidopsis thaliana* (Mouse-ear cress)] |
| BW598574 | LJGI.070108 | 865265 | 865656 | similar to UniRef100_Q8LES3 Cluster: Protein kinase, n = 1, *Arabidopsis thaliana*|Rep: Protein kinase - *Arabidopsis thaliana* (Mouse-ear cress), partial (9%) |
| BW598574 | Lotus_japonicus_release_1 | 865265 | 865674 | Protein kinase [*Arabidopsis thaliana* (Mouse-ear cress)] |
| CD400016 | Glycine_max_release_2 | 870972 | 871184 | NA |
| CD399245 | Glycine_max_release_2 | 870876 | 871427 | Putative Peptidyl-prolyl cis-trans isomerase = chloroplast [*Oryza sativa (japonica cultivar-group)*] |
| TC242592 | GMGI.071508 | 870943 | 872827 | similar to UniRef100_A6MZC4 Cluster: Peptidyl-prolyl cis-trans isomerase; n = 2; *Oryza sativa*|Rep: Peptidyl-prolyl cis-trans isomerase - *Oryza sativa* subsp. *indica* (Rice) = partial (60%) |
| CB543642 | Phaseolus_vulgaris_release_2 | 871229 | 872777 | Peptidyl-prolyl cis trans isomerase = chloroplast precursor [*Spinacia oleracea* (Spinach)] |
| TA52959_3847 | Glycine_max_release_2 | 870943 | 873450 | Poly(A) polymerase [*Pisum sativum* (Garden pea)] |
| CB539263 | Phaseolus_vulgaris_release_2 | 871195 | 873325 | Poly(A) polymerase [*Pisum sativum* (Garden pea)] |
| Pvcon1578 | Phaseolus_vulgaris | 870946 | 876143 | UniRef100_O22636 Poly(A) polymerase n = 1 Tax = *Pisum sativum* RepID = O22636_PEA E-0 |
| TA10487_34305 | Lotus_japonicus_release_1 | 873266 | 875963 | Poly(A) polymerase [*Pisum sativum* (Garden pea)] |
| TA6667_47247 | Lotus_corniculatus_release_1 | 873266 | 875963 | Poly(A) polymerase related cluster |
| TC34747 | LJGI.070108 | 873266 | 875963 | similar to UniRef100_O22636 Cluster: Poly(A) polymerase, n = 1, *Pisum sativum*|Rep: Poly(A) polymerase - *Pisum sativum* (Garden pea), partial (57%) |
| BG363373 | Glycine_max_release_2 | 874357 | 874944 | Poly(A) polymerase [*Pisum sativum* (Garden pea)] |
| TC251420 | GMGI.071508 | 874369 | 876078 | similar to UniRef100_O22636 Cluster: Poly(A) polymerase; n = 1; *Pisum sativum*|Rep: Poly(A) polymerase - *Pisum sativum* (Garden pea) = partial (37%) |
| CA901088 | Phaseolus_coccineus_release_2 | 874490 | 876191 | Poly(A) polymerase [*Pisum sativum* (Garden pea)] |
| asmbl_11882 | Vigna_unguiculata | 886629 | 890018 | NA |
| TA68870_3847 | Glycine_max_release_2 | 886534 | 893419 | Senescence-associated protein-like [*Oryza sativa (japonica cultivar-group)*] |
| TC270337 | GMGI.071508 | 886672 | 893419 | weakly similar to UniRef100_A7PD28 Cluster: Chromosome chr17 scaffold_12 = whole genome shotgun sequence; n = 1; *Vitis vinifera*|Rep: Chromosome chr17 scaffold_12 = whole genome shotgun sequence - *Vitis vinifera* (Grape) = partial (86%) |
| M0205537 | SEQ. Listing | 890458 | 890051 | SEQ ID NO: 8 |

Table 2 of the Specification

| Locus/Display Name (1) | Source (2) | Start Base (3) | End Base (4) | ADDITIONAL LOCUS INFORMATION (5) |
|---|---|---|---|---|
| BM732054 | Glycine_max_release_2 | 899859 | 901015 | NA |
| BM732054 | GMGI.071508 | 900006 | 901015 | similar to UniRef100_Q04TD2 Cluster: MviN-related protein; n = 1; *Leptospira borgpetersenii* serovar Hardjo-bovis JB197|Rep: = partial (2%) |
| toGm13 | DAGchainer | 816170 | 1014875 | Ks0.1202 |
| M0202715 | SEQ. Listing | 921233 | 921630 | SEQ ID NO: 9 |
| TA46168_3847 | Glycine_max_release_2 | 921047 | 924660 | Homeodomain leucine zipper protein HDZ3 [*Phaseolus vulgaris* (Kidney bean) (French bean)] |
| TC260016 | GMGI.071508 | 921056 | 924739 | homologue to UniRef100_Q93XA3 Cluster: Homeodomain leucine zipper protein HDZ3; n = 1; *Phaseolus vulgaris*|Rep: Homeodomain leucine zipper protein HDZ3 - *Phaseolus vulgaris* (Kidney bean) (French bean) = complete |
| Pvcon1101 | Phaseolus_vulgaris | 921086 | 924758 | UniRef100_Q93XA3 Homeodomain leucine zipper protein HDZ3 (Fragment) n = 1 Tax = *Phaseolus vulgaris* RepID = Q93XA3_PHAVU 1.00E−124 |
| TA3604_3885 | Phaseolus_vulgaris_release_2 | 921111 | 924754 | Homeodomain leucine zipper protein HDZ3 [*Phaseolus vulgaris* (Kidney bean) (French bean)] |
| asmbl_11883 | Vigna_unguiculata | 921538 | 924758 | NA |
| BG041631 | Glycine_soja_release_2 | 923015 | 923340 | Homeobox-leucine zipper protein HAT5 [*Arabidopsis thaliana* (Mouse-ear cress)] |
| AV421688 | LJGI.070108 | 923118 | 924180 | similar to UniRef100_Q93XA3 Cluster: Homeodomain leucine zipper protein HDZ3, n = 1, *Phaseolus vulgaris*|Rep: Homeodomain leucine zipper protein HDZ3 - *Phaseolus vulgaris* (Kidney bean) (French bean), partial (25%) |
| TC235979 | GMGI.071508 | 923000 | 924768 | similar to UniRef100_Q93XA3 Cluster: Homeodomain leucine zipper protein HDZ3; n = 1; *Phaseolus vulgaris*|Rep: Homeodomain leucine zipper protein HDZ3 - *Phaseolus vulgaris* (Kidney bean) (French bean) = partial (86%) |
| TA46165_3847 | Glycine_max_release_2 | 923000 | 924779 | Homeodomain leucine zipper protein HDZ3 [*Phaseolus vulgaris* (Kidney bean) (French bean)] |
| AW351287 | Glycine_max_release_2 | 923128 | 924720 | Homeodomain leucine zipper protein HDZ3 [*Phaseolus vulgaris* (Kidney bean) (French bean)] |
| CA785782 | Glycine_soja_release_2 | 925713 | 925880 | NA |
| Pvcon8364 | Phaseolus_vulgaris | 925735 | 926609 | UniRef100_A7PMB7 Chromosome chr14 scaffold_21, whole genome shotgun sequence n = 1 Tax = *Vitis vinifera* RepID = A7PMB7_VITVI 1.00E−27 |
| BE248998 | MTGI.071708 | 926978 | 927524 | similar to UniRef100_Q7F8S7 Cluster: PHD finger-like protein, n = 1, *Oryza sativa* |

Table 2 of the Specification

| Locus/ Display Name (1) | Source (2) | Start Base (3) | End Base (4) | ADDITIONAL LOCUS INFORMATION (5) |
|---|---|---|---|---|
| TC35470 | LJGI.070108 | 928423 | 929804 | *Japonica* Group\|Rep: PHD finger-like protein - *Oryza sativa* subsp. *japonica* (Rice), partial (4%) similar to UniRef100_A7PMB8 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (9%) |
| TA11035_34305 | Lotus_japonicus_release_1 | 928423 | 929825 | PHD finger-like protein [*Oryza sativa* (*japonica* cultivar-group)] |
| CA911004 | Phaseolus_coccineus_release_2 | 934882 | 939256 | T13O15.10 protein [*Arabidopsis thaliana* (Mouse-ear cress)] |
| AI856399 | GMGI.071508 | 937577 | 938041 | NA |
| AI856399 | Glycine_max_release_2 | 937577 | 938106 | NA |
| AW348703 | Glycine_max_release_2 | 963043 | 963750 | NA |
| TC276191 | GMGI.071508 | 963049 | 964044 | weakly similar to UniRef100_A7PZY3 Cluster: Chromosome chr8 scaffold_41 = whole genome shotgun sequence; n = 1; *Vitis vinifera*\|Rep: Chromosome chr8 scaffold_41 = whole genome shotgun sequence - *Vitis vinifera* (Grape) = partial (21%) |
| BQ628183 | Glycine_max_release_2 | 963625 | 964044 | NA |
| BQ080193 | Glycine_max_release_2 | 963695 | 967475 | NA |
| TA52645_3847 | Glycine_max_release_2 | 963720 | 967461 | NA |
| TC256882 | GMGI.071508 | 963774 | 967475 | weakly similar to UniRef100_A7PZY3 Cluster: Chromosome chr8 scaffold_41 = whole genome shotgun sequence; n = 1; *Vitis vinifera*\|Rep: Chromosome chr8 scaffold_41 = whole genome shotgun sequence - *Vitis vinifera* (Grape) = partial (45%) |
| BG156825 | Glycine_max_release_2 | 971121 | 971284 | NA |
| BG156825 | GMGI.071508 | 971125 | 971284 | NA |
| BU545761 | Glycine_max_release_2 | 971300 | 971901 | NA |
| BU550718 | Glycine_max_release_2 | 971255 | 973578 | NA |
| TA72701_3847 | Glycine_max_release_2 | 972120 | 972806 | NA |
| TC271942 | GMGI.071508 | 972201 | 972806 | NA |
| TC269989 | GMGI.071508 | 971255 | 973827 | similar to UniRef100_A7P2M9 Cluster: Chromosome chr1 scaffold_5 = whole genome shotgun sequence; n = 1; *Vitis vinifera*\|Rep: Chromosome chr1 scaffold_5 = whole genome shotgun sequence - *Vitis vinifera* (Grape) = partial (63%) |
| BI317782 | Glycine_max_release_2 | 971510 | 973827 | NA |
| BI893512 | Glycine_max_release_2 | 971537 | 973848 | NA |
| BI893512 | GMGI.071508 | 971671 | 973848 | similar to UniRef100_A7P2M9 Cluster: Chromosome chr1 scaffold_5 = whole genome shotgun sequence; n = 1; *Vitis vinifera*\|Rep: Chromosome chr1 scaffold_5 = whole genome shotgun sequence - *Vitis vinifera* (Grape) = partial (54%) |
| CO985587 | Glycine_max_release_2 | 974859 | 976255 | Putative GTP-binding membrane protein LepA [*Oryza sativa* (*japonica* cultivar-group)] |

-continued

Table 2 of the Specification

| Locus/ Display Name (1) | Source (2) | Start Base (3) | End Base (4) | ADDITTIONAL LOCUS INFORMATION (5) |
|---|---|---|---|---|
| AW596868 | Glycine_max_release_2 | 976346 | 976856 | NA |
| AW596868 | GMGI.071508 | 976412 | 976856 | similar to UniRef100_A2Q5T1 Cluster: Tetratricopeptide-like helical; n = 1; *Medicago truncatula*\|Rep: Tetratricopeptide-like helical - *Medicago truncatula* (Barrel medic) = partial (5%) |
| CA901672 | Phaseolus_coccineus_release_2 | 983905 | 984264 | Aldehyde dehydrogenase 1 precursor [*Lotus corniculatus* (Bird's-foot trefoil)] |
| WmFPC_Contig4169 | | 899736 | 1068750 | NA |
| FE898889 | Phaseolus_vulgaris | 983908 | 984989 | UniRef100_A7PD33 Chromosome chr17 scaffold_12, whole genome shotgun sequence n = 1 Tax = *Vitis vinifera* RepID = A7PD33_VITVI 2.00E−79 |
| TC273361 | GMGI.071508 | 984396 | 986122 | similar to UniRef100_P93344 Cluster: Aldehyde dehydrogenase; n = 1; *Nicotiana tabacum*\|Rep: Aldehyde dehydrogenase - *Nicotiana tabacum* (Common tobacco) = partial (37%) |
| BE473475 | Glycine_max_release_2 | 984960 | 986122 | Aldehyde dehydrogenase [*Nicotiana tabacum* (Common tobacco)] |
| CV539672 | Phaseolus_vulgaris | 985959 | 987101 | UniRef100_P93344 Aldehyde dehydrogenase (NAD+) n = 1 Tax = *Nicotiana tabacum* RepID = P93344_TOBAC 7.00E−50 |
| AV410805 | LJGI.070108 | 987592 | 987888 | similar to UniRef100_A7PMC7 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (6%) |
| TC265505 | GMGI.071508 | 1011306 | 1012664 | similar to UniRef100_A7PMD1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (28%) |
| TA51641_3847 | Glycine_max_release_2 | 1011306 | 1013783 | Putative high-affinity potassium transporter protein 1 [*Nicotiana tabacum* (Common tobacco)] |
| CB540416 | Phaseolus_vulgaris | 1012333 | 1013531 | UniRef100_A7PMD1 Chromosome chr14 scaffold_21, whole genome shotgun sequence n = 1 Tax = *Vitis vinifera* RepID = A7PMD1_VITVI 5.00E−97 |
| BM891067 | GMGI.071508 | 1012675 | 1013617 | similar to UniRef100_A7PMD1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (22%) |
| TC131883 | MTGI.071708 | 1012665 | 1014070 | similar to UniRef100_A7PMD1 Cluster: Chromosome chr14 scaffold_21, whole genome |

Table 2 of the Specification

| Locus/ Display Name (1) | Source (2) | Start Base (3) | End Base (4) | ADDITTIONAL LOCUS INFORMATION (5) |
|---|---|---|---|---|
| | | | | shotgun sequence, n = 1, *Vitis vinifera*\|Rep: Chromosome chr14 scaffold_21, whole genome shotgun sequence - *Vitis vinifera* (Grape), partial (34%) |
| asmbl_11884 | Vigna_unguiculata | 1012674 | 1014123 | NA |
| BE330787 | Glycine_max_release_2 | 1013888 | 1014305 | Putative high-affinity potassium transporter protein [*Phytolacca esculenta* (Food pokeberry)] |
| FD792954 | Phaseolus_vulgaris | 1013779 | 1014573 | UniRef100_A7PMD1 Chromosome chr14 scaffold_21, whole genome shotgun sequence n = 1 Tax = *Vitis vinifera* RepID = A7PMD1_VITVI 3.00E−57 |
| TC244134 | GMGI.071508 | 1014004 | 1014793 | similar to UniRef100_A7PMD1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (15%) |
| TA51642_3847 | Glycine_max_release_2 | 1013926 | 1014875 | Putative high-affinity potassium transporter 1 [*Nicotiana rustica* (Aztec tobacco)] |
| TC242106 | GMGI.071508 | 1013926 | 1014875 | similar to UniRef100_A7PMD1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (15%) |
| BI970123 | Glycine_max_release_2 | 1014128 | 1014721 | Putative potassium transporter HAK1p [*Mesembryanthemum crystallinum* (Common ice plant)] |
| BQ080303 | Glycine_max_release_2 | 1018604 | 1019142 | NA |
| TC270109 | GMGI.071508 | 1018604 | 1019142 | weakly similar to UniRef100_UPI0000196D39 Cluster: NHL repeat-containing protein; n = 1; *Arabidopsis thaliana*\|Rep: NHL repeat-containing protein - *Arabidopsis thaliana* = partial (4%) |
| BQ080219 | Glycine_max_release_2 | 1018604 | 1019579 | NA |
| TA62145_3847 | Glycine_max_release_2 | 1021347 | 1023221 | NA |
| TC245123 | GMGI.071508 | 1021347 | 1023221 | similar to UniRef100_A7PMD2 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (31%) |
| asmbl_11885 | Vigna_unguiculata | 1022417 | 1022510 | NA |
| CA784724 | Glycine_max_release_2 | 1046117 | 1047384 | NA |
| CA784724 | GMGI.071508 | 1046400 | 1047384 | similar to UniRef100_A7Q2E7 Cluster: Chromosome chr1 scaffold_46 = whole genome shotgun sequence; n = 1; *Vitis vinifera*\|Rep: Chromosome chr1 scaffold_46 = whole genome shotgun sequence - *Vitis vinifera* (Grape) = partial (17%) |

-continued

Table 2 of the Specification

| Locus/ Display Name (1) | Source (2) | Start Base (3) | End Base (4) | ADDITTIONAL LOCUS INFORMATION (5) |
|---|---|---|---|---|
| Pvcon4015 | Phaseolus_vulgaris | 1047011 | 1048610 | UniRef100_A5ATC1 Putative uncharacterized protein n = 1 Tax = *Vitis vinifera* RepID = A5ATC1_VITVI 1.00E−146 |
| BQ742289 | Glycine_max_release_2 | 1048650 | 1048767 | NA |
| BF068315 | GMGI.071508 | 1057203 | 1057316 | similar to UniRef100_Q8MIG1 Cluster: Skinkine; n = 1; *Sus scrofa*\|Rep: Skinkine - *Sus scrofa* (Pig) = partial (12%) |
| BF068315 | Glycine_max_release_2 | 1057203 | 1057506 | NA |
| BU083500 | GMGI.071508 | 1058026 | 1058431 | UniRef100_Q2R023 Cluster: Expressed protein; n = 1; *Oryza sativa Japonica* Group\|Rep: Expressed protein - *Oryza sativa* = partial (2%) |
| TA74227_3847 | Glycine_max_release_2 | 1058026 | 1059408 | NA |
| BI423963 | GMGI.071508 | 1058432 | 1059275 | similar to UniRef100_Q2QDD6 Cluster: Nodulin-like protein; n = 1; *Gossypium hirsutum*\|Rep: Nodulin-like protein - *Gossypium hirsutum* (Upland cotton) (*Gossypium mexicanum*) = partial (22%) |
| TC237120 | GMGI.071508 | 1063015 | 1063972 | UniRef100_Q39819 Cluster: Hsp22.3; n = 1; *Glycine max*\|Rep: Hsp22.3 - *Glycine max* (Soybean) = complete |
| CA802234 | Glycine_soja_release_2 | 1061477 | 1067499 | Similarity to nodulin [*Arabidopsis thaliana* (Mouse-ear cress)] |
| BI425574 | GMGI.071508 | 1065519 | 1066854 | weakly similar to UniRef100_A7PMD8 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (21%) |
| BI425574 | Glycine_max_release_2 | 1065519 | 1066940 | Hypothetical protein [*Medicago truncatula* (Barrel medic)] |
| AU251786 | LJGI.070108 | 1066790 | 1067424 | weakly similar to UniRef100_A7Q2G7 Cluster: Chromosome chr1 scaffold_46, whole genome shotgun sequence, n = 1, *Vitis vinifera*\|Rep: Chromosome chr1 scaffold_46, whole genome shotgun sequence - *Vitis vinifera* (Grape), partial (7%) |
| Pvcon8451 | Phaseolus_vulgaris | 1065511 | 1068752 | UniRef100_A7PMD8 Chromosome chr14 scaffold_21, whole genome shotgun sequence n = 1 Tax = *Vitis vinifera* RepID = A7PMD8_VITVI 7.00E−91 |
| TC260900 | GMGI.071508 | 1065796 | 1069134 | weakly similar to UniRef100_A7PMD8 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (41%) |
| TA63020_3847 | Glycine_max_release_2 | 1067436 | 1069134 | NA |
| CA783703 | Glycine_soja_release_2 | 1068257 | 1068879 | NA |

-continued

Table 2 of the Specification

| Locus/Display Name (1) | Source (2) | Start Base (3) | End Base (4) | ADDITTIONAL LOCUS INFORMATION (5) |
|---|---|---|---|---|
| TA58065_3847 | Glycine_max_release_2 | 1074998 | 1076541 | AT3g28050/MMG15_6 [*Arabidopsis thaliana* (Mouse-ear cress)] |
| TC251785 | GMGI.071508 | 1074998 | 1076541 | similar to UniRef100_Q8L9I2 Cluster: Nodulin MtN21-like protein; n = 1; *Arabidopsis thaliana*\|Rep: Nodulin MtN21-like protein - *Arabidopsis thaliana* (Mouse-ear cress) = partial (16%) |
| CB280623 | Phaseolus_vulgaris_release_2 | 1075036 | 1076540 | AT3g28050/MMG15_6 [*Arabidopsis thaliana* (Mouse-ear cress)] |
| EH043320 | Arachis_stenosperma_release_5 | 1075056 | 1077422 | Cluster: Hypothetical protein, n = 1, *Medicago truncatula*\|Rep: Hypothetical protein - *Medicago truncatula* (Barrel medic) |
| asmbl_11886 | Vigna_unguiculata | 1075036 | 1077585 | NA |
| BQ094260 | Glycine_max_release_2 | 1075548 | 1077551 | Nodulin-like protein [*Arabidopsis thaliana* (Mouse-ear cress)] |
| BF598290 | Glycine_soja_release_2 | 1075557 | 1077593 | Nodulin-like protein [*Arabidopsis thaliana* (Mouse-ear cress)] |
| Pvcon6314 | Phaseolus_vulgaris | 1075036 | 1078733 | UniRef100_A7PMD8 Chromosome chr14 scaffold_21, whole genome shotgun sequence n = 1 Tax = *Vitis vinifera* RepID = A7PMD8_VITVI 1.00E−105 |
| TA58064_3847 | Glycine_max_release_2 | 1075337 | 1079189 | AT3g28050/MMG15_6 [*Arabidopsis thaliana* (Mouse-ear cress)] |
| TC255833 | GMGI.071508 | 1075337 | 1079189 | weakly similar to UniRef100_A7PMD8 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (64%) |
| BG042956 | Glycine_soja_release_2 | 1078885 | 1079014 | NA |
| TC263589 | GMGI.071508 | 1086875 | 1091139 | similar to UniRef100_A7PME0 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (35%) |
| TA50577_3847 | Glycine_max_release_2 | 1086875 | 1094082 | Alpha-dioxygenase [*Pisum sativum* (Garden pea)] |
| asmbl_11887 | Vigna_unguiculata | 1089135 | 1092345 | NA |
| CA410123 | Lupinus_albus_release_2 | 1092182 | 1092694 | Alpha-dioxygenase [*Pisum sativum* (Garden pea)] |
| Pvcon4974 | Phaseolus_vulgaris | 1091225 | 1093836 | UniRef100_Q5GQ66 Alpha-dioxygenase n = 1 Tax = *Pisum sativum* RepID = Q5GQ66_PEA E-0 |
| TC243973 | GMGI.071508 | 1091177 | 1094141 | similar to UniRef100_Q5GQ66 Cluster: Alpha-dioxygenase; n = 1; *Pisum sativum*\|Rep: Alpha-dioxygenase - *Pisum sativum* (Garden pea) = partial (61%) |
| asmbl_11888 | Vigna_unguiculata | 1092518 | 1093829 | NA |
| M0206054 | SEQ. Listing | 1465522 | 1465187 | SEQ ID NO: 11 |
| M0205375 | SEQ. Listing | 2010060 | 2009541 | SEQ ID NO: 12 |

Table 2 of the Specification

| Locus/<br>Display Name<br>(1) | Source (2) | Start<br>Base (3) | End<br>Base (4) | ADDITTIONAL LOCUS<br>INFORMATION (5) |
|---|---|---|---|---|
| toGm13 | DAGchainer | 1046081 | 4647877 | Ks0.2059 |
| NA | Glyma1 | 1 | 50600000 | NA |

Sequences for the genes provided above can be obtained from the World Wide Web (or Internet) using the identifiers provided in Column 1 (Locus/Display Name) or Column 5 (ADDITIONAL LOCUS INFORMATION) from the following internet locations:

a) "soybase.org" (described in Grant et al., Nucleic Acids Research, 2010, Vol. 38, Database issue D843-D846) or soybase.org/gbrowse/cgi-bin/gbrowse/gmax1.01/(see Hyten DL, Choi I-Y, Song Q, Specht J E, Carter T E et al. (2010) A high density integrated genetic linkage map of soybean and the development of a 1,536 Universal Soy Linkage Panel for QTL mapping. Crop Science 50:960-968. (Crop Science); and Hyten DL, Cannon SB, Song Q, Weeks N, Fickus E W et al. (2010) High-throughput SNP discovery through deep resequencing of a reduced representation library to anchor and orient scaffolds in the soybean whole genome sequence. BMC Genomics 11(1): 38);

b) "phytozome.net" or "phytozome.net/cgi-bin/gbrowse/soybean/?name=Gm09";

c) "plantgdb.org" or "plantgdb.org/GmGDB/(Assembly version Glyma1.170 (April 2009)"; and, d) "ncbi.nlm.nih.gov/sites/entrez" and subsites "ncbi.nlm.nih.gov/nucest", "ncbi.nlm.nih.gov/dbEST", "ncbi.nlm.nih.gov/genbank/", ".ncbi.nlm.nih.gov/sites/genome", "ncbi.nlm.nih.gov/unigene", and "ncbi.nlm.nih.gov/UniGene/UGOrg.cgi?TAXID=3847".

We claim:

1. A method of identifying a soybean plant that comprises a genotype associated with a no flash phenotype, comprising: detecting in said soybean plant a DNA polymorphism in at least one yellow flash marker locus associated with the no flash phenotype with a nucleic acid analysis technique, wherein the yellow flash marker locus is in a linkage group L genomic region flanked by loci BG406195 (SEQ ID NO: 13) and BU082700 (SEQ ID NO:14), and selecting said plant from a population of plants, wherein the selected plant comprises a genotype associated with a no flash phenotype and wherein the selected plant or progeny thereof exhibit a no flash phenotype.

2. The method of claim 1, wherein said selected plant or progeny thereof comprises a transgene that confers tolerance to glyphosate.

3. The method of claim 2, wherein said soybean plant or progeny thereof is exposed to a dosage of glyphosate sufficient to cause yellow flash in a susceptible variety.

4. The method of claim 1, wherein said genotype associated with a no flash phenotype is detected by identifying at least one polymorphic allele of at least one marker in a first sub-region of said linkage group L region that is flanked by loci BG406195 (SEQ ID NO: 13) and BU551345 (SEQ ID NO: 16) and/or at least one polymorphic allele of at least one marker in a second sub-region of said linkage group L region that is flanked by loci TA14086_34305 (SEQ ID NO: 15) and BU082700 (SEQ ID NO: 14) with the nucleic acid analysis technique.

5. The method of claim 1, wherein said genotype associated with a no flash phenotype is detected by identifying at least one polymorphic allele of at least one marker in said linkage group L region selected from the group consisting of M0129138 (SEQ ID NO:4), M0101742 (SEQ ID NO:5), M0093116 (SEQ ID NO:6), and M0129925 (SEQ ID NO:7) that is associated with a no flash phenotype with the nucleic acid analysis technique.

6. A method for obtaining a soybean plant comprising in its genome at least one no flash locus, comprising the steps of:
   a. genotyping a plurality of soybean plants with respect to at least one yellow flash locus in a first linkage group L genomic region flanked by loci BG406195 (SEQ ID NO: 13) and BU082700 (SEQ ID NO:14), wherein said plurality of soybean plants comprises a population that is obtained by: i) crossing a parent plant comprising at least one no flash locus with a parent plant comprising at least one yellow flash locus; or, ii) obtaining seed or progeny from a parental plant segregating for at least one no flash locus; and
   b. selecting a soybean plant comprising in its genome at least one no flash locus comprising a genotype associated with no flash phenotype, wherein the selected plant exhibits a no flash phenotype.

7. The method of claim 6, wherein said genotype associated with a no flash phenotype comprises at least one polymorphic allele of at least one marker in a first sub-region of said linkage group L region that is flanked by loci BG406195 (SEQ ID NO: 13) and BU551345 (SEQ ID NO: 16); and/or at least one polymorphic allele of at least one marker in a second sub-region of said linkage group L region that is flanked by loci TA14086_34305 (SEQ ID NO: 15) and BU082700 (SEQ ID NO: 14).

8. The method of claim 6, wherein said genotype associated with a no flash phenotype comprises at least one polymorphic allele of at least one marker in said first linkage group L region, said first sub-region, or said second sub-region, wherein said marker is selected from the group consisting of M0129138 (SEQ ID NO:4), M0101742 (SEQ ID NO:5), M0093116 (SEQ ID NO:6), and M0129925 (SEQ ID NO:7).

9. The method of claim 6, wherein said plurality of soybean plants comprises a population that is obtained from seed or progeny from a parental plant segregating for at least one no flash locus.

10. The method of claim 6, wherein said population contains plants that comprise a transgene that confers tolerance to glyphosate.

11. The method of claim 6, further comprising the step of assaying for the presence of at least one additional marker, wherein said additional marker is either linked or unlinked to said linkage group L genomic region.

12. The method of claim 6, wherein said plurality of soybean plants, said soybean plant, and/or progeny thereof are exposed to a dosage of glyphosate sufficient to cause yellow flash in a susceptible variety.

13. A method for producing a soybean plant comprising in its genome at least one introgressed no flash locus, comprising the steps of:
   a. crossing a first no flash soybean plant with a second soybean plant, wherein the second soybean plant comprises a yellow flash locus in a first linkage group L genomic region flanked by loci BG406195 (SEQ ID NO: 13) and BU082700 (SEQ ID NO: 14) and at least one linked polymorphic locus not present in said first no flash soybean plant, to obtain a population segregating for the no flash loci and said linked polymorphic locus;
   b. detecting at least two polymorphic nucleic acids in a seed or progeny plant from at least one soybean plant from said population, wherein at least one of said polymorphic nucleic acids is located in said first linkage group L region that is flanked by loci BG406195 (SEQ ID NO: 13) and BU082700 (SEQ ID NO: 14) and wherein at least one of said polymorphic nucleic acids is in a linked polymorphic locus not present in said first no flash soybean plant; and
   c. selecting a seed or progeny soybean plant from step b by its genotype, wherein the selected seed or progeny soybean plant comprises a genotype of the first linkage group L region that is flanked by loci BG406195 (SEQ ID NO: 13) and BU082700 (SEQ ID NO: 14) that is associated with a no flash phenotype and at least one linked marker found in said second soybean plant comprising a yellow flash locus but not in said first no flash soybean plant, thereby obtaining a selected soybean plant comprising in its genome at least one introgressed no flash locus.

14. The method of claim 13, wherein at least one of said first or said second soybean plants comprises a transgene that confers tolerance to glyphosate.

15. The method of claim 14, wherein said population, said selected soybean plant, and/or progeny of said selected soybean plant is exposed to a dosage of glyphosate sufficient to cause yellow flash in a susceptible variety.

16. The method of claim 13, wherein said yellow flash locus comprises at least one polymorphic allele of at least one marker in a first sub-region of said linkage group L region that is flanked by loci BG406195 (SEQ ID NO: 13) and BU551345 (SEQ ID NO: 16); and/or at least one polymorphic allele of at least one marker in a second sub-region of said linkage group L region that is flanked by loci TA14086_34305 (SEQ ID NO: 15) and BU082700 (SEQ ID NO: 14).

17. The method of claim 16, wherein said polymorphic nucleic acid located in said first sub-region and/or said second sub-region is detected in step (b) with at least one marker selected from the group consisting of M0129138 (SEQ ID NO:4), M0101742 (SEQ ID NO:5), M0093116 (SEQ ID NO:6), and M0129925 (SEQ ID NO:7).

18. The method of claim 17, wherein said polymorphic nucleic acid located in said first sub-region and/or said second sub-region is detected in step (b) with at least one marker selected from the group consisting of M0101742 (SEQ ID NO:5) and M0129925 (SEQ ID NO:7).

19. The method of claim 17, wherein said polymorphic nucleic acids are detected with marker M0101742 (SEQ ID NO:5) and with marker M0129925 (SEQ ID NO:7).

20. The method of claim 13, wherein said linked polymorphic locus is detected with a genotypic marker, a phenotypic marker, or both.

21. The method of claim 13, wherein said linked polymorphic locus is detected with a marker that is located within about 1000, 500, 100, 40, 20, 10, or 5 kilobases (Kb) of said no flash locus.

22. The method of claim 21, wherein said linked polymorphic locus is detected with at least one marker selected from the group consisting of M0205928 (SEQ ID NO:3), M0205537 (SEQ ID NO:8), M0202715 (SEQ ID NO:9), M0206286 (SEQ ID NO:10), M0206054 (SEQ ID NO:11) and M0205375 (SEQ ID NO:12).

23. A selected soybean plant produced by the method of claim 13 that comprises the introgressed no flash locus from the first no flash soybean plant and one or more polymorphic loci comprising alleles or combinations of alleles that are not found in the first no flash soybean plant, that are linked to said introgressed no flash locus, and are found in the second soybean plant comprising a yellow flash locus, wherein at least 75% of genomic sequences in said selected plant have markers characteristic of soybean germplasm that comprise a genomic region associated with a yellow flash phenotype.

24. The selected soybean plant of claim 23, wherein said introgressed no flash locus comprises at least one polymorphic allele of at least one marker selected from the group consisting of M0129138 (SEQ ID NO:4), M0101742 (SEQ ID NO:5), M0093116 (SEQ ID NO:6), and M0129925 (SEQ ID NO:7) that is associated with a no flash phenotype.

25. The selected soybean plant of claim 24, wherein said polymorphic alleles associated with a no flash phenotype comprise:
   (i) GG alleles at nucleotide 218 of SEQ ID NO:4, TT alleles at nucleotide 1206 of SEQ ID NO:5, AA alleles at nucleotide 183 of SEQ ID NO:6, and CC alleles at nucleotide 328 of SEQ ID NO:7; or,
   (ii) AA alleles at nucleotide 218 of SEQ ID NO:4, CC alleles at nucleotide 1206 of SEQ ID NO:5, TT alleles at nucleotide 183 of SEQ ID NO:6, and GG alleles at nucleotide 328 of SEQ ID NO:7.

26. The selected soybean plant of claim 24, wherein said one or more polymorphic loci comprising alleles or combinations of alleles that are not found in a no flash soybean variety are located within about 1000, 500, 100, 40, 20, 10, or 5 kilobases (Kb) of said introgressed no flash locus.

27. The selected soybean plant of claim 24, wherein said one or more polymorphic loci comprise an allele that are not found in a no flash soybean variety that is detectable with at least one marker selected from the group consisting of M0205928 (SEQ ID NO:3), M0205537 (SEQ ID NO:8), M0202715 (SEQ ID NO:9), M0206286 (SEQ ID NO:10), M0206054 (SEQ ID NO:11) and M0205375 (SEQ ID NO:12).

28. The method of claim 5, wherein said genotype associated with a no flash phenotype is detected by identifying at least one of: GG or AA alleles at nucleotide 218 of SEQ ID NO:4, TT or CC alleles at nucleotide 1206 of SEQ ID NO:5, AA or TT alleles at nucleotide 183 of SEQ ID NO:6, and/or CC or GG alleles at nucleotide 328 of SEQ ID NO:7 with the nucleic acid analysis technique.

29. The method of claim 5, wherein said genotype associated with a no flash phenotype is detected by identifying:
(i) GG alleles at nucleotide 218 of SEQ ID NO:4, TT alleles at nucleotide 1206 of SEQ ID NO:5, AA alleles at nucleotide 183 of SEQ ID NO:6, and CC alleles at nucleotide 328 of SEQ ID NO:7 with the nucleic acid analysis technique; or,
(ii) AA alleles at nucleotide 218 of SEQ ID NO:4, CC alleles at nucleotide 1206 of SEQ ID NO:5, TT alleles at nucleotide 183 of SEQ ID NO:6, and GG alleles at nucleotide 328 of SEQ ID NO:7 with the nucleic acid analysis technique.

30. The selected soybean plant of claim 23, wherein at least 90% of genomic sequences in said selected plant have markers characteristic of soybean germplasm that comprise a genomic region associated with a yellow flash phenotype.

31. The selected soybean plant of claim 23, wherein at least 99% of genomic sequences in said selected plant have markers characteristic of soybean germplasm that comprise a genomic region associated with a yellow flash phenotype.

* * * * *

UNITED STATES PATENT AND TRADEMARK OFFICE
CERTIFICATE OF CORRECTION

Page 1 of 1

PATENT NO. : 8,921,647 B2
APPLICATION NO. : 13/224036
DATED : December 30, 2014
INVENTOR(S) : Liesa Cerny, Kunsheng Wu and Tom Floyd It is certified that error appears in the above-identified patent and that said Letters Patent is hereby corrected as shown below:

In the Claims,

Column 131, Line 8, cancel the text beginning with "27. The selected soybean plant" to and ending in "and M0205375 (SEQ ID NO:12)." and insert the following claim:

--27. The selected soybean plant of claim 24, wherein said one or more polymorphic loci comprise an allele that is not found in a no flash soybean variety that is detectable with at least one marker selected from the group consisting of M0205928 (SEQ ID NO:3), M0205537 (SEQ ID NO:8), M0202715 (SEQ ID NO:9), M0206286 (SEQ ID NO:10), M0206054 (SEQ ID NO:11) and M0205375 (SEQ ID NO:12).--

Signed and Sealed this
Nineteenth Day of May, 2015

Michelle K. Lee
*Director of the United States Patent and Trademark Office*